US009206403B1

(12) United States Patent
Zhan et al.

(10) Patent No.: US 9,206,403 B1
(45) Date of Patent: Dec. 8, 2015

(54) HIGH-ACTIVITY MUTANTS OF BUTYRYLCHOLINESTERASE FOR COCAINE HYDROLYSIS AND METHOD OF GENERATING THE SAME

(71) Applicant: University of Kentucky Research Foundation, Lexington, KY (US)

(72) Inventors: Chang-Guo Zhan, Lexington, KY (US); Hoon Cho, Lexington, KY (US); Hsin-Hsiung Tai, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 136 days.

(21) Appl. No.: 14/163,376

(22) Filed: Jan. 24, 2014

Related U.S. Application Data

(62) Division of application No. 13/767,418, filed on Feb. 14, 2013, now Pat. No. 8,835,150, which is a division of application No. 13/449,107, filed on Apr. 17, 2012, now Pat. No. 8,399,644, which is a division of application No. 13/018,641, filed on Feb. 1, 2011, now Pat. No. 8,193,327, which is a division of application No. 12/752,920, filed on Apr. 1, 2010, now Pat. No. 7,919,082, which is a division of application No. 12/192,394, filed on Aug. 15, 2008, now Pat. No. 7,731,957, which is a division of application No. 11/243,111, filed on Oct. 4, 2005, now Pat. No. 7,438,904.

(51) Int. Cl.
*C12N 9/16* (2006.01)
*C12N 9/18* (2006.01)

(52) U.S. Cl.
CPC .................................... *C12N 9/18* (2013.01)

(58) Field of Classification Search
CPC ................................ C12N 9/18; A61K 38/00
USPC ...................................................... 435/196
See application file for complete search history.

(56) References Cited

U.S. PATENT DOCUMENTS

| | | | |
|---|---|---|---|
| 7,049,121 | B2 | 5/2006 | Watkins et al. |
| 2003/0153062 | A1 | 8/2003 | Watkins et al. |
| 2004/4012093 | | 6/2004 | Watkins et al. |

OTHER PUBLICATIONS

Huang, Xiaoqin et al., Reaction Pathway and Free Energy Profile for Prechemical Reaction Step of Human Butyrylcholinesterase-Catalyzed Hydrolysis of (−)-Cocaine by Combined Targeted Molecular Dynamics and Potential of Mean Force Simulations; J. Phys. Chem., 2010, vol. 114, pp. 13545-13554.

Xue, Liu et al., Design, Preparation, and Characterization of High-Activity Mutants of Human Butyrylcholinesterase Specific for Detoxification of Cocaine, Molecular Pharmacology, 2011, vol. 79, pp. 290-297.

Yang, Wenchao et al., Characterization of a high-activity mutant of human butyrylcholinesterase against (−)-cocaine, Chemico-Biological Interactions, 2010, vol. 187, pp. 148-152.

Yang, Wenchao et al., Free-Energy Perturbation Simulation on Transition States and Redesign of Butyrylcholinesterase, 2009, vol. 96, pp. 1931-1938.

Yang, Wenchao et al., Free Energy Perturbation Simulation on Transition States and High-Activity Mutants of Human Butyrylcholinesterase for (−)-Cocaine Hydrolysis, J. Phys. Chem., 2010, vol. 114, pp. 10889-10896.

Pan, Yongmei et al., Free Energy Perturbation (FEP) Simulation on the Transition States of Cocaine Hydrolysis Catalyzed by Human Butyrylcholinesterase and its Mutants, J. Am. Chem. Soc., 2007, vol. 129, pp. 13537-13543.

Pan, Yongmei et al., Model of Human Butyrylcholinesterase Tetramer by Homology Modeling and Dynamics Simulation, J. Phys. Chem., 2009, vol. 113, pp. 6543-6552.

Zheng, Fang et al., Rational design of an enzyme mutant for anti-cocaine therapeutics, J. Comput Aided Mol. Des., 2008, vol. 22, pp. 661-671.

Zheng, Fang et al., Structure-and-mechanism-based design and discovery of therapeutics for cocaine overdose and addiction, Organic & Biomolecular Chemistry, 2008, vol. 6, pp. 836-843.

Zheng, Fang et al., Design of High-Activity Mutants of Human Butyrylcholinesterase against (−)-Cocaine: Structural and Energetic Factors Affecting the Catalytic Efficiency, Biochemistry, 2010, vol. 49, pp. 9113-9119.

Zheng, Fang et al., Recent progress in protein drug design and discovery with a focus on novel approaches to the development of anticocaine medications, Future Med. Chem, 2009), vol. 1, No. 3, pp. 515-528.

Zheng, Fang et al., Enzyme-therapy approaches for the treatment of drug overdose and addition, Future Med. Chem., 2011, vol. 3, No. 1, pp. 9-13.

Zheng, Fang et al., Most Efficient Cocaine Hydrolase Designed by Virtual Screening of Transition States, J. Am. Chem. Soc., 2008, vol. 130, pp. 12148-12155.

(Continued)

*Primary Examiner* — Tekchand Saidha
(74) *Attorney, Agent, or Firm* — Stites & Harbison PLLC; Mandy Wilson Decker

(57) ABSTRACT

A novel computational method and generation of mutant butyrylcholinesterase for cocaine hydrolysis is provided. The method includes molecular modeling a possible BChE mutant and conducting molecular dynamics simulations and hybrid quantum mechanical/molecular mechanical calculations thereby providing a screening method of possible BChE mutants by predicting which mutant will lead to a more stable transition state for a rate determining step. Site-directed mutagenesis, protein expression, and protein activity is conducted for mutants determined computationally as being good candidates for possible BChE mutants, i.e., ones predicted to have higher catalytic efficiency as compared with wild-type BChE. In addition, mutants A199S/A328W/Y332G, A199S/F227A/A328W/Y332G, A199S/S287G/A328W/Y332G, A199S/F227A/S287G/A328W/Y332G, and A199S/F227A/S287G/A328W/E441D all have enhanced catalytic efficiency for (−)-cocaine compared with wild-type BChE.

6 Claims, 6 Drawing Sheets

(56) References Cited

OTHER PUBLICATIONS

Gao, et al.; Modeling effects of oxyanion hole on the ester hydrolyses catalyzed by human cholinesterases; Phys. Chem. B; 2005; 109; pp. 23070-23076.

Gao, et al; Computational design of a human butyrylcholinesterase mutant for accelerating cocaine hydrolysis based on the transition-state simulation; Angew. Chem. Int. Ed.; 2006; 45; pp. 653-657.

Gao, et al; Modeling evolution of hydrogen bonding and stablization of transition states in the process of cocaine hydrolysis catalyzed by human butyrylcholinesterase; Proteins; 2006; 62; pp. 99-110.

Hamza, et al.; Molecular dynamics simulation of cocaine binding with human butyrylcholinesterase and its mutants; J. Phys. Chem. B.; 2005; 109; pp. 4776-4782.

Pan, et al.; Computational redesign of human butyrylcholinesterase for anti-cocaine medication; G. Proc. Natl. Acad. Sci. USA; 2005; 102; pp. 16656-16661.

Zhan, et al.; Fundamental reaction mechanism for cocaine metabolism in human butyrylcholinesterase; J. Am. Chem. Soc.; 2003; 125; pp. 2462-2474.

Zhan, et al.; Catalytic Mechanism and energy barriers for butyrylcholinesterase-catalyzed hydrolysis of cocaine; Biophysical Journal; 2005; 89; 3863-3872.

Xie, et al.; An improved cocaine hydrolase: the A328Y mutant of human butyrylcholinesterase is 4-fold more efficient; Moleculare Pharm; 1999; 55; pp. 83-91.

(A)

(B)

(A) BChE-(-)-cocaine non-prereactive complex (B) BChE-(-)-cocaine prereactive complex (C) BChE-(+)-cocaine non-prereactive complex (D) BChE-(+)-cocaine prereactive complex (A) (B)

(A)

SEQUENCE LISTING

```
<160> NUMBER OF SEQ ID NOS: 30

<210> SEQ ID NO 1
<211> LENGTH: 1722
<212> TYPE: DNA
<213> ORGANISM: Artificial
<220> FEATURE:
<223> OTHER INFORMATION: 14-1 mutant A199S/A328W/Y332G of Human
      butyrylcholinesterase (BChE)

<400> SEQUENCE: 1

gaagatgaca tcataattgc aacaaagaat ggaaaagtca gagggatgaa cttgacagtt     60

tttggtggca cggtaacagc ctttcttgga attccctatg cacagccacc tcttggtaga    120

cttcgattca aaaagccaca gtctctgacc aagtggtctg atatttggaa tgccacaaaa    180

tatgcaaatt cttgctgtca gaacatagat caaagttttc caggcttcca tggatcagag    240

atgtggaacc caaacactga cctcagtgaa gactgtttat atctaaatgt atggattcca    300

gcacctaaac caaaaaatgc cactgtattg atatggattt atggtggtgg ttttcaaact    360

ggaacatcat ctttacatgt ttatgatggc aagtttctgg ctcgggttga aagagttatt    420

gtagtgtcaa tgaactatag ggtgggtgcc ctaggattct tagctttgcc aggaaatcct    480

gaggctccag ggaacatggg tttatttgat caacagttgg ctcttcagtg ggttcaaaaa    540

aatatagcag cctttggtgg aaatcctaaa agtgtaactc tctttggaga aagttccgga    600

gcagcttcag ttagcctgca tttgctttct cctggaagcc attcattgtt caccagagcc    660

attctgcaaa gtggttcctt taatgctcct tgggcggtaa catctcttta tgaagctagg    720

aacagaacgt tgaacttagc taaattgact ggttgctcta gagagaatga gactgaaata    780

atcaagtgtc ttagaaataa agatccccaa gaaattcttc tgaatgaagc atttgttgtc    840

ccctatggga ctcctttgtc agtaaacttt ggtccgaccg tggatggtga ttttctcact    900

gacatgccag acatattact tgaacttgga caatttaaaa aaacccagat tttggtgggt    960

gttaataaag atgaagggac atggttttta gtcggtggtg ctcctggctt cagcaaagat   1020

aacaatagta tcataactag aaaagaattt caggaaggtt taaaaatatt ttttccagga   1080

gtgagtgagt ttggaaagga atccatcctt tttcattaca cagactgggt agatgatcag   1140

agacctgaaa actaccgtga ggccttgggt gatgttgttg gggattataa tttcatatgc   1200

cctgccttgg agttcaccaa gaagttctca gaatggggaa ataatgcctt tttctactat   1260

tttgaacacc gatcctccaa acttccgtgg ccagaatgga tgggagtgat gcatggctat   1320

gaaattgaat ttgtctttgg tttacctctg gaaagaagag ataattacac aaaagccgag   1380

gaaattttga gtagatccat agtgaaacgg tgggcaaatt ttgcaaaata tgggaatcca   1440

aatgagactc agaacaatag cacaagctgg cctgtcttca aaagcactga acaaaaatat   1500

ctaaccttga atacagagtc aacaagaata atgacgaaac tacgtgctca acaatgtcga   1560

ttctggacat catttttttcc aaaagtcttg gaaatgacag gaaatattga tgaagcagaa   1620
```

-continued tgggagtgga aagcaggatt ccatcgctgg aacaattaca tgatggactg gaaaaatcaa 1680
tttaacgatt acactagcaa gaaagaaagt tgtgtgggtc tc 1722

<210> SEQ ID NO 2
<211> LENGTH: 574
<212> TYPE: PRT
<213> ORGANISM: Artificial
<220> FEATURE:
<223> OTHER INFORMATION: 14-1 mutant (A199S/A328W/Y332G) amino acid sequence modified BChE

<400> SEQUENCE: 2

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu

-continued

```
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570
```

<210> SEQ ID NO 3
<211> LENGTH: 1125
<212> TYPE: DNA
<213> ORGANISM: Artificial
<220> FEATURE:
<223> OTHER INFORMATION: truncated 14-1 (A199S/A328/Y332G) nucleic Acid Sequence for modified BChE corresponding to a.a. residues 68-442

<400> SEQUENCE: 3

```
aacatagatc aaagttttcc aggcttccat ggatcagaga tgtggaaccc aaacactgac      60

ctcagtgaag actgtttata tctaaatgta tggattccag cacctaaacc aaaaaatgcc     120

actgtattga tatggattta tggtggtggt tttcaaactg gaacatcatc tttacatgtt     180

tatgatggca agtttctggc tcgggttgaa agagttattg tagtgtcaat gaactatagg     240

gtgggtgccc taggattctt agctttgcca ggaaatcctg aggctccagg gaacatgggt     300

ttatttgatc aacagttggc tcttcagtgg gttcaaaaaa atatagcagc ctttggtgga     360

aatcctaaaa gtgtaactct ctttggagaa agttccggag cagcttcagt tagcctgcat     420

ttgctttctc ctggaagcca ttcattgttc accagagcca ttctgcaaag tggttccttt     480

aatgctcctt gggcggtaac atctctttat gaagctagga acagaacgtt gaacttagct     540

aaattgactg gttgctctag agagaatgag actgaaataa tcaagtgtct tagaaataaa     600

gatccccaag aaattcttct gaatgaagca tttgttgtcc cctatgggac tcctttgtca     660

gtaaactttg gtccgaccgt ggatggtgat tttctcactg acatgccaga catattactt     720
```

-continued

```
gaacttggac aatttaaaaa aacccagatt ttggtgggtg ttaataaaga tgaagggaca     780

tggtttttag tcggtggtgc tcctggcttc agcaaagata acaatagtat cataactaga     840

aaagaatttc aggaaggttt aaaaatattt tttccaggag tgagtgagtt tggaaaggaa     900

tccatccttt ttcattacac agactgggta gatgatcaga gacctgaaaa ctaccgtgag     960

gccttgggtg atgttgttgg ggattataat ttcatatgcc ctgccttgga gttcaccaag    1020

aagttctcag aatggggaaa taatgccttt ttctactatt ttgaacaccg atcctccaaa    1080

cttccgtggc cagaatggat gggagtgatg catggctatg aaatt                    1125
```

```
<210> SEQ ID NO 4
<211> LENGTH: 375
<212> TYPE: PRT
<213> ORGANISM: Artificial
<220> FEATURE:
<223> OTHER INFORMATION: truncated 14-1 mutant (A199S/A328/Y332G) amino
      acid sequence of modified BChE

<400> SEQUENCE: 4

Asn Ile Asp Gln Ser Phe Pro Gly Phe His Gly Ser Glu Met Trp Asn
1               5                   10                  15

Pro Asn Thr Asp Leu Ser Glu Asp Cys Leu Tyr Leu Asn Val Trp Ile
            20                  25                  30

Pro Ala Pro Lys Pro Lys Asn Ala Thr Val Leu Ile Trp Ile Tyr Gly
        35                  40                  45

Gly Gly Phe Gln Thr Gly Thr Ser Ser Leu His Val Tyr Asp Gly Lys
    50                  55                  60

Phe Leu Ala Arg Val Glu Arg Val Ile Val Val Ser Met Asn Tyr Arg
65                  70                  75                  80

Val Gly Ala Leu Gly Phe Leu Ala Leu Pro Gly Asn Pro Glu Ala Pro
                85                  90                  95

Gly Asn Met Gly Leu Phe Asp Gln Gln Leu Ala Leu Gln Trp Val Gln
            100                 105                 110

Lys Asn Ile Ala Ala Phe Gly Gly Asn Pro Lys Ser Val Thr Leu Phe
        115                 120                 125

Gly Glu Ser Ser Gly Ala Ala Ser Val Ser Leu His Leu Leu Ser Pro
    130                 135                 140

Gly Ser His Ser Leu Phe Thr Arg Ala Ile Leu Gln Ser Gly Ser Phe
145                 150                 155                 160

Asn Ala Pro Trp Ala Val Thr Ser Leu Tyr Glu Ala Arg Asn Arg Thr
                165                 170                 175

Leu Asn Leu Ala Lys Leu Thr Gly Cys Ser Arg Glu Asn Glu Thr Glu
            180                 185                 190

Ile Ile Lys Cys Leu Arg Asn Lys Asp Pro Gln Glu Ile Leu Leu Asn
        195                 200                 205

Glu Ala Phe Val Val Pro Tyr Gly Thr Pro Leu Ser Val Asn Phe Gly
    210                 215                 220

Pro Thr Val Asp Gly Asp Phe Leu Thr Asp Met Pro Asp Ile Leu Leu
225                 230                 235                 240

Glu Leu Gly Gln Phe Lys Lys Thr Gln Ile Leu Val Gly Val Asn Lys
                245                 250                 255

Asp Glu Gly Thr Trp Phe Leu Val Gly Gly Ala Pro Gly Phe Ser Lys
            260                 265                 270

Asp Asn Asn Ser Ile Ile Thr Arg Lys Glu Phe Gln Glu Gly Leu Lys
        275                 280                 285
```

-continued

Ile Phe Phe Pro Gly Val Ser Glu Phe Gly Lys Glu Ser Ile Leu Phe
290 295 300

His Tyr Thr Asp Trp Val Asp Asp Gln Arg Pro Glu Asn Tyr Arg Glu
305 310 315 320

Ala Leu Gly Asp Val Val Gly Asp Tyr Asn Phe Ile Cys Pro Ala Leu
325 330 335

Glu Phe Thr Lys Lys Phe Ser Glu Trp Gly Asn Asn Ala Phe Phe Tyr
340 345 350

Tyr Phe Glu His Arg Ser Ser Lys Leu Pro Trp Pro Glu Trp Met Gly
355 360 365

Val Met His Gly Tyr Glu Ile
370 375

<210> SEQ ID NO 5
<211> LENGTH: 966
<212> TYPE: DNA
<213> ORGANISM: Artificial
<220> FEATURE:
<223> OTHER INFORMATION: 14-1 mutant (A199S/A328W/Y332G) BChE nucleic acid sequence corresponding to a.a. residues 117-438

<400> SEQUENCE: 5
ggttttcaaa ctggaacatc atctttacat gtttatgatg gcaagtttct ggctcgggtt 60
gaaagagtta ttgtagtgtc aatgaactat agggtgggtg ccctaggatt cttagctttg 120
ccaggaaatc ctgaggctcc agggaacatg ggtttatttg atcaacagtt ggctcttcag 180
tgggttcaaa aaaatatagc agcctttggt ggaaatccta aaagtgtaac tctctttgga 240
gaaagttccg gagcagcttc agttagcctg catttgcttt ctcctggaag ccattcattg 300
ttcaccagag ccattctgca aagtggttcc tttaatgctc cttgggcggt aacatctctt 360
tatgaagcta ggaacagaac gttgaactta gctaaattga ctggttgctc tagagagaat 420
gagactgaaa taatcaagtg tcttagaaat aaagatcccc aagaaattct tctgaatgaa 480
gcatttgttg tcccctatgg gactcctttg tcagtaaact ttggtccgac cgtggatggt 540
gattttctca ctgacatgcc agacatatta cttgaacttg gacaatttaa aaaaacccag 600
attttggtgg gtgttaataa agatgaaggg acatggtttt tagtcggtgg tgctcctggc 660
ttcagcaaag ataacaatag tatcataact agaaaagaat ttcaggaagg tttaaaaata 720
ttttttccag gagtgagtga gtttggaaag gaatccatcc tttttcatta cacagactgg 780
gtagatgatc agagacctga aaactaccgt gaggccttgg gtgatgttgt tggggattat 840
aatttcatat gccctgcctt ggagttcacc aagaagttct cagaatgggg aaataatgcc 900
tttttctact attttgaaca ccgatcctcc aaacttccgt ggccagaatg gatgggagtg 960
atgcat 966

<210> SEQ ID NO 6
<211> LENGTH: 322
<212> TYPE: PRT
<213> ORGANISM: Artificial
<220> FEATURE:
<223> OTHER INFORMATION: 14-1 mutant (A199S/A328W/Y332G) BChE a.a. residues 117-438

<400> SEQUENCE: 6

Gly Phe Gln Thr Gly Thr Ser Ser Leu His Val Tyr Asp Gly Lys Phe
1 5 10 15

Leu Ala Arg Val Glu Arg Val Ile Val Val Ser Met Asn Tyr Arg Val
20 25 30

```
Gly Ala Leu Gly Phe Leu Ala Leu Pro Gly Asn Pro Glu Ala Pro Gly
        35                  40                  45

Asn Met Gly Leu Phe Asp Gln Gln Leu Ala Leu Gln Trp Val Gln Lys
    50                  55                  60

Asn Ile Ala Ala Phe Gly Gly Asn Pro Lys Ser Val Thr Leu Phe Gly
65                  70                  75                  80

Glu Ser Ser Gly Ala Ala Ser Val Ser Leu His Leu Leu Ser Pro Gly
                85                  90                  95

Ser His Ser Leu Phe Thr Arg Ala Ile Leu Gln Ser Gly Ser Phe Asn
            100                 105                 110

Ala Pro Trp Ala Val Thr Ser Leu Tyr Glu Ala Arg Asn Arg Thr Leu
        115                 120                 125

Asn Leu Ala Lys Leu Thr Gly Cys Ser Arg Glu Asn Glu Thr Glu Ile
    130                 135                 140

Ile Lys Cys Leu Arg Asn Lys Asp Pro Gln Glu Ile Leu Leu Asn Glu
145                 150                 155                 160

Ala Phe Val Val Pro Tyr Gly Thr Pro Leu Ser Val Asn Phe Gly Pro
                165                 170                 175

Thr Val Asp Gly Asp Phe Leu Thr Asp Met Pro Asp Ile Leu Leu Glu
            180                 185                 190

Leu Gly Gln Phe Lys Lys Thr Gln Ile Leu Val Gly Val Asn Lys Asp
        195                 200                 205

Glu Gly Thr Trp Phe Leu Val Gly Gly Ala Pro Gly Phe Ser Lys Asp
    210                 215                 220

Asn Asn Ser Ile Ile Thr Arg Lys Glu Phe Gln Glu Gly Leu Lys Ile
225                 230                 235                 240

Phe Phe Pro Gly Val Ser Glu Phe Gly Lys Glu Ser Ile Leu Phe His
                245                 250                 255

Tyr Thr Asp Trp Val Asp Asp Gln Arg Pro Glu Asn Tyr Arg Glu Ala
            260                 265                 270

Leu Gly Asp Val Val Gly Asp Tyr Asn Phe Ile Cys Pro Ala Leu Glu
        275                 280                 285

Phe Thr Lys Lys Phe Ser Glu Trp Gly Asn Asn Ala Phe Phe Tyr Tyr
    290                 295                 300

Phe Glu His Arg Ser Ser Lys Leu Pro Trp Pro Glu Trp Met Gly Val
305                 310                 315                 320

Met His


<210> SEQ ID NO 7
<211> LENGTH: 1722
<212> TYPE: DNA
<213> ORGANISM: Artificial
<220> FEATURE:
<223> OTHER INFORMATION: 14-2 mutant (A199S/F227A/A328W/Y332G) BChE,
      full nucleic acid sequence

<400> SEQUENCE: 7

gaagatgaca tcataattgc aacaaagaat ggaaaagtca gagggatgaa cttgacagtt      60

tttggtggca cggtaacagc ctttcttgga attccctatg cacagccacc tcttggtaga     120

cttcgattca aaaagccaca gtctctgacc aagtggtctg atatttggaa tgccacaaaa     180

tatgcaaatt cttgctgtca gaacatagat caaagttttc caggcttcca tggatcagag     240

atgtggaacc caaacactga cctcagtgaa gactgtttat atctaaatgt atggattcca     300

gcacctaaac caaaaaatgc cactgtattg atatggattt atggtggtgg ttttcaaact     360
```

-continued

```
ggaacatcat ctttacatgt ttatgatggc aagtttctgg ctcgggttga aagagttatt    420

gtagtgtcaa tgaactatag ggtgggtgcc ctaggattct tagctttgcc aggaaatcct    480

gaggctccag ggaacatggg tttatttgat caacagttgg ctcttcagtg ggttcaaaaa    540

aatatagcag cctttggtgg aaatcctaaa agtgtaactc tctttggaga aagttccgga    600

gcagcttcag ttagcctgca tttgctttct cctggaagcc attcattgtt caccagagcc    660

attctgcaaa gtggttccgc taatgctcct tgggcggtaa catctcttta tgaagctagg    720

aacagaacgt tgaacttagc taaattgact ggttgctcta gagagaatga gactgaaata    780

atcaagtgtc ttagaaataa agatccccaa gaaattcttc tgaatgaagc atttgttgtc    840

ccctatggga ctcctttgtc agtaaacttt ggtccgaccg tggatggtga ttttctcact    900

gacatgccag acatattact tgaacttgga caatttaaaa aaacccagat tttggtgggt    960

gttaataaag atgaagggac atggttttta gtcggtggtg ctcctggctt cagcaaagat   1020

aacaatagta tcataactag aaaagaattt caggaaggtt taaaaatatt ttttccagga   1080

gtgagtgagt ttggaaagga atccatcctt tttcattaca cagactgggt agatgatcag   1140

agacctgaaa actaccgtga ggccttgggt gatgttgttg gggattataa tttcatatgc   1200

cctgccttgg agttcaccaa gaagttctca gaatggggaa ataatgcctt tttctactat   1260

tttgaacacc gatcctccaa acttccgtgg ccagaatgga tgggagtgat gcatggctat   1320

gaaattgaat ttgtctttgg tttacctctg gaaagaagag ataattacac aaaagccgag   1380

gaaattttga gtagatccat agtgaaacgg tgggcaaatt ttgcaaaata tgggaatcca   1440

aatgagactc agaacaatag cacaagctgg cctgtcttca aaagcactga acaaaaatat   1500

ctaaccttga atacagagtc aacaagaata atgacgaaac tacgtgctca acaatgtcga   1560

ttctggacat catttttcc aaaagtcttg gaaatgacag gaaatattga tgaagcagaa   1620

tgggagtgga aagcaggatt ccatcgctgg aacaattaca tgatggactg gaaaaatcaa   1680

tttaacgatt acactagcaa gaaagaaagt tgtgtgggtc tc                      1722
```

```
<210> SEQ ID NO 8
<211> LENGTH: 574
<212> TYPE: PRT
<213> ORGANISM: Artificial
<220> FEATURE:
<223> OTHER INFORMATION: 14-2 mutant (A199S/F227A/A328W/Y332G), full
      amino acid sequence

<400> SEQUENCE: 8

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110
```

-continued

```
Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Ala Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
```

-continued

```
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570


<210> SEQ ID NO 9
<211> LENGTH: 1125
<212> TYPE: DNA
<213> ORGANISM: Artificial
<220> FEATURE:
<223> OTHER INFORMATION: 14-2 mutant (A199/F227A/A328W/Y322G) BChE
      nucleic acid sequence for a.a. residues 68-442

<400> SEQUENCE: 9

aacatagatc aaagttttcc aggcttccat ggatcagaga tgtggaaccc aaacactgac      60

ctcagtgaag actgtttata tctaaatgta tggattccag cacctaaacc aaaaaatgcc     120

actgtattga tatggattta tggtggtggt tttcaaactg gaacatcatc tttacatgtt     180

tatgatggca agtttctggc tcgggttgaa agagttattg tagtgtcaat gaactatagg     240

gtgggtgccc taggattctt agctttgcca ggaaatcctg aggctccagg gaacatgggt     300

ttatttgatc aacagttggc tcttcagtgg gttcaaaaaa atatagcagc ctttggtgga     360

aatcctaaaa gtgtaactct ctttggagaa agttccggag cagcttcagt tagcctgcat     420

ttgctttctc ctggaagcca ttcattgttc accagagcca ttctgcaaag tggttccgct     480

aatgctcctt gggcggtaac atctctttat gaagctagga acagaacgtt gaacttagct     540

aaattgactg gttgctctag agagaatgag actgaaataa tcaagtgtct tagaaataaa     600

gatccccaag aaattcttct gaatgaagca tttgttgtcc cctatgggac tcctttgtca     660

gtaaactttg gtccgaccgt ggatggtgat tttctcactg acatgccaga catattactt     720

gaacttggac aatttaaaaa aacccagatt ttggtgggtg ttaataaaga tgaagggaca     780

tggtttttag tcggtggtgc tcctggcttc agcaaagata acaatagtat cataactaga     840

aaagaatttc aggaaggttt aaaaatattt tttccaggag tgagtgagtt tggaaaggaa     900

tccatccttt ttcattacac agactgggta gatgatcaga gacctgaaaa ctaccgtgag     960

gccttgggtg atgttgttgg ggattataat ttcatatgcc ctgccttgga gttcaccaag    1020

aagttctcag aatggggaaa taatgccttt ttctactatt ttgaacaccg atcctccaaa    1080

cttccgtggc cagaatggat gggagtgatg catggctatg aaatt                    1125


<210> SEQ ID NO 10
<211> LENGTH: 375
<212> TYPE: PRT
<213> ORGANISM: Artificial
<220> FEATURE:
<223> OTHER INFORMATION: 14-2 mutant (A199S/F227A/A328W/Y332G) BChE,
      amino acid sequence for residues 68-442

<400> SEQUENCE: 10

Asn Ile Asp Gln Ser Phe Pro Gly Phe His Gly Ser Glu Met Trp Asn
1               5                   10                  15

Pro Asn Thr Asp Leu Ser Glu Asp Cys Leu Tyr Leu Asn Val Trp Ile
            20                  25                  30

Pro Ala Pro Lys Pro Lys Asn Ala Thr Val Leu Ile Trp Ile Tyr Gly
        35                  40                  45

Gly Gly Phe Gln Thr Gly Thr Ser Ser Leu His Val Tyr Asp Gly Lys
    50                  55                  60
```

-continued

Phe Leu Ala Arg Val Glu Arg Val Ile Val Val Ser Met Asn Tyr Arg
65 70 75 80

Val Gly Ala Leu Gly Phe Leu Ala Leu Pro Gly Asn Pro Glu Ala Pro
85 90 95

Gly Asn Met Gly Leu Phe Asp Gln Gln Leu Ala Leu Gln Trp Val Gln
100 105 110

Lys Asn Ile Ala Ala Phe Gly Gly Asn Pro Lys Ser Val Thr Leu Phe
115 120 125

Gly Glu Ser Ser Gly Ala Ala Ser Val Ser Leu His Leu Leu Ser Pro
130 135 140

Gly Ser His Ser Leu Phe Thr Arg Ala Ile Leu Gln Ser Gly Ser Ala
145 150 155 160

Asn Ala Pro Trp Ala Val Thr Ser Leu Tyr Glu Ala Arg Asn Arg Thr
165 170 175

Leu Asn Leu Ala Lys Leu Thr Gly Cys Ser Arg Glu Asn Glu Thr Glu
180 185 190

Ile Ile Lys Cys Leu Arg Asn Lys Asp Pro Gln Glu Ile Leu Leu Asn
195 200 205

Glu Ala Phe Val Val Pro Tyr Gly Thr Pro Leu Ser Val Asn Phe Gly
210 215 220

Pro Thr Val Asp Gly Asp Phe Leu Thr Asp Met Pro Asp Ile Leu Leu
225 230 235 240

Glu Leu Gly Gln Phe Lys Lys Thr Gln Ile Leu Val Gly Val Asn Lys
245 250 255

Asp Glu Gly Thr Trp Phe Leu Val Gly Gly Ala Pro Gly Phe Ser Lys
260 265 270

Asp Asn Asn Ser Ile Ile Thr Arg Lys Glu Phe Gln Glu Gly Leu Lys
275 280 285

Ile Phe Phe Pro Gly Val Ser Glu Phe Gly Lys Glu Ser Ile Leu Phe
290 295 300

His Tyr Thr Asp Trp Val Asp Asp Gln Arg Pro Glu Asn Tyr Arg Glu
305 310 315 320

Ala Leu Gly Asp Val Val Gly Asp Tyr Asn Phe Ile Cys Pro Ala Leu
325 330 335

Glu Phe Thr Lys Lys Phe Ser Glu Trp Gly Asn Asn Ala Phe Phe Tyr
340 345 350

Tyr Phe Glu His Arg Ser Ser Lys Leu Pro Trp Pro Glu Trp Met Gly
355 360 365

Val Met His Gly Tyr Glu Ile
370 375

<210> SEQ ID NO 11
<211> LENGTH: 966
<212> TYPE: DNA
<213> ORGANISM: Artificial
<220> FEATURE:
<223> OTHER INFORMATION: 14-2 mutant (A199S/F227A/A328W/Y332G) BChE nucleic acid sequence for residues 117-438

<400> SEQUENCE: 11
ggttttcaaa ctggaacatc atctttacat gtttatgatg gcaagtttct ggctcgggtt 60
gaaagagtta ttgtagtgtc aatgaactat agggtgggtg ccctaggatt cttagctttg 120
ccaggaaatc ctgaggctcc agggaacatg ggtttatttg atcaacagtt ggctcttcag 180
tgggttcaaa aaaatatagc agcctttggt ggaaatccta aaagtgtaac tctctttgga 240

```
gaaagttccg gagcagcttc agttagcctg catttgcttt ctcctggaag ccattcattg    300

ttcaccagag ccattctgca aagtggttcc gctaatgctc cttgggcggt aacatctctt    360

tatgaagcta ggaacagaac gttgaactta gctaaattga ctggttgctc tagagagaat    420

gagactgaaa taatcaagtg tcttagaaat aaagatcccc aagaaattct tctgaatgaa    480

gcatttgttg tcccctatgg gactcctttg tcagtaaact ttggtccgac cgtggatggt    540

gattttctca ctgacatgcc agacatatta cttgaacttg gacaatttaa aaaaacccag    600

attttggtgg gtgttaataa agatgaaggg acatggtttt tagtcggtgg tgctcctggc    660

ttcagcaaag ataacaatag tatcataact agaaaagaat ttcaggaagg tttaaaaata    720

ttttttccag gagtgagtga gtttggaaag gaatccatcc tttttcatta cacagactgg    780

gtagatgatc agagacctga aaactaccgt gaggccttgg gtgatgttgt tggggattat    840

aatttcatat gccctgcctt ggagttcacc aagaagttct cagaatgggg aaataatgcc    900

tttttctact attttgaaca ccgatcctcc aaacttccgt ggccagaatg gatgggagtg    960

atgcat                                                               966


<210> SEQ ID NO 12
<211> LENGTH: 322
<212> TYPE: PRT
<213> ORGANISM: Artificial
<220> FEATURE:
<223> OTHER INFORMATION: 14-2 (A199S/F227A/A328W/Y332G) a.a residues
      117-438

<400> SEQUENCE: 12

Gly Phe Gln Thr Gly Thr Ser Ser Leu His Val Tyr Asp Gly Lys Phe
1               5                   10                  15

Leu Ala Arg Val Glu Arg Val Ile Val Val Ser Met Asn Tyr Arg Val
            20                  25                  30

Gly Ala Leu Gly Phe Leu Ala Leu Pro Gly Asn Pro Glu Ala Pro Gly
        35                  40                  45

Asn Met Gly Leu Phe Asp Gln Gln Leu Ala Leu Gln Trp Val Gln Lys
    50                  55                  60

Asn Ile Ala Ala Phe Gly Gly Asn Pro Lys Ser Val Thr Leu Phe Gly
65                  70                  75                  80

Glu Ser Ser Gly Ala Ala Ser Val Ser Leu His Leu Leu Ser Pro Gly
                85                  90                  95

Ser His Ser Leu Phe Thr Arg Ala Ile Leu Gln Ser Gly Ser Ala Asn
            100                 105                 110

Ala Pro Trp Ala Val Thr Ser Leu Tyr Glu Ala Arg Asn Arg Thr Leu
        115                 120                 125

Asn Leu Ala Lys Leu Thr Gly Cys Ser Arg Glu Asn Glu Thr Glu Ile
    130                 135                 140

Ile Lys Cys Leu Arg Asn Lys Asp Pro Gln Glu Ile Leu Leu Asn Glu
145                 150                 155                 160

Ala Phe Val Val Pro Tyr Gly Thr Pro Leu Ser Val Asn Phe Gly Pro
                165                 170                 175

Thr Val Asp Gly Asp Phe Leu Thr Asp Met Pro Asp Ile Leu Leu Glu
            180                 185                 190

Leu Gly Gln Phe Lys Lys Thr Gln Ile Leu Val Gly Val Asn Lys Asp
        195                 200                 205

Glu Gly Thr Trp Phe Leu Val Gly Gly Ala Pro Gly Phe Ser Lys Asp
    210                 215                 220
```

-continued

```
Asn Asn Ser Ile Ile Thr Arg Lys Glu Phe Gln Glu Gly Leu Lys Ile
225                 230                 235                 240

Phe Phe Pro Gly Val Ser Glu Phe Gly Lys Glu Ser Ile Leu Phe His
                245                 250                 255

Tyr Thr Asp Trp Val Asp Asp Gln Arg Pro Glu Asn Tyr Arg Glu Ala
            260                 265                 270

Leu Gly Asp Val Val Gly Asp Tyr Asn Phe Ile Cys Pro Ala Leu Glu
        275                 280                 285

Phe Thr Lys Lys Phe Ser Glu Trp Gly Asn Asn Ala Phe Phe Tyr Tyr
    290                 295                 300

Phe Glu His Arg Ser Ser Lys Leu Pro Trp Pro Glu Trp Met Gly Val
305                 310                 315                 320

Met His


<210> SEQ ID NO 13
<211> LENGTH: 1722
<212> TYPE: DNA
<213> ORGANISM: Artificial
<220> FEATURE:
<223> OTHER INFORMATION: 14-3 mutant (A199S/S287G/A328W/Y332G) BChE
      nucleic acid sequence

<400> SEQUENCE: 13

gaagatgaca tcataattgc aacaaagaat ggaaaagtca gagggatgaa cttgacagtt     60

tttggtggca cggtaacagc ctttcttgga attccctatg cacagccacc tcttggtaga    120

cttcgattca aaaagccaca gtctctgacc aagtggtctg atatttggaa tgccacaaaa    180

tatgcaaatt cttgctgtca gaacatagat caaagttttc caggcttcca tggatcagag    240

atgtggaacc caaacactga cctcagtgaa gactgtttat atctaaatgt atggattcca    300

gcacctaaac caaaaaatgc cactgtattg atatggattt atggtggtgg ttttcaaact    360

ggaacatcat ctttacatgt ttatgatggc aagtttctgg ctcgggttga aagagttatt    420

gtagtgtcaa tgaactatag ggtgggtgcc ctaggattct tagctttgcc aggaaatcct    480

gaggctccag ggaacatggg tttatttgat caacagttgg ctcttcagtg ggttcaaaaa    540

aatatagcag cctttggtgg aaatcctaaa agtgtaactc tctttggaga aagttccgga    600

gcagcttcag ttagcctgca tttgctttct cctggaagcc attcattgtt caccagagcc    660

attctgcaaa gtggttcctt taatgctcct tgggcggtaa catctcttta tgaagctagg    720

aacagaacgt tgaacttagc taaattgact ggttgctcta gagagaatga gactgaaata    780

atcaagtgtc ttagaaataa agatccccaa gaaattcttc tgaatgaagc atttgttgtc    840

ccctatggga ctcctttggg tgtaaacttt ggtccgaccg tggatggtga ttttctcact    900

gacatgccag acatattact tgaacttgga caatttaaaa aaacccagat tttggtgggt    960

gttaataaag atgaagggac atggttttta gtcggtggtg ctcctggctt cagcaaagat   1020

aacaatagta tcataactag aaaagaattt caggaaggtt taaaaatatt ttttccagga   1080

gtgagtgagt ttggaaagga atccatcctt tttcattaca cagactgggt agatgatcag   1140

agacctgaaa actaccgtga ggccttgggt gatgttgttg gggattataa tttcatatgc   1200

cctgccttgg agttcaccaa gaagttctca gaatggggaa ataatgcctt tttctactat   1260

tttgaacacc gatcctccaa acttccgtgg ccagaatgga tgggagtgat gcatggctat   1320

gaaattgaat ttgtctttgg tttacctctg gaaagaagag ataattacac aaaagccgag   1380

gaaattttga gtagatccat agtgaaacgg tggcaaattt ttgcaaaata tgggaatcca   1440
```

-continued

```
aatgagactc agaacaatag cacaagctgg cctgtcttca aaagcactga acaaaaatat   1500

ctaaccttga atacagagtc aacaagaata atgacgaaac tacgtgctca acaatgtcga   1560

ttctggacat catttttttcc aaaagtcttg gaaatgacag gaaatattga tgaagcagaa   1620

tgggagtgga aagcaggatt ccatcgctgg aacaattaca tgatggactg gaaaaatcaa   1680

tttaacgatt acactagcaa gaaagaaagt tgtgtgggtc tc                       1722


<210> SEQ ID NO 14
<211> LENGTH: 574
<212> TYPE: PRT
<213> ORGANISM: Artificial
<220> FEATURE:
<223> OTHER INFORMATION: 14-3 mutant (A199S/S287G/A328W/Y332G) BChE
      amino acid sequence

<400> SEQUENCE: 14

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Gly Val
        275                 280                 285

Asn Phe Gly Pro Thr Val Asp Gly Asp Phe Leu Thr Asp Met Pro Asp
    290                 295                 300
```

-continued

```
Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570
```

<210> SEQ ID NO 15
<211> LENGTH: 1125
<212> TYPE: DNA
<213> ORGANISM: Artificial
<220> FEATURE:
<223> OTHER INFORMATION: 14-3 mutant (A199S/S287G/A328W/Y332G) BChE nucleic acid sequence for amino acid residues 68-442

<400> SEQUENCE: 15

```
aacatagatc aaagttttcc aggcttccat ggatcagaga tgtggaaccc aaacactgac     60

ctcagtgaag actgtttata tctaaatgta tggattccag cacctaaacc aaaaaatgcc    120

actgtattga tatggattta tggtggtggt tttcaaactg gaacatcatc tttacatgtt    180

tatgatggca agtttctggc tcgggttgaa agagttattg tagtgtcaat gaactatagg    240

gtgggtgccc taggattctt agctttgcca ggaaatcctg aggctccagg gaacatgggt    300

ttatttgatc aacagttggc tcttcagtgg gttcaaaaaa atatagcagc ctttggtgga    360

aatcctaaaa gtgtaactct ctttggagaa agttccggag cagcttcagt tagcctgcat    420

ttgctttctc ctggaagcca ttcattgttc accagagcca ttctgcaaag tggttccttt    480

aatgctcctt gggcggtaac atctctttat gaagctagga acagaacgtt gaacttagct    540
```

```
aaattgactg gttgctctag agagaatgag actgaaataa tcaagtgtct tagaaataaa    600

gatccccaag aaattcttct gaatgaagca tttgttgtcc cctatgggac tcctttgggt    660

gtaaactttg gtccgaccgt ggatggtgat ttctcactg acatgccaga catattactt     720

gaacttggac aatttaaaaa aacccagatt ttggtgggtg ttaataaaga tgaagggaca    780

tggtttttag tcggtggtgc tcctggcttc agcaaagata acaatagtat cataactaga    840

aaagaatttc aggaaggttt aaaaaatattt tttccaggag tgagtgagtt tggaaaggaa    900

tccatccttt ttcattacac agactgggta gatgatcaga gacctgaaaa ctaccgtgag    960

gccttgggtg atgttgttgg ggattataat ttcatatgcc ctgccttgga gttcaccaag   1020

aagttctcag aatggggaaa taatgccttt ttctactatt ttgaacaccg atcctccaaa   1080

cttccgtggc cagaatggat gggagtgatg catggctatg aaatt                   1125
```

```
<210> SEQ ID NO 16
<211> LENGTH: 375
<212> TYPE: PRT
<213> ORGANISM: Artificial
<220> FEATURE:
<223> OTHER INFORMATION: 14-3 mutant (A199S/S287G/A328W/Y332G) BChE
      amino acid sequence for residues 68-442

<400> SEQUENCE: 16

Asn Ile Asp Gln Ser Phe Pro Gly Phe His Gly Ser Glu Met Trp Asn
1               5                   10                  15

Pro Asn Thr Asp Leu Ser Glu Asp Cys Leu Tyr Leu Asn Val Trp Ile
            20                  25                  30

Pro Ala Pro Lys Pro Lys Asn Ala Thr Val Leu Ile Trp Ile Tyr Gly
        35                  40                  45

Gly Gly Phe Gln Thr Gly Thr Ser Ser Leu His Val Tyr Asp Gly Lys
    50                  55                  60

Phe Leu Ala Arg Val Glu Arg Val Ile Val Val Ser Met Asn Tyr Arg
65                  70                  75                  80

Val Gly Ala Leu Gly Phe Leu Ala Leu Pro Gly Asn Pro Glu Ala Pro
                85                  90                  95

Gly Asn Met Gly Leu Phe Asp Gln Gln Leu Ala Leu Gln Trp Val Gln
            100                 105                 110

Lys Asn Ile Ala Ala Phe Gly Gly Asn Pro Lys Ser Val Thr Leu Phe
        115                 120                 125

Gly Glu Ser Ser Gly Ala Ala Ser Val Ser Leu His Leu Leu Ser Pro
    130                 135                 140

Gly Ser His Ser Leu Phe Thr Arg Ala Ile Leu Gln Ser Gly Ser Phe
145                 150                 155                 160

Asn Ala Pro Trp Ala Val Thr Ser Leu Tyr Glu Ala Arg Asn Arg Thr
                165                 170                 175

Leu Asn Leu Ala Lys Leu Thr Gly Cys Ser Arg Glu Asn Glu Thr Glu
            180                 185                 190

Ile Ile Lys Cys Leu Arg Asn Lys Asp Pro Gln Glu Ile Leu Leu Asn
        195                 200                 205

Glu Ala Phe Val Val Pro Tyr Gly Thr Pro Leu Gly Val Asn Phe Gly
    210                 215                 220

Pro Thr Val Asp Gly Asp Phe Leu Thr Asp Met Pro Asp Ile Leu Leu
225                 230                 235                 240

Glu Leu Gly Gln Phe Lys Lys Thr Gln Ile Leu Val Gly Val Asn Lys
                245                 250                 255
```

```
Asp Glu Gly Thr Trp Phe Leu Val Gly Gly Ala Pro Gly Phe Ser Lys
            260                 265                 270

Asp Asn Asn Ser Ile Ile Thr Arg Lys Glu Phe Gln Glu Gly Leu Lys
        275                 280                 285

Ile Phe Phe Pro Gly Val Ser Glu Phe Gly Lys Glu Ser Ile Leu Phe
    290                 295                 300

His Tyr Thr Asp Trp Val Asp Asp Gln Arg Pro Glu Asn Tyr Arg Glu
305                 310                 315                 320

Ala Leu Gly Asp Val Val Gly Asp Tyr Asn Phe Ile Cys Pro Ala Leu
                325                 330                 335

Glu Phe Thr Lys Lys Phe Ser Glu Trp Gly Asn Asn Ala Phe Phe Tyr
            340                 345                 350

Tyr Phe Glu His Arg Ser Ser Lys Leu Pro Trp Pro Glu Trp Met Gly
        355                 360                 365

Val Met His Gly Tyr Glu Ile
    370                 375
```

<210> SEQ ID NO 17
<211> LENGTH: 966
<212> TYPE: DNA
<213> ORGANISM: Artificial
<220> FEATURE:
<223> OTHER INFORMATION: 14-3 mutant (A199S/S287G/A328W/Y332G) BChE nucleic acid sequence for amino acid residues 117-438

<400> SEQUENCE: 17

```
ggttttcaaa ctggaacatc atctttacat gtttatgatg gcaagtttct ggctcgggtt     60

gaaagagtta ttgtagtgtc aatgaactat agggtgggtg ccctaggatt cttagctttg    120

ccaggaaatc ctgaggctcc agggaacatg ggtttatttg atcaacagtt ggctcttcag    180

tgggttcaaa aaaatatagc agcctttggt ggaaatccta aaagtgtaac tctctttgga    240

gaaagttccg gagcagcttc agttagcctg catttgcttt ctcctggaag ccattcattg    300

ttcaccagag ccattctgca aagtggttcc tttaatgctc cttgggcggt aacatctctt    360

tatgaagcta ggaacagaac gttgaactta gctaaattga ctggttgctc tagagagaat    420

gagactgaaa taatcaagtg tcttagaaat aaagatcccc aagaaattct tctgaatgaa    480

gcatttgttg tcccctatgg gactcctttg ggtgtaaact ttggtccgac cgtggatggt    540

gattttctca ctgacatgcc agacatatta cttgaacttg gacaatttaa aaaaacccag    600

attttggtgg gtgttaataa agatgaaggg acatggtttt tagtcggtgg tgctcctggc    660

ttcagcaaag ataacaatag tatcataact agaaaagaat ttcaggaagg tttaaaaata    720

ttttttccag gagtgagtga gtttggaaag gaatccatcc tttttcatta cacagactgg    780

gtagatgatc agagacctga aaactaccgt gaggccttgg gtgatgttgt tggggattat    840

aatttcatat gccctgcctt ggagttcacc aagaagttct cagaatgggg aaataatgcc    900

tttttctact attttgaaca ccgatcctcc aaacttccgt ggccagaatg gatgggagtg    960

atgcat                                                               966
```

<210> SEQ ID NO 18
<211> LENGTH: 322
<212> TYPE: PRT
<213> ORGANISM: Artificial
<220> FEATURE:
<223> OTHER INFORMATION: 14-3 mutant (A199S/S287G/A328W/Y332G) BChE amino acid sequence for residues 117-438

<400> SEQUENCE: 18

```
Gly Phe Gln Thr Gly Thr Ser Ser Leu His Val Tyr Asp Gly Lys Phe
1               5                   10                  15

Leu Ala Arg Val Glu Arg Val Ile Val Val Ser Met Asn Tyr Arg Val
            20                  25                  30

Gly Ala Leu Gly Phe Leu Ala Leu Pro Gly Asn Pro Glu Ala Pro Gly
        35                  40                  45

Asn Met Gly Leu Phe Asp Gln Gln Leu Ala Leu Gln Trp Val Gln Lys
    50                  55                  60

Asn Ile Ala Ala Phe Gly Gly Asn Pro Lys Ser Val Thr Leu Phe Gly
65                  70                  75                  80

Glu Ser Ser Gly Ala Ala Ser Val Ser Leu His Leu Leu Ser Pro Gly
                85                  90                  95

Ser His Ser Leu Phe Thr Arg Ala Ile Leu Gln Ser Gly Ser Phe Asn
            100                 105                 110

Ala Pro Trp Ala Val Thr Ser Leu Tyr Glu Ala Arg Asn Arg Thr Leu
        115                 120                 125

Asn Leu Ala Lys Leu Thr Gly Cys Ser Arg Glu Asn Glu Thr Glu Ile
    130                 135                 140

Ile Lys Cys Leu Arg Asn Lys Asp Pro Gln Glu Ile Leu Leu Asn Glu
145                 150                 155                 160

Ala Phe Val Val Pro Tyr Gly Thr Pro Leu Gly Val Asn Phe Gly Pro
                165                 170                 175

Thr Val Asp Gly Asp Phe Leu Thr Asp Met Pro Asp Ile Leu Leu Glu
            180                 185                 190

Leu Gly Gln Phe Lys Lys Thr Gln Ile Leu Val Gly Val Asn Lys Asp
        195                 200                 205

Glu Gly Thr Trp Phe Leu Val Gly Gly Ala Pro Gly Phe Ser Lys Asp
    210                 215                 220

Asn Asn Ser Ile Ile Thr Arg Lys Glu Phe Gln Glu Gly Leu Lys Ile
225                 230                 235                 240

Phe Phe Pro Gly Val Ser Glu Phe Gly Lys Glu Ser Ile Leu Phe His
                245                 250                 255

Tyr Thr Asp Trp Val Asp Asp Gln Arg Pro Glu Asn Tyr Arg Glu Ala
            260                 265                 270

Leu Gly Asp Val Val Gly Asp Tyr Asn Phe Ile Cys Pro Ala Leu Glu
        275                 280                 285

Phe Thr Lys Lys Phe Ser Glu Trp Gly Asn Asn Ala Phe Phe Tyr Tyr
    290                 295                 300

Phe Glu His Arg Ser Ser Lys Leu Pro Trp Pro Glu Trp Met Gly Val
305                 310                 315                 320

Met His
```

<210> SEQ ID NO 19
<211> LENGTH: 1722
<212> TYPE: DNA
<213> ORGANISM: Artificial
<220> FEATURE:
<223> OTHER INFORMATION: 12-7 mutant (A199S/F227A/S287G/A328W/Y332G)
      BChE nucleic acid sequence

<400> SEQUENCE: 19

```
gaagatgaca tcataattgc aacaaagaat ggaaaagtca gagggatgaa cttgacagtt      60

tttggtggca cggtaacagc ctttcttgga attccctatg cacagccacc tcttggtaga     120
```

-continued

```
cttcgattca aaaagccaca gtctctgacc aagtggtctg atatttggaa tgccacaaaa    180

tatgcaaatt cttgctgtca gaacatagat caaagttttc caggcttcca tggatcagag    240

atgtggaacc caaacactga cctcagtgaa gactgtttat atctaaatgt atggattcca    300

gcacctaaac caaaaaatgc cactgtattg atatggattt atggtggtgg ttttcaaact    360

ggaacatcat ctttacatgt ttatgatggc aagtttctgg ctcgggttga aagagttatt    420

gtagtgtcaa tgaactatag ggtgggtgcc ctaggattct tagctttgcc aggaaatcct    480

gaggctccag ggaacatggg tttatttgat caacagttgg ctcttcagtg ggttcaaaaa    540

aatatagcag cctttggtgg aaatcctaaa agtgtaactc tctttggaga aagttccgga    600

gcagcttcag ttagcctgca tttgctttct cctggaagcc attcattgtt caccagagcc    660

attctgcaaa gtggttccgc taatgctcct tgggcggtaa catctcttta tgaagctagg    720

aacagaacgt tgaacttagc taaattgact ggttgctcta gagagaatga gactgaaata    780

atcaagtgtc ttagaaataa agatccccaa gaaattcttc tgaatgaagc atttgttgtc    840

ccctatggga ctcctttggg tgtaaacttt ggtccgaccg tggatggtga ttttctcact    900

gacatgccag acatattact tgaacttgga caatttaaaa aaacccagat tttggtgggt    960

gttaataaag atgaagggac atggttttta gtcggtggtg ctcctggctt cagcaaagat   1020

aacaatagta tcataactag aaaagaattt caggaaggtt taaaaatatt ttttccagga   1080

gtgagtgagt ttggaaagga atccatcctt tttcattaca cagactgggt agatgatcag   1140

agacctgaaa actaccgtga ggccttgggt gatgttgttg gggattataa tttcatatgc   1200

cctgccttgg agttcaccaa gaagttctca gaatggggaa ataatgcctt tttctactat   1260

tttgaacacc gatcctccaa acttccgtgg ccagaatgga tgggagtgat gcatggctat   1320

gaaattgaat ttgtctttgg tttacctctg gaaagaagag ataattacac aaaagccgag   1380

gaaattttga gtagatccat agtgaaacgg tgggcaaatt ttgcaaaata tgggaatcca   1440

aatgagactc agaacaatag cacaagctgg cctgtcttca aaagcactga acaaaaatat   1500

ctaaccttga atacagagtc aacaagaata atgacgaaac tacgtgctca acaatgtcga   1560

ttctggacat catttttcc aaaagtcttg gaaatgacag gaaatattga tgaagcagaa   1620

tgggagtgga aagcaggatt ccatcgctgg aacaattaca tgatggactg gaaaaatcaa   1680

tttaacgatt acactagcaa gaaagaaagt tgtgtgggtc tc                       1722
```

<210> SEQ ID NO 20
<211> LENGTH: 574
<212> TYPE: PRT
<213> ORGANISM: Artificial
<220> FEATURE:
<223> OTHER INFORMATION: 12-7 mutant (A199S/F227A/S287G/A328W/Y332G) BChE amino acid sequence

<400> SEQUENCE: 20

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80
```

-continued

```
Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Ala Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Gly Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495
```

-continued

```
Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570


<210> SEQ ID NO 21
<211> LENGTH: 1125
<212> TYPE: DNA
<213> ORGANISM: Artificial
<220> FEATURE:
<223> OTHER INFORMATION: 12-7 mutant (A199S/F227A/S287G/A328W/Y332G)
      BChE nucleic acid sequence for amino acid residues 68-442

<400> SEQUENCE: 21

aacatagatc aaagttttcc aggcttccat ggatcagaga tgtggaaccc aaacactgac     60

ctcagtgaag actgtttata tctaaatgta tggattccag cacctaaacc aaaaaatgcc    120

actgtattga tatggattta tggtggtggt tttcaaactg gaacatcatc tttacatgtt    180

tatgatggca agtttctggc tcgggttgaa agagttattg tagtgtcaat gaactatagg    240

gtgggtgccc taggattctt agctttgcca ggaaatcctg aggctccagg gaacatgggt    300

ttatttgatc aacagttggc tcttcagtgg gttcaaaaaa atatagcagc ctttggtgga    360

aatcctaaaa gtgtaactct ctttggagaa agttccggag cagcttcagt tagcctgcat    420

ttgctttctc ctggaagcca ttcattgttc accagagcca ttctgcaaag tggttccgct    480

aatgctcctt gggcggtaac atctctttat gaagctagga acagaacgtt gaacttagct    540

aaattgactg gttgctctag agagaatgag actgaaataa tcaagtgtct tagaaataaa    600

gatccccaag aaattcttct gaatgaagca tttgttgtcc cctatgggac tcctttgggt    660

gtaaactttg gtccgaccgt ggatggtgat tttctcactg acatgccaga catattactt    720

gaacttggac aatttaaaaa aacccagatt ttggtgggtg ttaataaaga tgaagggaca    780

tggtttttag tcggtggtgc tcctggcttc agcaaagata acaatagtat cataactaga    840

aaagaatttc aggaaggttt aaaaatattt tttccaggag tgagtgagtt tggaaaggaa    900

tccatccttt ttcattacac agactgggta gatgatcaga gacctgaaaa ctaccgtgag    960

gccttgggtg atgttgttgg ggattataat ttcatatgcc ctgccttgga gttcaccaag   1020

aagttctcag aatggggaaa taatgccttt ttctactatt ttgaacaccg atcctccaaa   1080

cttccgtggc cagaatggat gggagtgatg catggctatg aaatt                   1125


<210> SEQ ID NO 22
<211> LENGTH: 375
<212> TYPE: PRT
<213> ORGANISM: Artificial
<220> FEATURE:
<223> OTHER INFORMATION: 12-7 mutant (A199S/F227A/S287G/A328W/Y332G)
      BChE amino acid sequence for residues 68-442

<400> SEQUENCE: 22

Asn Ile Asp Gln Ser Phe Pro Gly Phe His Gly Ser Glu Met Trp Asn
1               5                   10                  15

Pro Asn Thr Asp Leu Ser Glu Asp Cys Leu Tyr Leu Asn Val Trp Ile
```

-continued

```
            20                  25                  30

Pro Ala Pro Lys Pro Lys Asn Ala Thr Val Leu Ile Trp Ile Tyr Gly
        35                  40                  45

Gly Gly Phe Gln Thr Gly Thr Ser Ser Leu His Val Tyr Asp Gly Lys
    50                  55                  60

Phe Leu Ala Arg Val Glu Arg Val Ile Val Val Ser Met Asn Tyr Arg
65                  70                  75                  80

Val Gly Ala Leu Gly Phe Leu Ala Leu Pro Gly Asn Pro Glu Ala Pro
                85                  90                  95

Gly Asn Met Gly Leu Phe Asp Gln Gln Leu Ala Leu Gln Trp Val Gln
            100                 105                 110

Lys Asn Ile Ala Ala Phe Gly Gly Asn Pro Lys Ser Val Thr Leu Phe
        115                 120                 125

Gly Glu Ser Ser Gly Ala Ala Ser Val Ser Leu His Leu Leu Ser Pro
    130                 135                 140

Gly Ser His Ser Leu Phe Thr Arg Ala Ile Leu Gln Ser Gly Ser Ala
145                 150                 155                 160

Asn Ala Pro Trp Ala Val Thr Ser Leu Tyr Glu Ala Arg Asn Arg Thr
                165                 170                 175

Leu Asn Leu Ala Lys Leu Thr Gly Cys Ser Arg Glu Asn Glu Thr Glu
            180                 185                 190

Ile Ile Lys Cys Leu Arg Asn Lys Asp Pro Gln Glu Ile Leu Leu Asn
        195                 200                 205

Glu Ala Phe Val Val Pro Tyr Gly Thr Pro Leu Gly Val Asn Phe Gly
    210                 215                 220

Pro Thr Val Asp Gly Asp Phe Leu Thr Asp Met Pro Asp Ile Leu Leu
225                 230                 235                 240

Glu Leu Gly Gln Phe Lys Lys Thr Gln Ile Leu Val Gly Val Asn Lys
                245                 250                 255

Asp Glu Gly Thr Trp Phe Leu Val Gly Gly Ala Pro Gly Phe Ser Lys
            260                 265                 270

Asp Asn Asn Ser Ile Ile Thr Arg Lys Glu Phe Gln Glu Gly Leu Lys
        275                 280                 285

Ile Phe Phe Pro Gly Val Ser Glu Phe Gly Lys Glu Ser Ile Leu Phe
    290                 295                 300

His Tyr Thr Asp Trp Val Asp Asp Gln Arg Pro Glu Asn Tyr Arg Glu
305                 310                 315                 320

Ala Leu Gly Asp Val Val Gly Asp Tyr Asn Phe Ile Cys Pro Ala Leu
                325                 330                 335

Glu Phe Thr Lys Lys Phe Ser Glu Trp Gly Asn Asn Ala Phe Phe Tyr
            340                 345                 350

Tyr Phe Glu His Arg Ser Ser Lys Leu Pro Trp Pro Glu Trp Met Gly
        355                 360                 365

Val Met His Gly Tyr Glu Ile
    370                 375


<210> SEQ ID NO 23
<211> LENGTH: 966
<212> TYPE: DNA
<213> ORGANISM: Artificial
<220> FEATURE:
<223> OTHER INFORMATION: 12-7 mutant (A199S/F227A/S287G/A328W/Y332G)
      BChE nucleic acid sequence for amino acid residues 117-438

<400> SEQUENCE: 23
```

-continued

```
ggttttcaaa ctggaacatc atctttacat gtttatgatg gcaagtttct ggctcgggtt      60

gaaagagtta ttgtagtgtc aatgaactat agggtgggtg ccctaggatt cttagctttg     120

ccaggaaatc ctgaggctcc agggaacatg ggtttatttg atcaacagtt ggctcttcag     180

tgggttcaaa aaaatatagc agcctttggt ggaaatccta aaagtgtaac tctctttgga     240

gaaagttccg gagcagcttc agttagcctg catttgcttt ctcctggaag ccattcattg     300

ttcaccagag ccattctgca aagtggttcc gctaatgctc cttgggcggt aacatctctt     360

tatgaagcta ggaacagaac gttgaactta gctaaattga ctggttgctc tagagagaat     420

gagactgaaa taatcaagtg tcttagaaat aaagatcccc aagaaattct tctgaatgaa     480

gcatttgttg tcccctatgg gactcctttg ggtgtaaact ttggtccgac cgtggatggt     540

gattttctca ctgacatgcc agacatatta cttgaacttg gacaatttaa aaaaacccag     600

attttggtgg gtgttaataa agatgaaggg acatggtttt tagtcggtgg tgctcctggc     660

ttcagcaaag ataacaatag tatcataact agaaaagaat ttcaggaagg tttaaaaata     720

tttttccag gagtgagtga gtttggaaag gaatccatcc tttttcatta cacagactgg      780

gtagatgatc agagacctga aaactaccgt gaggccttgg gtgatgttgt tggggattat     840

aatttcatat gccctgcctt ggagttcacc aagaagttct cagaatgggg aaataatgcc     900

tttttctact attttgaaca ccgatcctcc aaacttccgt ggccagaatg gatgggagtg     960

atgcat                                                                966
```

<210> SEQ ID NO 24
<211> LENGTH: 322
<212> TYPE: PRT
<213> ORGANISM: Artificial
<220> FEATURE:
<223> OTHER INFORMATION: 12-7 mutant (A199S/F227A/S287G/A328W/Y332G) BChE amino acid sequence for residues 117-438

<400> SEQUENCE: 24

```
Gly Phe Gln Thr Gly Thr Ser Ser Leu His Val Tyr Asp Gly Lys Phe
1               5                   10                  15

Leu Ala Arg Val Glu Arg Val Ile Val Val Ser Met Asn Tyr Arg Val
            20                  25                  30

Gly Ala Leu Gly Phe Leu Ala Leu Pro Gly Asn Pro Glu Ala Pro Gly
        35                  40                  45

Asn Met Gly Leu Phe Asp Gln Gln Leu Ala Leu Gln Trp Val Gln Lys
    50                  55                  60

Asn Ile Ala Ala Phe Gly Gly Asn Pro Lys Ser Val Thr Leu Phe Gly
65                  70                  75                  80

Glu Ser Ser Gly Ala Ala Ser Val Ser Leu His Leu Leu Ser Pro Gly
                85                  90                  95

Ser His Ser Leu Phe Thr Arg Ala Ile Leu Gln Ser Gly Ser Ala Asn
            100                 105                 110

Ala Pro Trp Ala Val Thr Ser Leu Tyr Glu Ala Arg Asn Arg Thr Leu
        115                 120                 125

Asn Leu Ala Lys Leu Thr Gly Cys Ser Arg Glu Asn Glu Thr Glu Ile
    130                 135                 140

Ile Lys Cys Leu Arg Asn Lys Asp Pro Gln Glu Ile Leu Leu Asn Glu
145                 150                 155                 160

Ala Phe Val Val Pro Tyr Gly Thr Pro Leu Gly Val Asn Phe Gly Pro
                165                 170                 175

Thr Val Asp Gly Asp Phe Leu Thr Asp Met Pro Asp Ile Leu Leu Glu
```

-continued

```
            180                 185                 190

Leu Gly Gln Phe Lys Lys Thr Gln Ile Leu Val Gly Val Asn Lys Asp
        195                 200                 205

Glu Gly Thr Trp Phe Leu Val Gly Gly Ala Pro Gly Phe Ser Lys Asp
    210                 215                 220

Asn Asn Ser Ile Ile Thr Arg Lys Glu Phe Gln Glu Gly Leu Lys Ile
225                 230                 235                 240

Phe Phe Pro Gly Val Ser Glu Phe Gly Lys Glu Ser Ile Leu Phe His
                245                 250                 255

Tyr Thr Asp Trp Val Asp Asp Gln Arg Pro Glu Asn Tyr Arg Glu Ala
            260                 265                 270

Leu Gly Asp Val Val Gly Asp Tyr Asn Phe Ile Cys Pro Ala Leu Glu
        275                 280                 285

Phe Thr Lys Lys Phe Ser Glu Trp Gly Asn Asn Ala Phe Phe Tyr Tyr
    290                 295                 300

Phe Glu His Arg Ser Ser Lys Leu Pro Trp Pro Glu Trp Met Gly Val
305                 310                 315                 320

Met His
```

```
<210> SEQ ID NO 25
<211> LENGTH: 1722
<212> TYPE: DNA
<213> ORGANISM: Artificial
<220> FEATURE:
<223> OTHER INFORMATION: 12-4 mutant (A199S/F227A/S287G/A328W/E441D)
      BChe nucleic acid sequence

<400> SEQUENCE: 25

gaagatgaca tcataattgc aacaaagaat ggaaaagtca gagggatgaa cttgacagtt     60

tttggtggca cggtaacagc ctttcttgga attccctatg cacagccacc tcttggtaga    120

cttcgattca aaaagccaca gtctctgacc aagtggtctg atatttggaa tgccacaaaa    180

tatgcaaatt cttgctgtca gaacatagat caaagttttc caggcttcca tggatcagag    240

atgtggaacc caaacactga cctcagtgaa gactgtttat atctaaatgt atggattcca    300

gcacctaaac caaaaaatgc cactgtattg atatggattt atggtggtgg ttttcaaact    360

ggaacatcat ctttacatgt ttatgatggc aagtttctgg ctcgggttga aagagttatt    420

gtagtgtcaa tgaactatag ggtgggtgcc ctaggattct tagctttgcc aggaaatcct    480

gaggctccag ggaacatggg tttatttgat caacagttgg ctcttcagtg ggttcaaaaa    540

aatatagcag cctttggtgg aaatcctaaa agtgtaactc tctttggaga aagttccgga    600

gcagcttcag ttagcctgca tttgctttct cctggaagcc attcattgtt caccagagcc    660

attctgcaaa gtggttccgc taatgctcct tgggcggtaa catctcttta tgaagctagg    720

aacagaacgt tgaacttagc taaattgact ggttgctcta gagagaatga gactgaaata    780

atcaagtgtc ttagaaataa agatccccaa gaaattcttc tgaatgaagc atttgttgtc    840

ccctatggga ctcctttggg tgtaaacttt ggtccgaccg tggatggtga ttttctcact    900

gacatgccag acatattact tgaacttgga caatttaaaa aaacccagat tttggtgggt    960

gttaataaag atgaagggac atggttttta gtctatggtg ctcctggctt cagcaaagat   1020

aacaatagta tcataactag aaaagaattt caggaaggtt taaaaatatt ttttccagga   1080

gtgagtgagt ttggaaagga atccatcctt tttcattaca cagactgggt agatgatcag   1140

agacctgaaa actaccgtga ggccttgggt gatgttgttg gggattataa tttcatatgc   1200
```

-continued

```
cctgccttgg agttcaccaa gaagttctca gaatggggaa ataatgcctt tttctactat   1260

tttgaacacc gatcctccaa acttccgtgg ccagaatgga tgggagtgat gcatggctat   1320

gacattgaat ttgtctttgg tttacctctg gaaagaagag ataattacac aaaagccgag   1380

gaaattttga gtagatccat agtgaaacgg tgggcaaatt ttgcaaaata tgggaatcca   1440

aatgagactc agaacaatag cacaagctgg cctgtcttca aaagcactga acaaaaatat   1500

ctaaccttga atacagagtc aacaagaata atgacgaaac tacgtgctca acaatgtcga   1560

ttctggacat catttttcc aaaagtcttg gaaatgacag gaaatattga tgaagcagaa   1620

tgggagtgga aagcaggatt ccatcgctgg aacaattaca tgatggactg gaaaaatcaa   1680

tttaacgatt acactagcaa gaaagaaagt tgtgtgggtc tc                      1722
```

```
<210> SEQ ID NO 26
<211> LENGTH: 574
<212> TYPE: PRT
<213> ORGANISM: Artificial
<220> FEATURE:
<223> OTHER INFORMATION: 12-4 mutant (A199S/F227A/S287G/A328W/E441D)
      BChe amino acid sequence

<400> SEQUENCE: 26

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Ala Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270
```

```
Leu Leu Asn Glu Ala Phe Val Val Pro Tyr Gly Thr Pro Leu Gly Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Asp Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570


<210> SEQ ID NO 27
<211> LENGTH: 1125
<212> TYPE: DNA
<213> ORGANISM: Artificial
<220> FEATURE:
<223> OTHER INFORMATION: 12-4 mutant (A199S/F227A/S287G/A328W/E441D)
      BChE nucleic acid sequence for amino acid residues 68-442

<400> SEQUENCE: 27

aacatagatc aaagttttcc aggcttccat ggatcagaga tgtggaaccc aaacactgac      60

ctcagtgaag actgtttata tctaaatgta tggattccag cacctaaacc aaaaaatgcc     120

actgtattga tatggattta tggtggtggt tttcaaactg gaacatcatc tttacatgtt     180

tatgatggca agtttctggc tcgggttgaa agagttattg tagtgtcaat gaactatagg     240
```

```
gtgggtgccc taggattctt agctttgcca ggaaatcctg aggctccagg gaacatgggt    300

ttatttgatc aacagttggc tcttcagtgg gttcaaaaaa atatagcagc ctttggtgga    360

aatcctaaaa gtgtaactct ctttggagaa agttccggag cagcttcagt tagcctgcat    420

ttgctttctc ctggaagcca ttcattgttc accagagcca ttctgcaaag tggttccgct    480

aatgctcctt gggcggtaac atctctttat gaagctagga acagaacgtt gaacttagct    540

aaattgactg gttgctctag agagaatgag actgaaataa tcaagtgtct tagaaataaa    600

gatccccaag aaattcttct gaatgaagca tttgttgtcc cctatgggac tcctttgggt    660

gtaaactttg gtccgaccgt ggatggtgat tttctcactg acatgccaga catattactt    720

gaacttggac aatttaaaaa aacccagatt ttggtgggtg ttaataaaga tgaagggaca    780

tggtttttag tctatggtgc tcctggcttc agcaaagata acaatagtat cataactaga    840

aaagaatttc aggaaggttt aaaaatattt tttccaggag tgagtgagtt tggaaaggaa    900

tccatccttt ttcattacac agactgggta gatgatcaga gacctgaaaa ctaccgtgag    960

gccttgggtg atgttgttgg ggattataat ttcatatgcc ctgccttgga gttcaccaag   1020

aagttctcag aatggggaaa taatgccttt ttctactatt ttgaacaccg atcctccaaa   1080

cttccgtggc cagaatggat gggagtgatg catggctatg acatt                   1125

<210> SEQ ID NO 28
<211> LENGTH: 375
<212> TYPE: PRT
<213> ORGANISM: Artificial
<220> FEATURE:
<223> OTHER INFORMATION: 12-4 mutant (A199S/F227A/S287G/A328W/E441D)
      BChE amino acid sequence for residues 68-442

<400> SEQUENCE: 28

Asn Ile Asp Gln Ser Phe Pro Gly Phe His Gly Ser Glu Met Trp Asn
1               5                   10                  15

Pro Asn Thr Asp Leu Ser Glu Asp Cys Leu Tyr Leu Asn Val Trp Ile
            20                  25                  30

Pro Ala Pro Lys Pro Lys Asn Ala Thr Val Leu Ile Trp Ile Tyr Gly
        35                  40                  45

Gly Gly Phe Gln Thr Gly Thr Ser Ser Leu His Val Tyr Asp Gly Lys
    50                  55                  60

Phe Leu Ala Arg Val Glu Arg Val Ile Val Val Ser Met Asn Tyr Arg
65                  70                  75                  80

Val Gly Ala Leu Gly Phe Leu Ala Leu Pro Gly Asn Pro Glu Ala Pro
                85                  90                  95

Gly Asn Met Gly Leu Phe Asp Gln Gln Leu Ala Leu Gln Trp Val Gln
            100                 105                 110

Lys Asn Ile Ala Ala Phe Gly Gly Asn Pro Lys Ser Val Thr Leu Phe
        115                 120                 125

Gly Glu Ser Ser Gly Ala Ala Ser Val Ser Leu His Leu Leu Ser Pro
    130                 135                 140

Gly Ser His Ser Leu Phe Thr Arg Ala Ile Leu Gln Ser Gly Ser Ala
145                 150                 155                 160

Asn Ala Pro Trp Ala Val Thr Ser Leu Tyr Glu Ala Arg Asn Arg Thr
                165                 170                 175

Leu Asn Leu Ala Lys Leu Thr Gly Cys Ser Arg Glu Asn Glu Thr Glu
            180                 185                 190
```

-continued

```
Ile Ile Lys Cys Leu Arg Asn Lys Asp Pro Gln Glu Ile Leu Leu Asn
        195                 200                 205

Glu Ala Phe Val Val Pro Tyr Gly Thr Pro Leu Gly Val Asn Phe Gly
    210                 215                 220

Pro Thr Val Asp Gly Asp Phe Leu Thr Asp Met Pro Asp Ile Leu Leu
225                 230                 235                 240

Glu Leu Gly Gln Phe Lys Lys Thr Gln Ile Leu Val Gly Val Asn Lys
                245                 250                 255

Asp Glu Gly Thr Trp Phe Leu Val Tyr Gly Ala Pro Gly Phe Ser Lys
            260                 265                 270

Asp Asn Asn Ser Ile Ile Thr Arg Lys Glu Phe Gln Glu Gly Leu Lys
        275                 280                 285

Ile Phe Phe Pro Gly Val Ser Glu Phe Gly Lys Glu Ser Ile Leu Phe
    290                 295                 300

His Tyr Thr Asp Trp Val Asp Asp Gln Arg Pro Glu Asn Tyr Arg Glu
305                 310                 315                 320

Ala Leu Gly Asp Val Val Gly Asp Tyr Asn Phe Ile Cys Pro Ala Leu
                325                 330                 335

Glu Phe Thr Lys Lys Phe Ser Glu Trp Gly Asn Asn Ala Phe Phe Tyr
            340                 345                 350

Tyr Phe Glu His Arg Ser Ser Lys Leu Pro Trp Pro Glu Trp Met Gly
        355                 360                 365

Val Met His Gly Tyr Asp Ile
    370                 375
```

<210> SEQ ID NO 29
<211> LENGTH: 975
<212> TYPE: DNA
<213> ORGANISM: Artificial
<220> FEATURE:
<223> OTHER INFORMATION: 12-4 mutant (A199S/F227A/S287G/A328W/E441D)
      BChE nucleic acid sequence for amino acid residues 117-441

<400> SEQUENCE: 29

```
ggttttcaaa ctggaacatc atctttacat gtttatgatg gcaagtttct ggctcgggtt      60

gaaagagtta ttgtagtgtc aatgaactat agggtgggtg ccctaggatt cttagctttg     120

ccaggaaatc ctgaggctcc agggaacatg ggtttatttg atcaacagtt ggctcttcag     180

tgggttcaaa aaaatatagc agcctttggt ggaaatccta aaagtgtaac tctctttgga     240

gaaagttccg gagcagcttc agttagcctg catttgcttt ctcctggaag ccattcattg     300

ttcaccagag ccattctgca aagtggttcc gctaatgctc cttgggcggt aacatctctt     360

tatgaagcta ggaacagaac gttgaactta gctaaattga ctggttgctc tagagagaat     420

gagactgaaa taatcaagtg tcttagaaat aaagatcccc aagaaattct tctgaatgaa     480

gcatttgttg tcccctatgg gactcctttg ggtgtaaact ttggtccgac cgtggatggt     540

gattttctca ctgacatgcc agacatatta cttgaacttg gacaatttaa aaaaacccag     600

attttggtgg gtgttaataa agatgaaggg acatggtttt tagtctatgg tgctcctggc     660

ttcagcaaag ataacaatag tatcataact agaaaagaat ttcaggaagg tttaaaaata     720

ttttttccag gagtgagtga gtttggaaag gaatccatcc tttttcatta cacagactgg     780

gtagatgatc agagacctga aaactaccgt gaggccttgg gtgatgttgt tggggattat     840

aatttcatat gccctgcctt ggagttcacc aagaagttct cagaatgggg aaataatgcc     900

tttttctact attttgaaca ccgatcctcc aaacttccgt ggccagaatg gatgggagtg     960
```

```
atgcatggct atgac                                                    975


<210> SEQ ID NO 30
<211> LENGTH: 325
<212> TYPE: PRT
<213> ORGANISM: Artificial
<220> FEATURE:
<223> OTHER INFORMATION: 12-4 mutant (A199S/F227A/S287G/A328W/E441D)
      BChE amino acid sequence for residues 117-441

<400> SEQUENCE: 30

Gly Phe Gln Thr Gly Thr Ser Ser Leu His Val Tyr Asp Gly Lys Phe
1               5                   10                  15

Leu Ala Arg Val Glu Arg Val Ile Val Val Ser Met Asn Tyr Arg Val
            20                  25                  30

Gly Ala Leu Gly Phe Leu Ala Leu Pro Gly Asn Pro Glu Ala Pro Gly
        35                  40                  45

Asn Met Gly Leu Phe Asp Gln Gln Leu Ala Leu Gln Trp Val Gln Lys
    50                  55                  60

Asn Ile Ala Ala Phe Gly Gly Asn Pro Lys Ser Val Thr Leu Phe Gly
65                  70                  75                  80

Glu Ser Ser Gly Ala Ala Ser Val Ser Leu His Leu Leu Ser Pro Gly
                85                  90                  95

Ser His Ser Leu Phe Thr Arg Ala Ile Leu Gln Ser Gly Ser Ala Asn
            100                 105                 110

Ala Pro Trp Ala Val Thr Ser Leu Tyr Glu Ala Arg Asn Arg Thr Leu
        115                 120                 125

Asn Leu Ala Lys Leu Thr Gly Cys Ser Arg Glu Asn Glu Thr Glu Ile
    130                 135                 140

Ile Lys Cys Leu Arg Asn Lys Asp Pro Gln Glu Ile Leu Leu Asn Glu
145                 150                 155                 160

Ala Phe Val Val Pro Tyr Gly Thr Pro Leu Gly Val Asn Phe Gly Pro
                165                 170                 175

Thr Val Asp Gly Asp Phe Leu Thr Asp Met Pro Asp Ile Leu Leu Glu
            180                 185                 190

Leu Gly Gln Phe Lys Lys Thr Gln Ile Leu Val Gly Val Asn Lys Asp
        195                 200                 205

Glu Gly Thr Trp Phe Leu Val Tyr Gly Ala Pro Gly Phe Ser Lys Asp
    210                 215                 220

Asn Asn Ser Ile Ile Thr Arg Lys Glu Phe Gln Glu Gly Leu Lys Ile
225                 230                 235                 240

Phe Phe Pro Gly Val Ser Glu Phe Gly Lys Glu Ser Ile Leu Phe His
                245                 250                 255

Tyr Thr Asp Trp Val Asp Asp Gln Arg Pro Glu Asn Tyr Arg Glu Ala
            260                 265                 270

Leu Gly Asp Val Val Gly Asp Tyr Asn Phe Ile Cys Pro Ala Leu Glu
        275                 280                 285

Phe Thr Lys Lys Phe Ser Glu Trp Gly Asn Asn Ala Phe Phe Tyr Tyr
    290                 295                 300

Phe Glu His Arg Ser Ser Lys Leu Pro Trp Pro Glu Trp Met Gly Val
305                 310                 315                 320

Met His Gly Tyr Asp
                325
```

HIGH-ACTIVITY MUTANTS OF BUTYRYLCHOLINESTERASE FOR COCAINE HYDROLYSIS AND METHOD OF GENERATING THE SAME

RELATED APPLICATIONS

This application is a division of and claims benefit to U.S. patent application Ser. No. 13/767,418, filed Feb. 14, 2013 and now allowed, which is a division of and claims benefit to U.S. patent application Ser. No. 13/449,107, now issued as U.S. Pat. No. 8,399,644, filed Apr. 17, 2012, which is a division of and claims benefit to U.S. patent application Ser. No. 13/018,641, now issued as U.S. Pat. No. 8,193,327, filed Feb. 1, 2011, which is a division of and claims benefit to U.S. patent application Ser. No. 12/752,920, now issued as U.S. Pat. No. 7,919,082, filed Apr. 1, 2010, which is a division of and claims benefit to U.S. patent application Ser. No. 12/192,394, now issued as U.S. Pat. No. 7,731,957, filed Aug. 15, 2008, which is a division of and claims benefit to U.S. patent application Ser. No. 11/243,111, now issued as U.S. Pat. No. 7,438,904, filed Oct. 4, 2005. The contents of which are incorporated herein by reference in their entirety.

GOVERNMENT INTEREST

Subject matter described herein was made with government support under Grant Number R01DA013930 awarded by the National Institute on Drug Abuse (NIDA) of the National Institutes of Health (NIH). The government has certain rights in the described subject matter.

FIELD OF THE INVENTION

The present invention relates to butyrylcholinesterase variant polypeptides, and in particular, butyrylcholinesterase mutants having amino acid substitutions.

BACKGROUND OF THE INVENTION

Cocaine abuse is a major medical and public health problem that continues to defy treatment. The disastrous medical and social consequences of cocaine addiction, such as violent crime, loss in individual productivity, illness and death, have made the development of an effective pharmacological treatment a high priority. However, cocaine mediates its reinforcing and toxic effects by blocking neurotransmitter reuptake and the classical pharmacodynamic approach has failed to yield small-molecule receptor antagonists due to the difficulties inherent in blocking a blocker. An alternative to receptor-based approaches is to interfere with the delivery of cocaine to its receptors and accelerate its metabolism in the body.

The dominant pathway for cocaine metabolism in primates is butyrylcholinesterase (BChE)-catalyzed hydrolysis at the benzoyl ester group (Scheme 1).

Scheme 1.
Schematic representation of BChE-catalyzed hydrolysis at the benzoyl ester group.

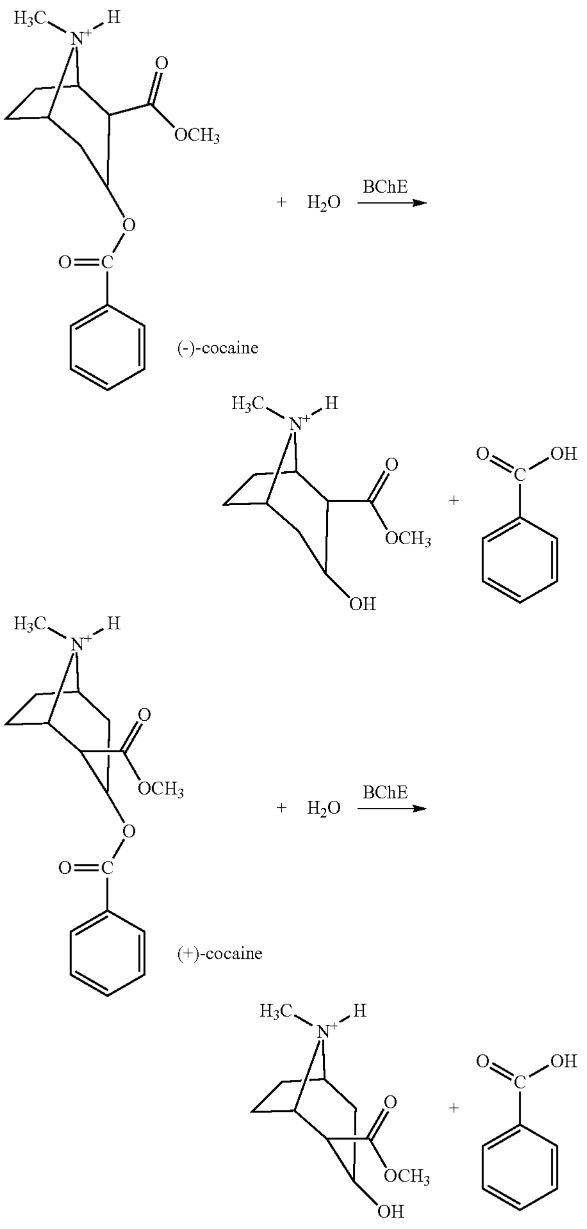

(-)-cocaine (+)-cocaine

Scheme 1. Schematic representation of BChE-catalyzed hydrolysis at the benzoyl ester group.

Only 5% of the cocaine is deactivated through oxidation by the liver microsomal cytochrome P450 system. Cocaine hydrolysis at benzoyl ester group yields ecgonine methyl ester, whereas the oxidation produces norcocaine. The metabolite ecgonine methyl ester is a biologically inactive metabolite, whereas the metabolite norcocaine is hepatotoxic and a local anesthetic. BChE is synthesized in the liver and widely distributed in the body, including plasma, brain, and lung. Extensive experimental studies in animals and humans demonstrate that enhancement of BChE activity by administration of exogenous enzyme substantially decreases cocaine half-life.

Enhancement of cocaine metabolism by administration of BChE has been recognized to be a promising pharmacokinetic approach for treatment of cocaine abuse and dependence. However, the catalytic activity of this plasma enzyme is three orders-of-magnitude lower against the naturally occurring (−)-cocaine than that against the biologically inactive (+)-cocaine enantiomer. (+)-cocaine can be cleared from plasma in seconds and prior to partitioning into the central nervous system (CNS), whereas (−)-cocaine has a plasma half-life of approximately 45-90 minutes, long enough for manifestation of the CNS effects which peak in minutes. Hence, BChE mutants with high activity against (−)-cocaine are highly desired for use in humans. Although some BChE mutants with increased catalytic activity over wild-type BChE have previously been generated, there exists a need for mutant BChE with even higher catalytic activity. Thus, prior mutants provide limited enhancement in catalytic activity over wild-type BChE.

Previous studies such as (a) Masson, P.; Legrand, P.; Bartels, C. F.; Froment, M-T.; Schopfer, L. M.; Lockridge, O. *Biochemistry* 1997, 36, 2266 (b) Masson, P.; Xie, W., Froment, M-T.; Levitsky, V.; Fortier, P.-L.; Albaret, C.; Lockridge, O. *Biochim. Biophys. Acta* 1999, 1433, 281, (c) Xie, W.; Altamirano, C. V.; Bartels, C. F.; Speirs, R. J.; Cashman, J. R.; Lockridge, O. *Mol. Pharmacol.* 1999, 55, 83, (d) Duysen, E. G.; Bartels, C. F.; Lockridge, O. *J. Pharmacol. Exp. Ther.* 2002, 302, 751, (e) Nachon, F.; Nicolet, Y.; Viguie, N.; Masson, P.; Fontecilla-Camps, J. C.; Lockridge, O. *Eur. J. Biochem.* 2002, 269, 630, (f) Zhan, C.-G.; Landry, D. W. *J. Phys. Chem. A* 2001, 105, 1296; Berkman, C. E.; Underiner, G. E.; Cashman, J. R. *Biochem. Pharmcol.* 1997, 54, 1261; (g) Sun, H.; Yazal, J. E.; Lockridge, O.; Schopfer, L. M.; Brimijoin, S.; Pang, Y.-P. *J. Biol. Chem.* 2001, 276, 9330, (h) Sun, H.; Shen, M. L.; Pang, Y. P.; Lockridge, O.; Brimijoin, S. *J. Pharmacol. Exp. Ther.* 2002, 302, 710, (i) Sun, H.; Pang, Y. P.; Lockridge, O.; Brimijoin, S. *Mol. Pharmacol.* 2002, 62, 220 (hereinafter "Sun et al"); and (j) Zhan, C.-G.; Zheng, F.; Landry, D. W. *J. Am. Chem. Soc.* 2003, 125, 2462 (hereinafter "Zhan et al"), herein all incorporated by reference, suggested that, for both (−)-cocaine and (+)-cocaine, the BChE-substrate binding involves two different types of complexes: non-prereactive and prereactive BChE-substrate complexes. Whereas the non-prereactive BChE-cocaine complexes were first reported by Sun et al, Zhan et al were the first reporting the prereactive BChE-cocaine complexes and reaction coordinate calculations, disclosed in Zhan et al.

It was demonstrated that (−)/(+)-cocaine first slides down the substrate-binding gorge to bind to W82 and stands vertically in the gorge between D70 and W82 (non-prereactive complex) and then rotates to a position in the catalytic site within a favorable distance for nucleophilic attack and hydrolysis by S198 (prereactive complex). In the prereactive complex, cocaine lies horizontally at the bottom of the gorge. The main structural difference between the BChE-(−)-cocaine complexes and the corresponding BChE-(+)-cocaine complexes exists in the relative position of the cocaine methyl ester group. Reaction coordinate calculations revealed that the rate-determining step of BChE-catalyzed hydrolysis of (+)-cocaine is the chemical reaction process, whereas for (−)-cocaine the change from the non-prereactive complex to the prereactive complex is rate determining. A further analysis of the structural changes from the non-prereactive complex to the prereactive complex reveals specific amino acid residues hindering the structural changes, providing initial clues for the rational design of BChE mutants with improved catalytic activity for (−)-cocaine.

Previous molecular dynamics (MD) simulations of prereactive BChE-cocaine binding were limited to wild-type BChE. Even for the non-prereactive BChE-cocaine complex, only one mutant (A328W/Y332A) BChE binding with (−)-cocaine was simulated and its catalytic activity for (−)-cocaine was reported by Sun et al. No MD simulation was performed on any prereactive enzyme-substrate complex for (−)- or (+)-cocaine binding with a mutant BChE. In addition, all previous computational studies of Sun et al and Zhan et al of BChE interacting with cocaine were performed based on a homology model of BChE when three-dimensional (3D) X-ray crystal structure was not available for BChE, as taught by Nicolet, Y.; Lockridge, O.; Masson, P.; Fontecilla-Camps, J. C.; Nachon, F. *J. Biol. Chem.* 2003, 278, 41141 (hereinafter "Nicolet et al"), recently reported 3D X-ray crystal structures of BChE. As expected, the structure of BChE is similar to a previously published theoretical model of this enzyme and to the structure of acetylcholinesterase.

The main difference between the experimentally determined BChE structure and its model was found at the acyl binding pocket (acyl loop) that is significantly bigger than expected. It is unclear whether the structural difference at the acyl binding pocket significantly affect BChE binding with (−)-cocaine and (+)-cocaine. Although previous MD simulations of cocaine binding with wild-type BChE and the reaction coordinate calculations point to some amino acid residues that might need to be mutated for the purpose of improving the catalytic activity for (−)-cocaine hydrolysis, it remained unknown which exact amino acid mutations will result in a BChE with a higher catalytic activity for (−)-cocaine.

Computational studies of wild-type BChE and cocaine from Sun, et al, based on a "homology model," suggest that the rate-determining step for BChE-catalyzed hydrolysis of cocaine is the rotation of the cocaine in the active site of BChE. By decreasing the hindrance of the rotation, the rate of the hydrolysis may be enhanced. Sun, et al describes creating an A328W/Y332A BChE mutant by: (1) replacing Tyr332 with Ala, "to reduce the steric hindrance and the π-π interaction that impede rotation," and (2) replacing Ala328 with Trp "to provide a cation-π interaction to restore substrate affinity lost in disabling the π-π interaction."

Sun et al studied the A328W/Y332A BChE mutant using enzyme assays and kinetics. In vitro studies were conducted using human plasma and in vivo studies were conducted using male Sprague-Dawley rats. The mutant was found to have enhanced catalytic properties. The mutant was further studied using molecular modeling. The three dimensional (3D) structure of A328W/Y332A was generated from the computationally generated 3D model of wild-type BChE and changing the relevant residues using commercially available software. Cocaine was docked to the catalytic gorge of the mutant BChE using other commercially available software. The cocaine-enzyme complex was refined by molecular dynamic simulation. The data generated by the molecular modeling studies were consistent with enzyme assays and kinetic data.

It should be noted that all prior computational techniques (molecular docking and molecular dynamics simulation) used by other researchers are based on an empirical force field which cannot be used to perform any necessary reaction coordinate calculation for the detailed understanding of the complicated catalytic reaction process. As it is well-known, it is particularly challenging to model and simulate the detailed reaction pathway and predict the kinetics of such an enzymatic reaction.

U.S. Patent Application Publication Nos. 2004/0121970; 2004/0120939; and 2003/0153062, describe 20+BChE mutants, or "variants," from human and other animals, each having from one to six amino acid alterations and increased cocaine hydrolysis activity. For example, mutants include F227A/A328W; F227A/S287G/A328W; A119S/S287G/A328W; A328W/Y332M/S287G/F227A, A199S/F227A/S/287G/A328W and A119S/F227A/S287G/A328W/Y332M. The mutants have varying increases in catalytic activity, up to 100-fold increase relative to wild-type BChE.

There exists a need in the art for determining which proposed mutant BChEs should have ever increasing catalytic activity and for generating those mutants which should have enhanced catalytic activity.

SUMMARY OF THE INVENTION

The present invention includes five novel human BChE mutants that have unexpected increased catalytic efficiency for cocaine hydrolysis. The mutants have various unique amino acid residue substitutions which provide the surprising enhanced catalytic activity. These mutants are (1) A199S/A328W/Y332G mutant (SEQ ID NO: 2), which has a approximately 65-fold improved catalytic efficiency against (−)-cocaine; (2) A199S/F227A/A328W/Y332G mutant (SEQ ID NO: 8), which has an approximately 148-fold improved catalytic efficiency against (−)-cocaine; (3) A199S/S287G/A328W/Y332G mutant (SEQ ID NO: 14), which has an approximately 456-fold improved catalytic efficiency against (−)-cocaine; (4) A199S/F227A/S287G/A328W/Y332G mutant (SEQ ID NO: 20), which has an approximately 1,003-fold improved catalytic efficiency against (−)-cocaine; and (5) A199S/F227A/S287G/A328W/E441D mutant (SEQ ID NO: 26), which has an approximately 445-fold improved catalytic efficiency against (−)-cocaine.

In addition, the aforementioned mutant amino acid sequences can be truncated without substantially affecting the catalytic activity so that amino acid residues 1-67 and 443-574 can be removed without substantially affecting the catalytic activity of the enzyme. SEQ ID NOS: 4, 10, 16, 22 and 28 are the amino acid sequences for residue 68-142 corresponding to mutants 1-5, respectively. In addition, with regard to mutants 1-4, it was found that amino acid residues before 117 and after 438 could be removed without substantially changing the activity of the mutant enzymes, resulting in truncated amino acid sequences having SEQ ID NOS: 6, 12, 18 and 24, respectively. Finally with regard to mutant 5, amino acid residues before 117 and after 441 could be removed without substantially changing its activity resulting in SEQ ID NO: 30.

These aforementioned truncated sequences all of with similar catalytic activity is based on protein structures.

Further, the present invention is directed to a novel and unique pharmaceutical composition which comprises a butyrylcholinesterase variant, namely mutants 1-5, along with a suitable pharmaceutical carrier. The pharmaceutical composition can be administered to an individual in an effective amount to lower the patient's cocaine blood concentration and in particular (−)-cocaine blood concentration.

In addition, the present invention is directed to a novel and unique method for developing mutants which have enhanced catalytic efficiency. The generation method includes both a computational portion and an experimental portion. With regard to the computational portion, a variety of state of the art computational techniques including molecular modeling, molecular dynamics (MD) simulations and hybrid quantum mechanical/molecular mechanical (QM/MM) calculations, provide a virtual screening of possible BChE mutants. This virtual screening predicts which mutation will lead to a more stable transition state for a rate-determining step compared to the corresponding separated reactants, i.e., free cocaine and free enzyme. The more stable the transition state, the lower the energy barrier, and the higher the catalytic efficiency. Following the computational portion, an experimental test is then conducted on the possible mutants of the computation portion. The experimental test includes site-directed mutagenesis, protein expression, and enzyme activity assay. The experimental tests are conducted on mutants which are predicted to have a high catalytic efficiency against (−)-cocaine than the wild-type BChE and/or other known BChE mutants against (−)-cocaine. Thus, the present method identifies or predicts mutants having high catalytic activity for cocaine hydrolysis by performing molecular modeling and MD simulations on the transition state structures of possible mutants of BChE. This method is an improvement over traditional random-search approaches, which, given the complex catalytic mechanism of cocaine hydrolysis, makes it difficult to improve the catalytic activity of BChE for cocaine hydrolysis.

The present invention in one form, concerns a butyrylcholinesterase variant peptide comprising an amino acid sequence selected from the group consisting of SEQ ID NOS: 2, 4, 6, 8, 10, 12, 14, 16, 18, 20, 22, 24, 26, 28, and 30.

The present invention in another form thereof concerns a nucleic acid molecule comprising a nucleic acid sequence which encodes a butyrylcholinesterase variant peptide, the nucleic acid sequence selected from the group consisting of SEQ ID NOS: 1, 3, 5, 7, 9, 11, 13, 15, 17, 19, 21, 23, 25, 27, and 29.

The present invention in another form thereof concerns a pharmaceutical composition comprising a butyrylcholinesterase variant polypeptide comprising an amino acid sequence selected from the group consisting of SEQ ID NOS. 2, 4, 6, 8, 10, 12, 14, 16, 18, 20, 22, 24, 26, 28, and 30; and a suitable pharmaceutical carrier.

The present invention in another form thereof concerns a method for treating a cocaine-induced condition comprising administering to an individual an effective amount of butyrylcholinesterase variant peptide having an amino acid sequence selected from the group consisting of SEQ ID NOS. 2, 4, 6, 8, 10, 12, 14, 16, 18, 20, 22, 24, 26, 28, and 30, to lower blood cocaine concentration.

The present invention is another form thereof concerns a method for treating a cocaine induced condition comprising administering to an individual an effective amount of a pharmaceutical composition comprising a butyrylcholinesterase variant having an amino acid sequence selected from the group consisting of SEQ ID NOS. 2, 4, 6, 8, 10, 12, 14, 16, 18, 20, 22, 24, 26, 28, and 30, and suitable pharmaceutical carrier of claim 3 to an individual in an effective amount to lower blood cocaine concentration.

The present invention in yet another form thereof concerns a method for generating butyrylcholinesterase mutants. The method includes generating an initial structure of the transition state structure for the rate-determining step of the cocaine hydrolysis catalyzed by a possible butyrylcholinesterase mutant. A sufficiently long time molecular dynamics simulation is performed on the transition state structure in water to have a stable molecular dynamics trajectory. The molecular dynamics trajectory is analyzed and the hydrogen bonding energies are estimated between the carboxyl oxygen of the (−)-cocaine benzyl ester and the oxyanion hole of the possible butyrylcholinesterase mutant. If the overall hydrogen binding energy between the carboxyl oxygen of the (−)-cocaine benzyl ester and the possible butyrylcholinesterase mutant, in the transition state, is stronger than the overall hydrogen binding energy between the carboxyl oxygen of the (−)-cocaine benzyl ester and the wild-type butyrylcholinesterase, optionally, hybrid quantum mechanical/molecular mechanical (QM/MM) geometry optimization is performed to refine the molecular dynamics-simulated structure, the hydrogen binding energies are calculated and the energy barrier is evaluated. Finally, the butyrylcholinesterase mutant is generated.

In various alternative embodiments, the generating an initial structure of the transition state structure is based on reaction coordinate calculations for the wild-type butyrylcholinesterase. The generating butyrylcholinesterase mutant includes performing site-directed mutagenesis on a nucleic acid sequence which includes wild-type butyrylcholinesterase to generate the mutant butyrylcholinesterase nucleic acid sequence. Using the mutant butyrylcholinesterase nucleic acid sequence, the protein encoded by the mutant nucleic acid sequences is expressed to produce mutant butyrylcholinesterase and catalytic activity assay is performed on the mutant butyrylcholinesterase.

The hybrid quantum mechanical/molecular mechanical geometry optimization may include calculating the hydrogen binding energies and evaluating the energy barriers only if the overall hydrogen binding energy between the carboxyl oxygen of the (−)-cocaine benzyl ester and the possible butyrylcholinesterase mutant, in the transition state, is stronger than known butyrylcholinesterase mutants against (−)-cocaine.

In yet another alternative further embodiment, the method for generating butyrylcholinesterase mutants further includes determining the rate-limiting step in the hydrolysis of (−)-cocaine by the possible butyrylcholinesterase mutant by conducting molecular dynamics simulations and quantum mechanical/molecular mechanical calculations relating to the transition states for other reaction steps between (−)-cocaine by the possible butyrylcholinesterase mutant and calculating respective energy barriers, thereby establishing which of the reaction steps is the rate-determining one.

BRIEF DESCRIPTION OF THE DRAWINGS

FIG. 1A represents the non-prereactive enzyme-substrate complexes; and FIG. 1B represents the prereactive enzyme-substrate complexes in accordance with the present invention.

FIG. 2 shows the binding of structures of the simulated non-prereactive and prereactive complexes of wild-type BChE binding with two entomers of cocaine in which FIG. 2A depicts BChE (−)-cocaine non-prereactive complex; FIG. 2B depicts BChE (−)-cocaine prereactive complex, FIG. 2C depicts BChE (+)-cocaine non-prereactive complex; and FIG. 2D depicts BChE (+)-cocaine prereactive complex.

DETAILED DESCRIPTION OF THE PREFERRED EMBODIMENTS

Figure 1:
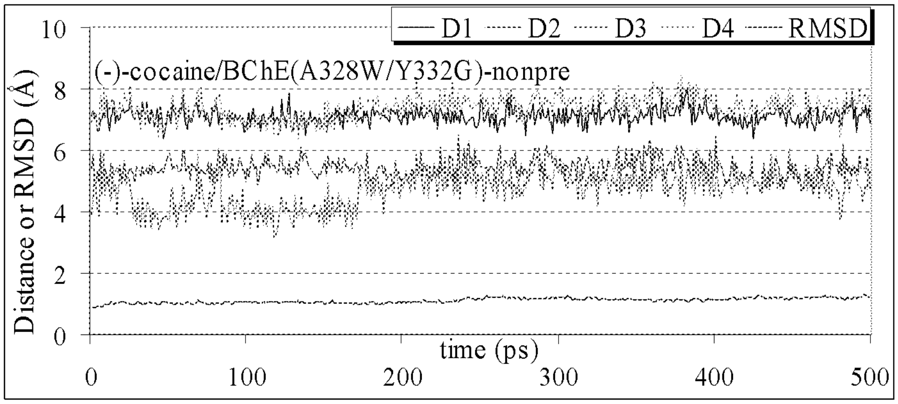
FIG. 1 are plots of distances in the MD simulation (−)-cocaine binding with A328W/Y332G BChE versus the simulation time, along with root-mean-square deviation (RMSD) in the enzyme-substrate complexes where
Figure 1:
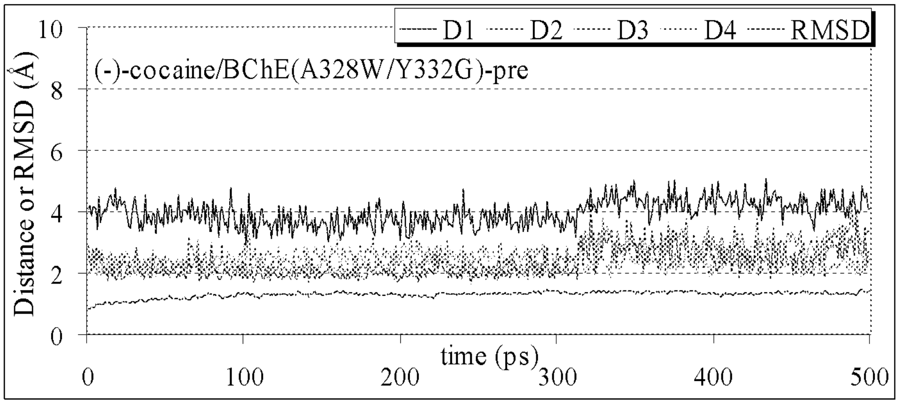

The present invention has two major improvements over the prior art. The first is the presently discovered BChE mutants, mutant 1, A199S/A328W/Y332G; mutant 2, A199S/F227A/A328W/Y332G; mutant 3, A199S/S287G/A328W/Y332G; mutant 4, A199S/F227A/S287G/A328W/Y332G; and mutant 5, A199S/F227A/S287G/A328W/E441D each have a significantly higher catalytic efficiency. The second improvement is concerning the mutant designing or discovering process.

The BChE mutants 1-5 have full length amino acid sequences, SEQ ID NOS: 2, 8, 14, 20, and 26, respectively, which are encoded by nucleic acid sequences having SEQ ID NOS: 1, 7, 13, 19, and 25, respectively. Table 1 summarizes the catalytic efficiency against (−)-cocaine for the five mutants.

In addition to the full length BChE mutants, the respective amino acid sequence can be truncated without substantially affecting the respective catalytic activity. With all mutants, residues 1-67 and 443-574 can be removed without substantially affecting the catalytic activity of the respective mutant BChE. Further, with regard to mutant 1-4, amino acids 1-116 and 439-574 can be omitted without substantially affecting its respective catalytic activity. With regard to mutant 5, amino acid residues 1-116 and 442-574 can be omitted without substantially affecting its catalytic activity. Table 1 also provides a summary of amino acid SEQ ID NOS and corresponding nucleic acid SEQ ID NOS for the aforementioned truncated mutant BChE sequences.

TABLE 1

| Mutant Number | Amino Acid Substituting | Nucleic Acid SEQ ID NO. | Amino Acid SEQ ID NO. | Partially Truncated Nucleic Acid Sequence Corresponding To Amino Acid Residues 68-442 | SEQ ID NO. for Amino Acid Residues 68-442 | SEQ ID NO Corresponding To Amino Acid Residues 117-438/441* | SEQ ID NO. for Amino Acid Residues 117-438/441* | Catalytic Efficiency Against (−)-cocaine |
|---|---|---|---|---|---|---|---|---|
| 1 | A199S/ A328W/ Y332G | 1 | 2 | 3 | 4 | 5 | 6 | 65-fold |
| 2 | A199S/ F227A/ A328W/ Y332G | 7 | 8 | 9 | 10 | 11 | 12 | 148-fold |
| 3 | A199S/ S287G/ A328W/ Y332G | 13 | 14 | 15 | 16 | 17 | 18 | 456-fold |
| 4 | A199S/ F227A/ S287G/ A328W/ Y332G | 19 | 20 | 21 | 22 | 22 | 24 | 1,003-fold |
| 5 | A199S/ F227A/ S287G/ A328W/ E441D | 25 | 26 | 27 | 28 | 29 | 30 | 445-fold |

(*Amino acid residues 117-438 for mutants 1-4 and residues 117-441 for mutant 5.)

The BChE variant polypeptide, e.g., SEQ ID NOS: 2, 4, 6, 8, 10, 12, 14, 16, 18, 20, 22, 24, 26, 28, and 30 can be formulated in a pharmaceutical composition along with a suitable pharmaceutical carrier known to one skilled in the art.

The present BChE variant polypeptides can be used in treating a cocaine-induced condition by administering to an individual, an effective amount of one of the BChE variant polypeptides, i.e., SEQ ID NOS: 2, 4, 6, 8, 10, 12, 14, 16, 18, 20, 22, 24, 26, 28, and 30, to lower blood cocaine concentration. The BChE variant polypeptide may be administered in the form of a pharmaceutical composition in which the BChE variant is included with a suitable pharmaceutical carrier. Treatment of a cocaine induced condition using one of the aforementioned BChE variant polypeptides can be done in accordance with Zhan et al., page 2463.

The preferred dose for administration of a butyrylcholinesterase or peptide composition in accordance with the present invention is that amount which will be effective in lowering (−)-cocaine concentration in a patient's bloodstream, and one would readily recognize that this amount will vary greatly depending on the nature of cocaine consumed, e.g., injected or inhaled, and the condition of a patient. An "effective amount" of butyrylcholinesterase mutant or pharmaceutical agent to be used in accordance with the invention is intended to mean a nontoxic but sufficient amount of the agent, such that the desired prophylactic or therapeutic effect is produced. Thus, the exact amount of the enzyme or a particular agent that is required will vary from subject to subject, depending on the species, age, and general condition of the subject, the severity of the condition being treated, the particular carrier or adjuvant being used and its mode of administration, and the like. Similarly, the dosing regimen should also be adjusted to suit the individual to whom the composition is administered and will once again vary with age, weight, metabolism, etc. of the individual. Accordingly, the "effective amount" of any particular butyrylcholinesterase composition will vary based on the particular circumstances, and an appropriate effective amount may be determined in each case of application by one of ordinary skill in the art using only routine experimentation.

A unique method was used to determine potential BChE mutants with projected increased catalytic activity for the hydrolysis of cocaine. The method provides a unique approach which first models the potential BChE mutant interaction with cocaine followed by generating the BChE mutant if the predicted model indicates that the BChE variant should have enhanced catalytic activity. The method includes generating an initial structure of the transition state structure for the rate-determining step for the cocaine hydrolysis catalyzed by a possible BChE mutant. A sufficiently long time molecular dynamics simulation is performed on the transition state structure in water to have a stable molecular dynamics trajectory. The molecular dynamics trajectory is analyzed and the hydrogen binding energies are estimated between the carboxyl oxygen of the (−)-cocaine benzoyl ester and the oxyanion hole of the possible BChE mutant. If the overall hydrogen binding energy between the carboxyl oxygen of the (−)-cocaine benzoyl ester and the possible BChE mutant, in the transition state, is stronger than the overall hydrogen binding energy between the carboxyl oxygen of the (−)-cocaine benzoyl ester and the wild-type BChE, hybrid quantum mechanical/molecular mechanical (QM/MM) geometry optimization is performed to refine the molecular dynamics-simulated structure, the hydrogen binding energies are calculated and the energy barrier is evaluated. The QM/MM calculations make the computational predictions more reliable. Finally, the BChE mutant is generated.

With regard to the molecular dynamics (MD) simulations and quantum mechanical/molecular mechanical (QM/MM) calculations, the first chemical reaction step of (−)-cocaine hydrolysis catalyzed by butyrylcholinesterase (BChE) mutants and, when needed, other reaction steps are modeled and calculated using molecular dynamics simulations and QM/MM calculations. Following this modeling, mutant BChE's are created using site-directed mutagenesis followed by protein expression. The aforementioned five mutants were identified by computational analysis and generated by site-directed mutagenesis which have significantly enhanced (−)-cocaine hydrolysis catalytic efficiency compared with wild-type BChE.

In the present method computational analysis in the form of molecular modeling of a potential BChE mutant and MD simulations and QM/MM calculations provide virtual screening of possible BChE mutants which have predicted enhanced catalytic activity for (−)-cocaine. For example, the MD simulations and QM/MM calculations predict which mutation will lead to a more stable transition state for the rate determining step compared to the corresponding separated reagents, i.e., free cocaine and free possible mutant BChE, where the more stable transition state leads to a lower energy barrier and higher predicted catalytic efficiency. Only after the computational analysis predicts enhanced catalytic efficiency, is site-directed mutagenesis conducted on wild-type BChE nucleic acid sequence to generate a mutant nucleic acid sequence which is then used to express a mutant BChE protein. The mutant BChE protein is then used in catalytic assays to determine the catalytic efficiency against (−)-cocaine.

The use of predictive, computational modeling of the present method for identifying mutant BChE candidates and the resulting mutant BChE are novel and unexpected over prior conventional methods which will now be readily apparent to one of ordinary skill in the art.

Using the present method, most discovered new mutants include a specific mutation (Y332G) on residue #332. No prior BChE mutant having the Y332G mutation had ever been reported previously; only mutations Y332A and Y332M on residue #332 had been tested previously by other researchers. Prior to the present invention, there was no reason to expect that a mutant including Y332G mutation should be better than the corresponding mutant including Y332A mutation or Y332M. Thus, the present mutants with a Y332G mutation which have enhanced catalytic activity represent a surprising and unexpected result over prior BChE mutants.

A Y332G mutant (single mutation) was first tested and found that the Y332G mutant had a slightly low (or approximately equal) catalytic efficiency than the wild-type. So, only an appropriate combination of different mutations on different residues could make the enzyme more active. As seen below, the prior art did not reveal that any of the particular combinations tested was expected to have an improved catalytic efficiency. The present method is based on the present unique, extensive computational modeling and simulations of the detailed catalytic mechanism for both the wild-type BChE and the mutants.

The primary improvement of the present method over the prior art is that high-performance computational modeling and simulations of the detailed catalytic mechanism are performed, which includes modeling how cocaine binds with BChE and the subsequent structural transformation and chemical reaction process. The prior art only considered the cocaine binding with the enzyme (BChE) and was unable to examine the detailed catalytic reaction process after the BChE-cocaine binding. When molecular modeling was limited to studying the BChE-cocaine binding, one could only design a mutation to improve the BChE-cocaine binding without knowing whether the mutation will also speedup the subsequent chemical reaction process or not.

To overcome the obstacles of prior challenges to using computational techniques such as molecular docking and molecular dynamics simulation previously used by others which were based on an empirical force field which cannot be used to perform necessary reaction coordinate calculations for the catalytic reaction process, a variety of state-of-the-art computational techniques of homology modeling, molecular docking, molecular dynamics, quantum mechanics (QM), and hybrid quantum mechanics/molecular mechanics (QM/MM) were used for the rational design of the BChE mutants. The combined use of these computational techniques, including QM and QM/MM, led to the study of the detailed reaction coordinate of the BChE-catalyzed hydrolysis of cocaine which, for the first time, provided the detailed structures of all transition states and intermediates existing in the reaction process and the corresponding energetics. These extensive computational modeling and simulation studies provided for the rational design of possible BChE mutants that not only can improve the BChE-cocaine binding, but also can speedup the subsequent chemical reaction process. As a result, one can now quickly discover the BChE mutants with the significantly improved catalytic efficiency.

In addition, to the differences mentioned above, the present molecular modeling of the BChE-cocaine binding also differs from the prior modeling. The molecular modeling in the prior art considered only one binding mode for each BChE-cocaine system, without modeling the possible cocaine rotation in the BChE active site after the binding. The present method considers two different binding modes for each BChE-cocaine system and the structural transformation between them: non-prereactive and prereactive BChE-cocaine complexes. The present modeling provides more detailed information about the BChE-cocaine binding and the subsequent structural transformation.

The present method includes molecular dynamics simulations performed on the cocaine binding with both the wild-type BChE and the mutants whereas prior molecular dynamics simulations were only performed on the cocaine binding with the wild-type BChE. As is shown below in the following experiments, the computational prediction could be completely wrong without directly modeling and simulating cocaine binding with the proposed mutants.

The present invention will now be discussed with regard to the following non-limiting examples in the form of experiments which are provided to enhance understanding of the present invention but in no way limit its scope or applicability.

Experiment 1

Computational Study of Cocaine Binding with Wild-Type and Mutant BChE's for A328W/Y332G, A328W/Y332A, and A328W/Y332A/Y419S A detailed computational study of cocaine binding with wild-type and mutant BChE's starting from the available X-ray crystal structure of wild-type BChE was performed. The simulated mutants include A328W/Y332G, A328W/Y332A, and A328W/Y332A/Y419S, as simple geometric consideration of the binding site suggests that these mutations could be important for changing the (−)-cocaine rotation from the non-prereactive complex to the prereactive complex. Wet experimental tests were conducted on the catalytic activity of these mutants for (−)-cocaine in order to verify the computational predictions. All of the obtained results clearly demonstrate that molecular modeling and MD simulations of cocaine binding with BChE mutants provide a reliable computational approach to the rational design of high-activity mutants of BChE for the (−)-cocaine hydrolysis.

3D Model of BChE.

The initial coordinates of human BChE used in the computational studies came from the X-ray crystal structure deposited in the Protein Data Bank (pdb code: 1P0P). The missing residues (D2, D3, E255, D378, D379, N455, L530, E531, and M532) in the X-ray crystal structure were built using the automated homology modeling tool Modeler disclosed by Sali, A.; Blundell, T. L. *J. Mol. Biol.* 1990, 212 403, and Sali, A.; Blundell, T. L. *J. Mol. Biol.* 1993, 234, 779, herein incorporated by reference, and InsightII software (Accelrys, Inc.) with the default parameters.

Molecular Docking.

Molecular docking was performed for each non-prereactive protein-ligand binding complex. The binding site was defined as a sphere with an approximately 15 Å radius around the active site residue S198. The amino acid residues included in the binding site model are not contiguous in the protein. Cocaine, considered as a ligand, was initially positioned at 17 Å in front of S198 of the binding site. Each BChE-cocaine binding complex was energy-minimized by using the steepest descent algorithm first until the maximum energy derivative is smaller than 4 kcal/mol/Å and then the conjugated gradient algorithm until the maximum energy derivative is smaller than 0.001 kcal/mol/Å. The energy minimization was followed by a 300 ps molecular dynamics (MD) simulation at T=298 K with a time step of 1 fs. During the energy minimization and MD simulation, only cocaine and the residues of BChE included in the binding site were allowed to move, while the remaining part of the protein was fixed. The energy-minimization and MD simulation for these processes were performed by using the Amber force field implemented in the Discover_3/InsightII calculation engine, disclosed by Cornell, W. D.; Cieplak, P.; Bayly, C. I.; Gould, I. R.; Merz, Jr., K. M.; Ferguson, D. M.; Spellmeyer, D. C.; Fox, T.; Caldwell, J. W.; Kollman, P. A. *J. Am. Chem. Soc.* 1995, 117, 5179. The non-bonded cut-off method and the dielectric constant were set up to group based (12 Å cut-off distance) and distance dependent, respectively (∈=4r) in accordance with Harvey, S. C. *Proteins* 1989, 5, 78-92, herein incorporated by reference.

Molecular Dynamic Simulation in Water.

The initial coordinates used in the MD simulation of the non-prereactive complexes were determined by using the molecular docking procedure described above, whereas the initial coordinates used in the MD simulation of the prereactive complexes were obtained from superimposing backbone of the X-ray crystal structure to that of the previously disclosed simulated prereactive complex of Zhan et al between cocaine and a homology model of wild-type BChE. Each BChE-cocaine binding complex was neutralized by adding two chloride counterions and was solvated in a rectangular box of TIP3P water molecules with a minimum solute-wall distance of 10 Å. The general procedure for carrying out the MD simulations in water is similar to that used in our previously reported other computational studies such as those in Zhan et al and (a) Zhan, C.-G.; Norberto de Souza, O.; Rittenhouse, R.; Ornstein, R. L. *J. Am. Chem. Soc.* 1999, 121, 7279, (b) Koca, J.; Zhan, C.-G.; Rittenhouse, R.; Ornstein, R. L. *J. Am. Chem. Soc.* 2001, 123, 817, (c) Koca, J.; Zhan, C.-G.; Rittenhouse, R. C.; Ornstein, R. L. *J. Comput. Chem.* 2003, 24, 368, herein all incorporated by reference. These simulations were performed by using the Sander module of Amber7 program as taught by Case, D. A.; Pearlman, D. A.; Caldwell, J. W.; Cheatham III, T. E.; Wang, J.; Ross, W. S.; Simmerling, C. L.; Darden, T. A.; Merz, K. M.; Stanton, R. V.; Cheng, A. L.; Vincent, J. J.; Crowley, M.; Tsui, V.; Gohlke, H.; Radmer, R. J.; Duan, Y.; Pitera, J.; Massova, I.; Seibel, G. L.; Singh, U. C.; Weiner, P. K.; Kollman, P. A. (2002), AMBER 7, University of California, San Francisco, herein incorporated by reference. The solvated system was optimized prior to the MD simulation. First, the protein-ligand was frozen and the solvent molecules with counterions were allowed to move during a 5000-step minimization with the conjugate gradient algorithm and a 5 ps MD run at T=300 K. After full relaxation and the entire solvated system was energy-minimized, the system was slowly heated from T=10 K to T=300 K in 30 ps before the production MD simulation for 500 ps. The full minimization and equilibration procedure was repeated for each mutant. The MD simulations were performed with a periodic boundary condition in the NPT ensemble at T=300 K with Berendsen temperature coupling and constant pressure (P=1 atm) with isotropic molecule-based scaling disclosed in Berendsen, H. C.; Postma, J. P. M.; van Gunsteren, W. F.; DiNola, A.; Haak, J. R. *J. Comp. Phys.* 1984, 81, 3684, herein incorporated by reference. The SHAKE algorithm of Ryckaert, J. P.; Ciccotti, G.; Berendsen, H. C. *J. Comp. Phys.* 1977, 23, 327 (herein incorporated by reference) was applied to fix all covalent bonds containing a hydrogen atom, a time step of 2 fs was used, and the non-bond pair list was updated every 10 steps. The pressure was adjusted by isotropic position scaling. The particle mesh Ewald (PME) method of Essmann, U.; Perera, L.; Berkowitz, M. L.; Darden, T. A.; Lee, H., Pedersen; L. G. *J. Chem. Phys.* 1995, 98, 10089, herein incorporated by reference, was used to treat long-range electrostatic interactions. A residue-based cutoff of 10 Å was applied to the noncovalent interactions. During the 500 ps production MD simulation, the coordinates of the simulated complex were saved every 1 ps.

Molecular docking and MD simulation procedures described above were performed to study cocaine binding with wild-type BChE and three mutants, i.e., A328W/Y332A, A328W/Y332A/Y419S, and A328W/Y332G. For each protein system (wild-type or mutant BChE), the protein binding with cocaine was considered in both the non-prereactive and prereactive enzyme-substrate complexes.

Most of the MD simulations in water were performed on a supercomputer, Superdome (shared-memory, with 4 nodes and 256 processors), at the Center for Computational Sciences, University of Kentucky. The other computations were carried out on SGI Fuel workstations and a 34-processors IBM x335 Linux cluster.

Experimental Procedure.

Site-directed mutagenesis of human BChE cDNA was performed by the QuikChange method of Braman, J.; Papworth, C.; Greener, A. *Methods Mol. Biol.* 1996, 57, 5731, herein incorporated by reference. Mutations were generated from wild-type human BChE in a pRc/CMV expression plasmid in accordance with Xie, W.; Altamirano, C. V.; Bartels, C. F.; Speirs, R. J.; Cashman, J. R.; Lockridge, O. *Mol. Pharmacol.* 1999, 55, 83, all herein incorporated by reference, kindly provided by Dr. Lockridge at University of Nebraska Medical Center. Using plasmid DNA as template and primers with specific base-pair alterations, mutations were made by polymerase chain reaction with Pfu DNA polymerase, for replication fidelity. The PCR product was treated with Dpn I endonuclease to digest the parental DNA template. Modified plasmid DNA was transformed into *Escherichia coli*, amplified, and purified. The DNA sequences of the mutants were confirmed by DNA sequencing. BChE mutants were expressed in human embryonic kidney cell line 293T/17. Cells were grown to 80-90% confluence in 6-well dishes and then transfected by Lipofectamine 2000 complexes of 4 μg plasmid DNA per each well. Cells were incubated at 37° C. in a $CO_2$ incubator for 24 hours and cells were moved to 60-mm culture vessel and cultured for four more days. The culture medium [10% fetal bovine serum in Dulbecco's modified Eagle's medium (DMEM)] was harvested for a BChE activity assay. To measure cocaine and benzoic acid, the product of cocaine hydrolysis by BChE, we used sensitive radiometric assays based on toluene extraction of [$^3$H]cocaine labeled on its benzene ring were used in accordance with Masson, P.; Xie, W., Froment, M-T.; Levitsky, V.; Fortier, P.-L.; Albaret, C.; Lockridge, O. *Biochim. Biophys. Acta* 1999, 1433, 281, herein incorporated by reference. In brief, to initiate reactions, 100 nCi of [$^3$H]cocaine was mixed with 100 μl of culture medium. Reactions proceeded at 37° C. for varying times. Reactions were stopped by adding 300 μl of 0.02 M HCl, which neutralized the liberated benzoic acid while ensuring a positive charge on the residual cocaine. [$^3$H]benzoic acid was extracted by 1 ml of toluene and measured by scintillation counting. Finally, the measured time-dependent radiometric data were fitted to the kinetic equation so that the catalytic efficiency ($k_{cat}/K_M$) was determined.

Depicted in FIG. 1 are plots of some important distances in the MD-simulated (−)-cocaine binding with A328W/Y332G BChE versus the simulation time, along with root-mean-square deviation (RMSD) of the coordinates of backbone atoms in the simulated structure from those in the X-ray crystal structure. MD trajectories for other complexes were similar to these two in FIG. 1, although the simulated average distances are different. Summarized in Table 2 are the average values of some important geometric parameters in the simulated complexes.

[a] Refers to (−)-cocaine binding with wild-type human BChE or (−)-cocaine binding with a mutant BChE, unless indicated otherwise.

[b] Refers to (+)-cocaine binding with wild-type human BChE.

[c]<D1>$_{non}$ and <D1> represent the average distances between the S198 $O^γ$ atom and the carbonyl carbon of the cocaine benzoyl ester in the simulated non-prereactive and prereactive BChE-cocaine complexes, respectively. <D2>, <D3>, <D4> refer to the average values of the simulated distances from the carbonyl oxygen of the cocaine benzoyl ester to the NH hydrogen atoms of G116, G117, and A199 residues, respectively. <0> is the average value of the dihedral angle formed by the S198 $O^γ$ atom and the plane of the carboxylate group of the cocaine benzoyl ester. See Scheme 2.

[d] The root-mean-square deviation (RMSD) of the coordinates of backbone atoms in the simulated structure from those in the X-ray crystal structure of BChE. "nonpre" and "pre" refer to the non-prereactive and prereactive BChE-cocaine complexes, respectively.

TABLE 2

| BChE-cocaine binding[a] | Average values of the geometric parameters[c] | | | | | | RMSD[d] | |
|---|---|---|---|---|---|---|---|---|
| | <D1>$_{non}$ | <D1> | <D2> | <D3> | <D4> | <Θ> | nonpre | pre |
| wild-type | 5.60 | 3.27 | 5.77 | 2.71 | 3.37 | 67 | 1.14 | 1.27 |
| wild-type with (+)-cocaine[b] | 7.64 | 3.69 | 2.88 | 2.30 | 2.83 | 61 | 1.15 | 1.13 |
| A328W/Y332A | 7.11 | 3.87 | 3.30 | 2.14 | 3.01 | 51 | 1.58 | 1.65 |
| A328W/Y332G | 7.06 | 3.96 | 2.28 | 2.52 | 2.42 | 60 | 1.20 | 1.35 |
| A328W/Y332A/Y419S | 5.18 | 5.84 | 5.64 | 4.56 | 6.97 | 164 | 2.66 | 2.62 |

[a]Refers to (−)-cocaine binding with wild-type human BChE or (−)-cocaine binding with a mutant BChE, unless indicated otherwise.

[b]Refers to (+)-cocaine binding with wild-type human BChE.

[c]<D1>$_{non}$ and <D1> represent the average distances between the S198 $O^γ$ atom and the carbonyl carbon of the cocaine benzoyl ester in the simulated non-prereactive and prereactive BChE-cocaine complexes, respectively. <D2>, <D3>, <D4> refer to the average values of the simulated distances from the carbonyl oxygen of the cocaine benzoyl ester to the NH hydrogen atoms of G116, G117, and A199 residues, respectively. <Θ> is the average value of the dihedral angle formed by the S198 $O^γ$ atom and the plane of the carboxylate group of the cocaine benzoyl ester. See Scheme 2.

[d]The root-mean-square deviation (RMSD) of the coordinates of backbone atoms in the simulated structure from those in the X-ray crystal structure of BChE. "nonpre" and "pre" refer to the non-prereactive and prereactive BChE-cocaine complexes, respectively.

Figure 2:
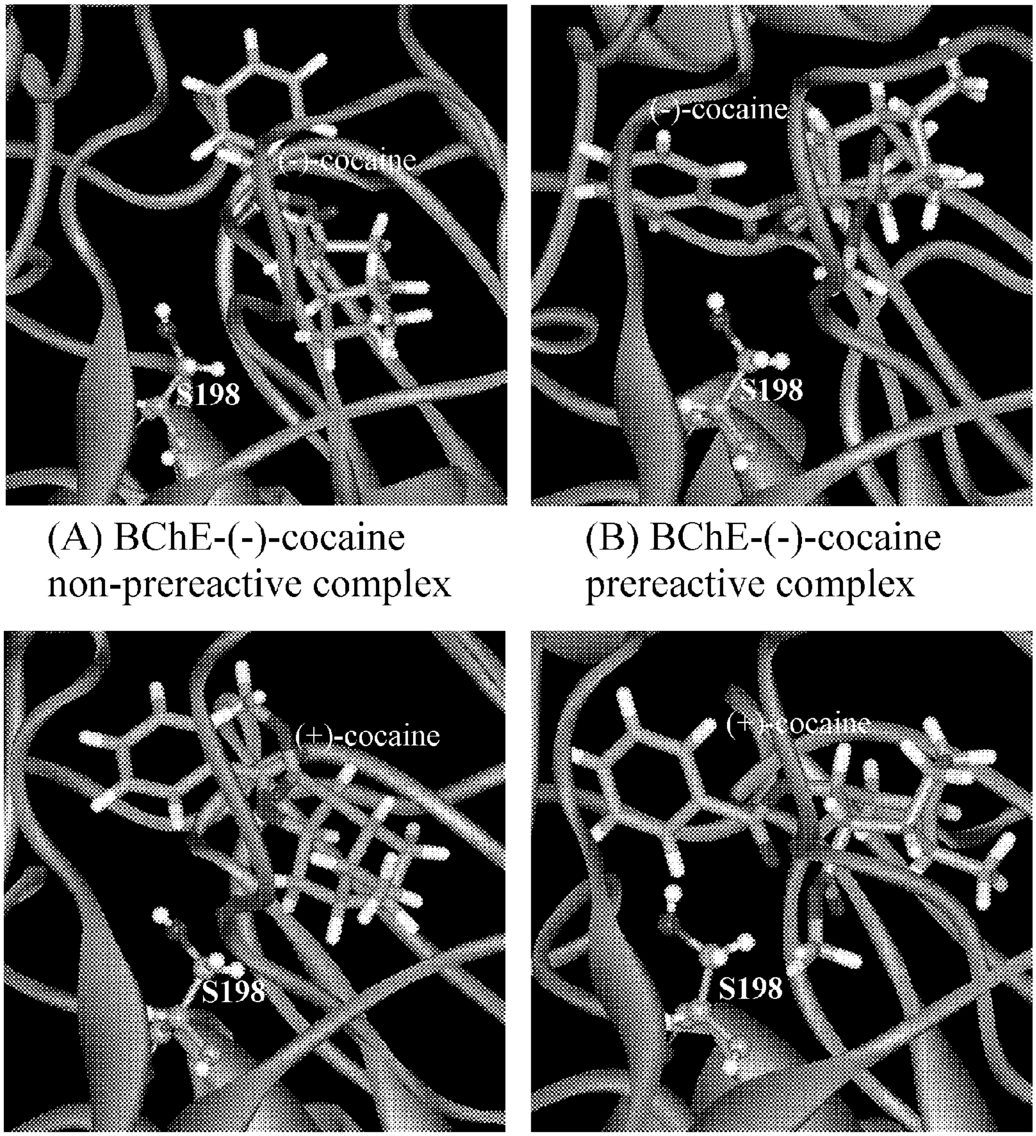

FIG. 2 shows the binding structures of the simulated non-prereactive and prereactive complexes of wild-type BChE binding with the two enantiomers of cocaine. In the non-prereactive complexes with (−)- and (+)-cocaine, the methyl ester group of cocaine is positioned at the top of the H438 backbone, while the cocaine benzoyl ester moiety is quasi-parallel to the C—$O^γ$ side chain of S198 with a dihedral angle Θ of −8° and 140°, respectively.

Scheme 2. Hydrolysis of (-)-cocaine and (+)-cocaine.

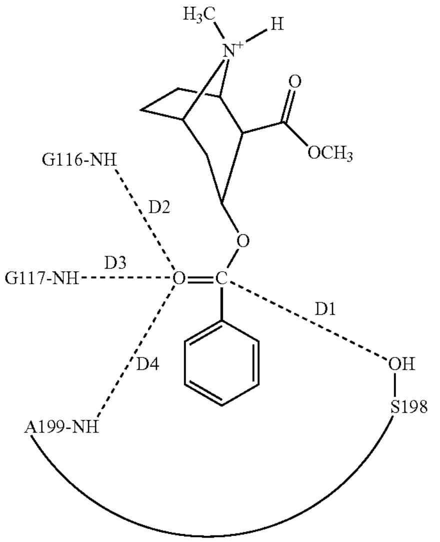

Here, Θ refers to the dihedral angle formed by S198 $O^γ$ and the plane of carboxylate group of the cocaine benzoyl ester as shown in the structure diagram below.

The simulated internuclear distances between the carbonyl oxygen of cocaine benzoyl ester group and the NH hydrogen of G116, G117, and A199 are comparable for the two enantiomers. The simulated average distances between the carbonyl carbon of the benzoyl ester and S198 $O^γ$ are 5.60 Å and 5.18 Å for (−)- and (+)-cocaine, respectively. Comparing the simulated protein backbone structures to the X-ray crystal structure of Nicolet et al, one can see from FIG. 1 that the RMSD values are all smaller than 1.3 Å for the whole protein structures.

The MD simulations of the prereactive complexes reveal that wild-type BChE binding with (−)-cocaine is essentially the same as the binding with (+)-cocaine in the binding site, except for the different positions of methyl ester group of the substrates. The simulated average distances between the carbonyl carbon of the benzoyl ester and S198 $O^γ$ are 3.27 and 3.69 Å for (−)-cocaine and (+)-cocaine, respectively. Moreover, the (+)-cocaine is stabilized more effectively by the formation of strong hydrogen bonds with the backbone NH of residues G116, G117, and A199 as summarized above in Table 2. The cocaine benzoyl ester moiety is positioned quasi-perpendicular to S198 C—$O^γ$ with a dihedral angle Θ of ~67° and ~61° for (−)- and (+)-cocaine, respectively.

A comparison was made between the currently simulated structures of the BChE-cocaine binding with those simulated previously by using a homology model of BChE and it was noted that two major differences between the two sets of structures. By using the X-ray crystal structure in accordance with Nicolet et al, the acyl loop is positioned on the top of the cocaine benzoyl ester moiety of the cocaine, whereas the acyl loop is far from the cocaine benzoyl ester moiety in the structure simulated starting from the homology model of Zhan et al. The RMSD of the coordinates of backbone atoms in the previously simulated prereactive BChE-(−)-cocaine complex from those in the X-ray crystal structure of BChE is ~2.0 Å for the entire protein and ~3.0 Å for the acyl loop. The RMSD value became ~2.4 Å for the entire protein and ~3.3 Å for the acyl loop, when the X-ray crystal structure was replaced by the MD-simulated prereactive BChE-(−)-cocaine complex starting from the X-ray crystal structure. Despite these structural differences, the benzoyl ester group of the ligand is still close to the key residues (S197, G116, and G117) in the BChE binding site. Some significant differences are associated with the distances between the S198 $O^{\gamma}$ atom and the carbonyl carbon of the cocaine benzoyl ester in non-prereactive complexes. The average values of this distance in the non-prereactive complexes were ~9.5 and ~8.5 Å for (−)- and (+)-cocaine, respectively, when a homology model was used. Using the X-ray crystal structure to conduct the analysis, corresponding average values became ~5.6 and ~5.2 Å, respectively. Therefore, both (−)- and (+)-cocaine became closer to the binding site when the homology model was replaced by the X-ray crystal structure. However, no significant changes of the binding in the prereactive complexes were observed when the used homology model was replaced by the X-ray crystal structure. The average values of the simulated distance between the S198 $O^{\gamma}$ atom and the carbonyl carbon of the cocaine benzoyl ester in the prereactive complexes are always close to ~3.5 Å for both (−)- and (+)-cocaine no matter whether the X-ray crystal structure or homology model of BChE was used as the starting structure. The similar computational results obtained from the use of the X-ray crystal structure and homology model of BChE provides evidence that the fundamental structural and mechanistic insights obtained from the previous computational studies of Zhan et al are reliable, despite the previous simulations were performed by using the homology model when the X-ray crystal structure was not available.

Figure 3:
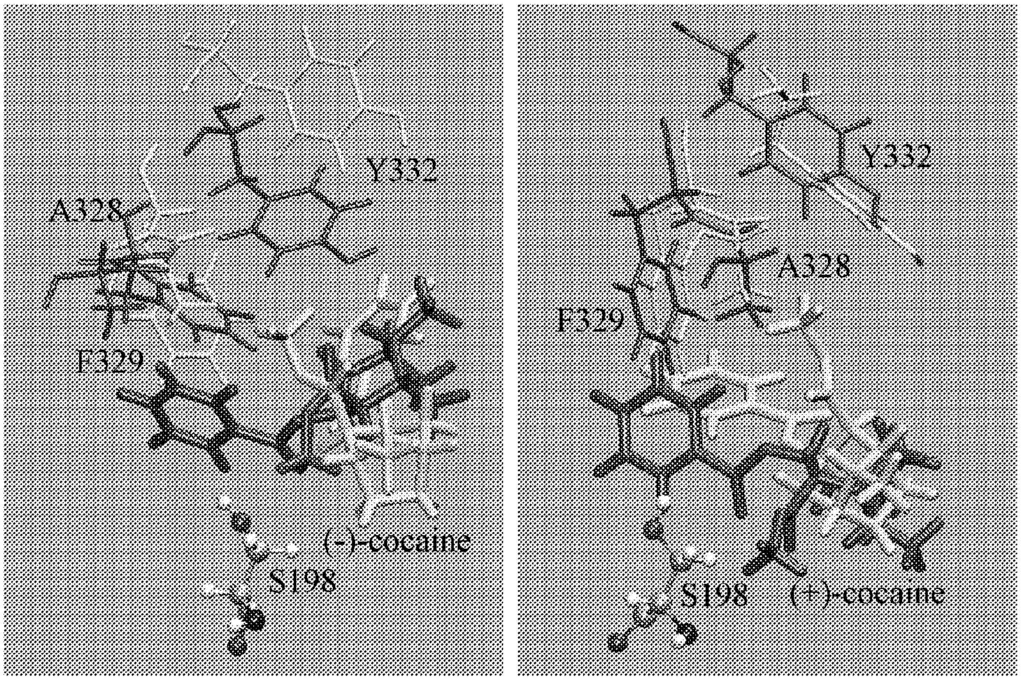
FIG. 3A shows the (−)-cocaine rotation in the BChE active site for the non-prereactive complex to the prereactive complex hindered by some residues at positions Y332, A328, and F329 residues in the non-prereactive complexes which are significantly different from the corresponding positions in the prereactive complex.
FIG. 3B shows the (+)-cocaine rotation in the BChE active site where none of the aforementioned residues hinders the (+)-cocaine rotation in the BChE active site from the non-prereactive complex to the prereactive complex in accordance with the present invention.

Further, the simulated structures of the non-prereactive BChE-cocaine complexes were superimposed with the corresponding prereactive complexes. As shown in FIG. 3, the (−)-cocaine rotation in the BChE active site from the non-prereactive complex to the prereactive complex is hindered by some residues as the positions of Y332, A328, and F329 residues in the non-prereactive complex are significantly different from the corresponding positions in the prereactive complex, whereas none of these residues hinders the (+)-cocaine rotation in the BChE active site from the non-prereactive complex to the prereactive complex because these residues stay in nearly the same positions in the two BChE-(+)-cocaine complexes.

(−)-Cocaine Binding with BChE Mutants.

Now that the (−)-cocaine rotation from the non-prereactive complex to the prereactive complex has been known to be the rate-determining step of the BChE-catalyzed hydrolysis of (−)-cocaine as shown by Zhan et al, useful BChE mutants should be designed to specifically accelerate the change from the non-prereactive BChE-(−)-cocaine complex to the prereactive complex. The question is whether MD simulation can be performed to help design BChE mutants that have higher catalytic activity for (−)-cocaine hydrolysis.

Figure 4:
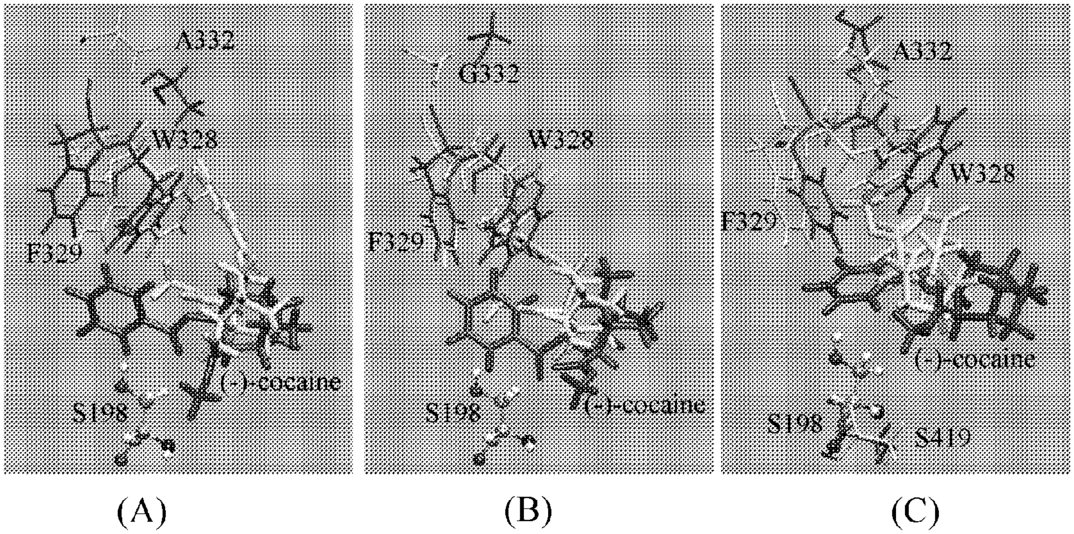
FIG. 4A depicts the (−)-cocaine rotation in the active site of A328W/Y332A.
FIG. 4B depicts the (−)-cocaine rotation in the active site of A328W/Y332G BChE from the non-preactive complex to the prereactive complex.
FIG. 4C depicts the (−)-cocaine rotation in the active site of wild-type BChE.

In the simulated non-prereactive complex, the average distance between the carbonyl carbon of cocaine benzoyl ester and S198 $O^{\gamma}$ is 7.6 Å for A328W/Y332A BChE and 7.1 Å for A328W/Y332G BChE, as seen in Table 2 above. In the simulated prereactive complex, the average values of this important internuclear distance become 3.87 and 3.96 Å for A328W/Y332A and A328W/Y332G BChE's, respectively. Compared to the simulated wild-type BChE-(−)-cocaine prereactive complex, the average distances between the carbonyl carbon of the cocaine benzoyl ester and S198 $O^{\gamma}$ in the prereactive complex of (−)-cocaine with A328W/Y332A and A328W/Y332G BChE's are all slightly longer, whereas the average distances between the carbonyl oxygen of the cocaine benzoyl ester and the NH of G116, G117, and A199 residues are all shorter. This provides evidence that (−)-cocaine more strongly bind with A328W/Y332A and A328W/Y332G BChE's in the prereactive complexes. More importantly, the (−)-cocaine rotation in the active site of A328W/Y332A and A328W/Y332G BChE's from the non-prereactive complex to the prereactive complex did not cause considerable changes of the positions of A332 (or G332), W328, and F329 residues as seen in FIG. 4, compared to the (−)-cocaine rotation in the active site of wild-type BChE. These results provide evidence that A328W/Y332A and A328W/Y332G BChE's should be associated with lower energy barriers than the wild-type for the (−)-cocaine rotation from the non-prereactive complex to the prereactive complex. Further, (−)-cocaine binding with A328W/Y332G BChE is very similar to the binding with A328W/Y332A BChE, but the position change of F329 residue caused by the (−)-cocaine rotation was significant only in A328W/Y332A BChE, thus suggesting that the energy barrier for the (−)-cocaine rotation in A328W/Y332G BChE should be slightly lower than that in A328W/Y332A BChE.

Concerning (−)-cocaine binding with A328W/Y332A/Y419S BChE, Y419 stays deep inside the protein and does not directly contact with the cocaine molecule. The Y419S mutation was tested because it was initially expected that this mutation would further increase the free space of the active site pocket so that the (−)-cocaine rotation could be easier. However, as seen in Table 2 above, the average distance between the carbonyl carbon of cocaine benzoyl ester and S198 $O^{\gamma}$ atom in the simulated prereactive complex was as long as 5.84 Å. The average distances between the carbonyl oxygen of the cocaine benzoyl ester and the NH hydrolysis atoms of G116, G117, and A199 residues are between 4.56 and 6.97 Å; no any hydrogen bond between them. In addition to the internuclear distances, another interesting geometric parameter is the dihedral angle, 0, formed by S198 $O^{\gamma}$ and the plane of the carboxylate group of the cocaine benzoyl ester. As seen in Table 2, the $\Theta$ values in the prereactive complexes of cocaine with wild-type BChE and all of the BChE mutants other than A328W/Y332A/Y419S BChE all slightly deviate from the ideal value of 90° for the nucleophilic attack of S198 $O^{\gamma}$ at the carbonyl carbon of cocaine. The 0 value in the prereactive complex of (−)-cocaine with A328W/Y332A/Y419S BChE is 164°, which is considerably different from the ideal value of 900.

Catalytic Activity.

The aforementioned discussion provides evidence that the energy barriers for the (−)-cocaine rotation in A328W/Y332A and A328W/Y332G BChE's from the non-prereactive complex to the prereactive complex, the rate-determining step for the BChE-catalyzed hydrolysis of (−)-cocaine, should be lower than that in the wild-type BChE. Thus, the MD simulations predict that both A328W/Y332A and A328W/Y332G BChE's should have a higher catalytic activity than the wild-type BChE for (−)-cocaine hydrolysis. Further, the MD simulations also suggest that the energy barrier for the (−)-cocaine rotation in A328W/Y332G BChE should be slightly lower than that in A328W/Y332A BChE and, therefore, the catalytic activity of A328W/Y332G BChE for the (−)-cocaine hydrolysis should be slightly higher than the activity of A328W/Y332A BChE. In addition, the MD simulations predict that A328W/Y332A/Y419S BChE should have no catalytic activity, or have a considerably lower catalytic activity than the wild-type, for (−)-cocaine hydrolysis because (−)-cocaine binds with the mutant BChE in a way that is not suitable for the catalysis.

The catalytic efficiency ($k_{cat}/K_M$) of A328W/Y332A BChE for (−)-cocaine hydrolysis was reported to be $8.56\times10^6$ M $min^{-1}$, which is 9.39 times of the $k_{cat}/K_M$ value ($9.11\times10^5$ M $min^{-1}$) of the wild-type BChE. To examine these theoretical predictions of the relative activity for A328W/Y332G and A328W/Y332A/Y419S BChE's, a A328W/Y332A, A328W/Y332G, and A328W/Y332A/Y419S BChE was produced through site-directed mutagenesis. To minimize the possible systematic experimental errors of the kinetic data, kinetic studies were performed with all of three mutants under the same condition and compared the catalytic efficiency of the A328W/Y332G and A328W/Y332A/Y419S to that of the A328W/Y332A for (−)-cocaine hydrolysis at benzoyl ester group. Based on the kinetic analysis of the measured time-dependent radiometric data, the ratio of the $k_{cat}/K_M$ value of A328W/Y332G BChE to the $k_{cat}/K_M$ value of A328W/Y332A BChE for the (−)-cocaine hydrolysis was determined to be ~2.08, or A328W/Y332G BChE has a $k_{cat}/K_M$ value of ~$1.78\times10^7$ M $min^{-1}$ for the (−)-cocaine hydrolysis. The radiometric data show no significant catalytic activity for A328W/Y332A/Y419S BChE. These experimental data are consistent with the theoretical predictions based on the MD simulations.

Conclusion.

Molecular modeling, molecular docking, and molecular dynamics (MD) simulations were performed to study cocaine binding with human butyrylcholinesterase (BChE) and its mutants, based on a recently reported X-ray crystal structure of human BChE. The MD simulations of cocaine binding with wild-type BChE led to average BChE-cocaine binding structures similar to those obtained recently from the MD simulations based on a homology model of BChE, despite the significant difference found at the acyl binding pocket. This confirms the fundamental structural and mechanistic insights obtained from the prior computational studies of Zhan et al based on a homology model of BChE, e.g., the rate-determining step for BChE-catalyzed hydrolysis of biologically active (−)-cocaine is the (−)-cocaine rotation in the BChE active site from the non-prereactive BChE-(−)-cocaine complex to the prereactive complex.

The MD simulations further reveal that the (−)-cocaine rotation in the active site of wild-type BChE from the non-prereactive complex to the prereactive complex is hindered by some residues such that the positions of Y332, A328, and F329 residues in the non-prereactive complex are significantly different from those in the prereactive complex. Compared to (−)-cocaine binding with wild-type BChE, (−)-cocaine more strongly bind with A328W/Y332A and A328W/Y332G BChE's in the prereactive complexes. More importantly, the (−)-cocaine rotation in the active site of A328W/Y332A and A328W/Y332G BChE's from the non-prereactive complex to the prereactive complex did not cause considerable changes of the positions of A332 or G332, W328, and F329 residues. These results provide evidence that A328W/Y332A and A328W/Y332G BChE's are associated with lower energy barriers than wild-type BChE for the (−)-cocaine rotation from the non-prereactive complex to the prereactive complex. Further, (−)-cocaine binding with A328W/Y332G BChE is very similar to the binding with A328W/Y332A BChE, but the position change of F329 residue caused by the (−)-cocaine rotation was significant only in A328W/Y332A BChE, thus suggesting that the energy barrier for (−)-cocaine rotation in A328W/Y332G BChE should be slightly lower than that in A328W/Y332A BChE. It has also been demonstrated that (−)-cocaine binds with A328W/Y332A/Y419S BChE in a way that is not suitable for the catalysis.

Based on the computational results, both A328W/Y332A and A328W/Y332G BChE's have catalytic activity for (−)-cocaine hydrolysis higher than that of wild-type BChE and the activity of A328W/Y332G BChE should be slightly higher than that of A328W/Y332A BChE, whereas A328W/Y332A/Y419S BChE is expected to lose the catalytic activity. The computational predictions are completely consistent with the experimental kinetic data, providing evidence that the used computational protocol, including molecular modeling, molecular docking, and MD simulations, is reliable in prediction of the catalytic activity of BChE mutants for (−)-cocaine hydrolysis.

Experiment 2

MD Simulations and Quantum Mechanical/Molecular Mechanical (QM/MM) Calculations Relating to A199S/A328W/Y332G Mutant (Mutant 1) (SEQ ID NO: 1)

Generally speaking, for rational design of a mutant enzyme with a higher catalytic activity for a given substrate, one needs to design a mutation that can accelerate the rate-determining step of the entire catalytic reaction process while the other steps are not slowed down by the mutation. Reported computational modeling and experimental data indicated that the formation of the prereactive BChE-(−)-cocaine complex (ES) is the rate-determining step of (−)-cocaine hydrolysis catalyzed by wild-type BChE as disclosed by Sun et al, Zhan et al and Hamza, A.; Cho, H.; Tai, H.-H.; Zhan, C.-G. *J. Phys. Chem. B* 2005, 109, 4776, herein incorporated by reference, whereas the rate-determining step of the corresponding (+)-cocaine hydrolysis is the chemical reaction process consisting of four individual reaction steps disclosed by Zhan et al and shown in Scheme 3 and Scheme 4 below.

Scheme 3. Schematic representation of BChE-catalyzed hydrolysis of (-)-cocaine.
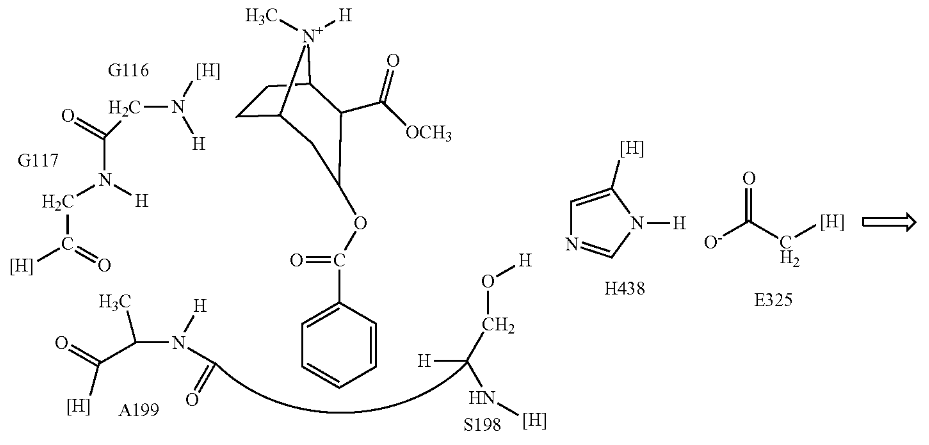
ES
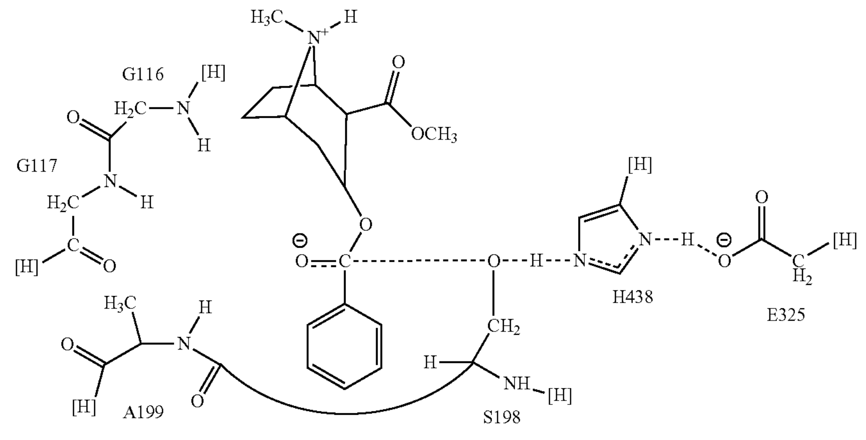
TS1
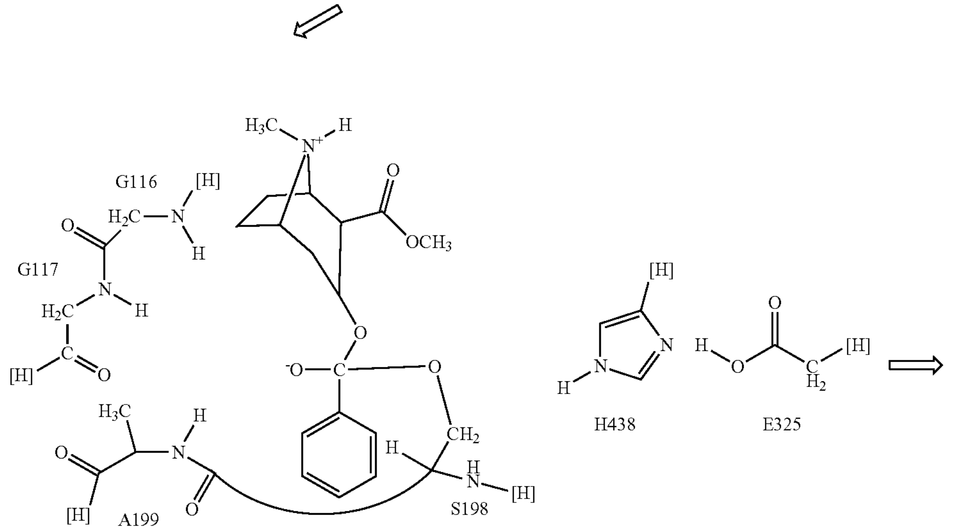
INT1

-continued
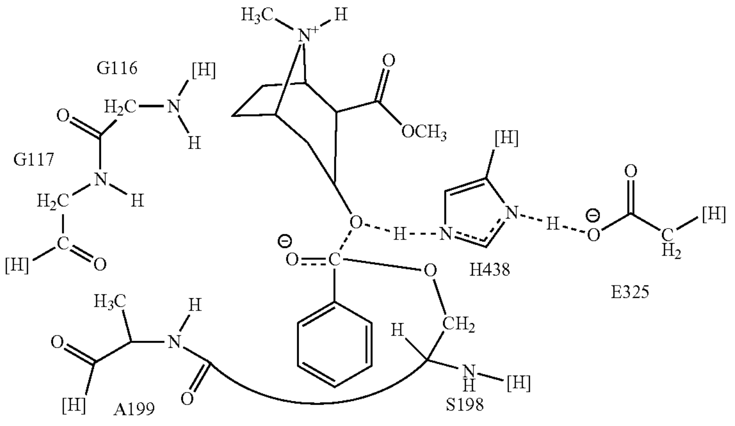
TS2
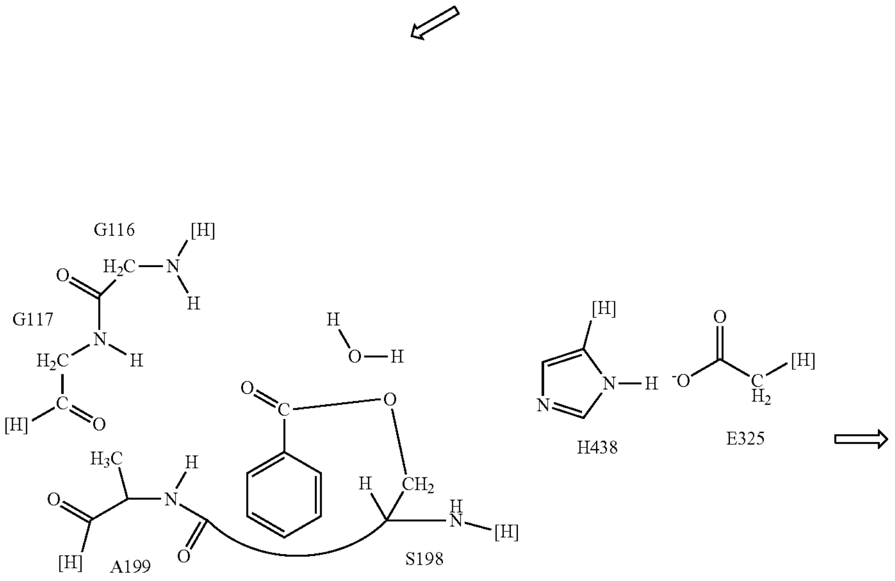
INT2
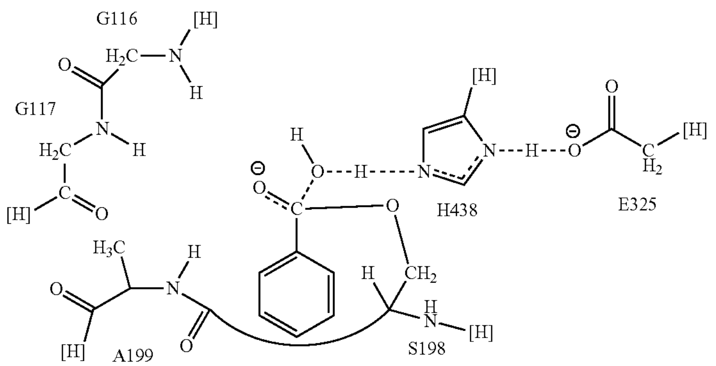
TS3

-continued

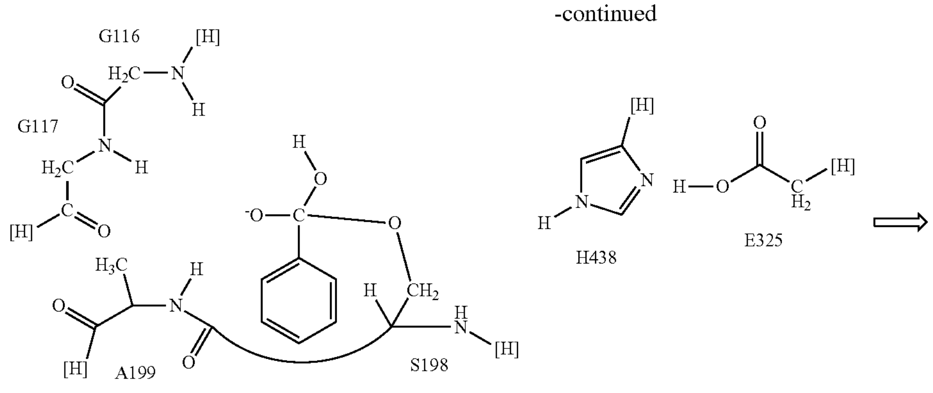

INT3

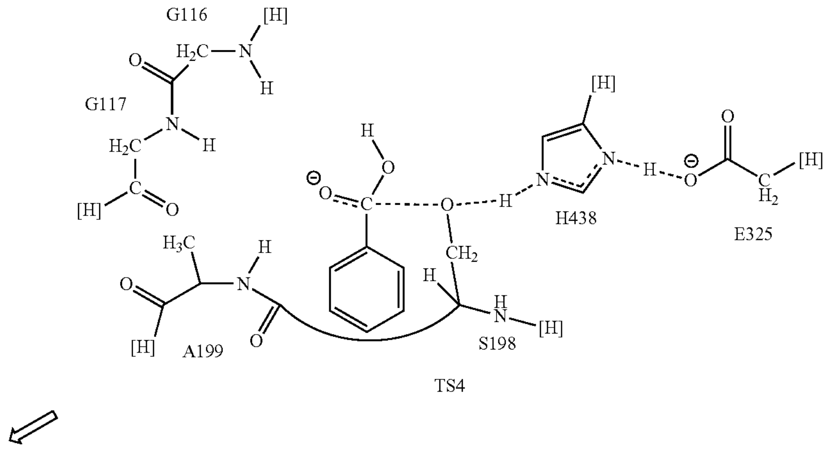

TS4

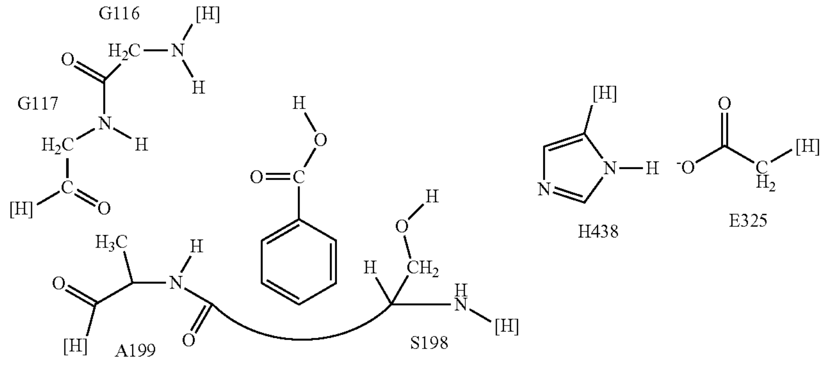

EB

Scheme 3. Schematic representation of BChE-catalyzed hydrolysis of (−)-cocaine. Only QM-treated high-layer part of the reaction system in the QM/MM calculations are drawn. Notation [H] refers to a non-hydrogen atom in the MM-treated low-layer part of the protein and the cut covalent bond with this atom is saturated by a hydrogen atom. The dash lines in the transition state structures represent the transition bonds.

This mechanistic understanding is consistent with the experimental observation of Sun et al, that the catalytic rate constant of wild-type BChE against (+)-cocaine is pH-dependent, whereas that of the same enzyme against (−)-cocaine is independent of the pH. The pH-dependence of the rate constant for (+)-cocaine hydrolysis is clearly associated with the protonation of H438 residue in the catalytic triad (S198, H438, and E325). For the first and third steps of the reaction process, when H438 is protonated, the catalytic triad cannot function and, therefore, the enzyme becomes inactive. The lower the pH of the reaction solution is, the higher the concentration of the protonated H438 is, and the lower the concentration of the active enzyme is. Hence, the rate constant was found to decrease with decreasing the pH of the reaction solution for the enzymatic hydrolysis of (+)-cocaine.

Based on the above mechanistic understanding, the efforts for rational design of the BChE mutants reported in literature have been focused on how to improve the ES formation process. Indeed, several BChE mutants, including A328W, A328W/Y332A, A328W/Y332G, and F227A/S287G/A328W/Y332M, have been found to have a significantly higher catalytic efficiency ($k_{cat}/K_M$) against (−)-cocaine; these mutants of BChE have an approximate 9 to 34-fold improved catalytic efficiency against (−)-cocaine. Experimental observation also indicated that the catalytic rate constant of A328W/Y332A BChE is pH-dependent for both (−)- and (+)-cocaine. The pH-dependence reveals that for both (−)- and (+)-cocaine, the rate-determining step of the hydrolysis catalyzed by A328W/Y332A BChE should be either the first or the third step of the reaction process. Further, if the third step were rate determining, then the catalytic efficiency of the A328W/Y332A mutant against (−)-cocaine should be as high as that of the same mutant against (+)-cocaine because the (−)- and (+)-cocaine hydrolyses share the same third and fourth steps (see Scheme 3). However, it has also been observed that the A328W/Y332A mutant only has a ~9-fold improved catalytic efficiency against (−)-cocaine, whereas the A328W/Y332A mutation does not change the high catalytic activity against (+)-cocaine. This analysis of the experimental and computational data available in literature clearly shows that the rate-determining step of (−)-cocaine hydrolysis catalyzed by the A328W/Y332A mutant should be the first step of the chemical reaction process. Further, recently reported computational modeling also suggests that the formation of the prereactive BChE-(−)-cocaine complex (ES) is hindered mainly by the bulky side chain of Y332 residue in wild-type BChE, but the hindering can be removed by the Y332A or Y332G mutation. Therefore, starting from the A328W/Y332A or A328W/Y332G mutant, the truly rational design of further mutation(s) to improve the catalytic efficiency of BChE against (−)-cocaine should aim to decrease the energy barrier for the first reaction step without significantly affecting the ES formation and other chemical reaction steps.

The following rational design of a high-activity mutant of BChE against (−)-cocaine is based on detailed computational modeling of the transition state for the rate-determining step (i.e., the first step of the chemical reaction process). Molecular dynamics (MD) simulations and hybrid quantum mechanical/molecular mechanical (QM/MM) calculations were performed to model the protein environmental effects on the stabilization of the transition-state structure for BChE-catalyzed hydrolysis of (−)-cocaine. The simulated and calculated results indicate that the transition-state structure can be stabilized better by the protein environment in A199S/A328W/Y332G mutant of BChE than that in the wild-type. The computational modeling led to a prediction of the higher catalytic efficiency for the A199S/A328W/Y332G mutant against (−)-cocaine. The prediction has been confirmed by wet experimental tests showing that the A199S/A328W/Y332G mutant has a significantly improved catalytic efficiency against (−)-cocaine. All of the obtained results clearly demonstrate that directly modeling the transition-state structure provides a reliable computational approach to the rational design of a high-activity mutant of BChE against (−)-cocaine.

MD Simulations.

It should be stressed that a critical issue exists with regard to any MD simulation on a transition state. In principle, MD simulation using a classical force field (molecular mechanics) can only simulate a stable structure corresponding to a local minimum on the potential energy surface, whereas a transition state during a reaction process is always associated with a first-order saddle point on the potential energy surface. Hence, MD simulation using a classical force field cannot directly simulate a transition state without any restraint on the geometry of the transition state. Nevertheless, if one can technically remove the freedom of imaginary vibration in the transition state structure, then the number of vibrational freedoms (normal vibration modes) for a nonlinear molecule will decrease from 3N-6. The transition state structure is associated with a local minimum on the potential energy surface within a subspace of the reduced vibrational freedoms, although it is associated with a first-order saddle point on the potential energy surface with all of the 3N-6 vibrational freedoms. Theoretically, the vibrational freedom associated with the imaginary vibrational frequency in the transition state structure can be removed by appropriately freezing the reaction coordinate. The reaction coordinate corresponding to the imaginary vibration of the transition state is generally characterized by a combination of some key geometric parameters. These key geometric parameters are bond lengths of the forming and breaking covalent bonds for BChE-catalyzed hydrolysis of cocaine, as seen in Scheme 3. Thus, one just needs to maintain the bond lengths of the forming and breaking covalent bonds during the MD simulation on a transition state. Technically, one can maintain the bond lengths of the forming and breaking covalent bonds by simply fixing all atoms within the reaction center, by using some constraints on the forming and breaking covalent bonds, or by redefining the forming and breaking covalent bonds. It should be pointed out that the only purpose of performing such type of MD simulation on a transition state is to examine the dynamic change of the protein environment surrounding the reaction center and the interaction between the reaction center and the protein environment. For this study, of interest is the simulated structures, as the total energies calculated in this way are meaningless.

The initial BChE structures used in the MD simulations were prepared based on the previous MD simulation in accordance with Hamza et al on the prereactive ES complex for wild-type BChE with (−)-cocaine in water by using Amber7 program package. The previous MD simulations on the prereactive BChE-(−)-cocaine complex (ES) started from the X-ray crystal structure of Nicolet et al deposited in the Protein Data Bank (pdb code: 1P0P). The present MD simulation on the transition state for the first step (TS1) was performed in such a way that bond lengths of the partially formed and partially broken covalent bonds in the transition state were all constrained to be the same as those obtained from our previous ab initio reaction coordinate calculations on the model reaction system of wild-type BChE in accordance with Zhan et al. The partially formed and partially broken covalent bonds in the transition state will be called "transition" bonds below, for convenience. A sufficiently long MD simulation with the transition bonds constrained should lead to a reasonable protein environment stabilizing the reaction center in the transition-state structure simulated. Further, the simulated TS1 structure for wild-type BChE with (−)-cocaine was used to build the initial structures of TS1 for the examined BChE mutants with (−)-cocaine; only the side chains of mutated residues needed to be changed.

The partial atomic charges for the non-standard residue atoms, including cocaine atoms, in the TS1 structures were calculated by using the RESP protocol implemented in the Antechamber module of the Amber7 package following electrostatic potential (ESP) calculations at ab initio HF/6-31G* level using Gaussian03 program known in the art. The geometries used in the ESP calculations came from those obtained from the previous ab initio reaction coordinate calculations of Zhan et al, but the functional groups representing the oxyanion hole were removed. Thus, residues G116, G117, and A199 were the standard residues as supplied by Amber7 in the MD simulations. The general procedure for carrying out the MD simulations in water is essentially the same as that used in our previously reported other computational studies including Zhan et al, Hamza et al and (a) Zhan, C.-G.; Norberto de Souza, O.; Rittenhouse, R.; Ornstein, R. L. *J. Am. Chem. Soc.* 1999, 121, 7279, (b) Koca, J.; Zhan, C.-G.; Rittenhouse, R.; Ornstein, R. L. *J. Am. Chem. Soc.* 2001, 123, 817, (c) Koca, J.; Zhan, C.-G.; Rittenhouse, R. C.; Ornstein, R. L. *J Comput. Chem.* 2003, 24, 368, (d) Hamza, A.; Cho, H.; Tai, H.-H.; Zhan, C.-G. *Bioorg. Med. Chem.* 2005, 13, 4544, herein all incorporated by reference. Each aforementioned starting TS1 structure was neutralized by adding chloride counterions and was solvated in a rectangular box of TIP3P water molecules with a minimum solute-wall distance of 10 Å as described by Jorgensen, W. L.; Chandrasekhar, J.; Madura, J.; Klein, M. L. *J. Chem. Phys.* 1983, 79, 926, herein incorporated by reference. The total numbers of atoms in the solvated protein structures for the MD simulations are nearly 70,000, although the total number of atoms of BChE and (−)-cocaine is only 8417 (for the wild-type BChE). All of the MD simulations were performed by using the Sander module of Amber7 package. The solvated systems were carefully equilibrated and fully energy minimized. These systems were gradually heated from T=10 K to T=298.15 K in 30 ps before running the MD simulation at T=298.15 K for 1 ns or longer, making sure that a stable MD trajectory was obtained for each of the simulated TS1 structures. The time step used for the MD simulations was 2 fs. Periodic boundary conditions in the NPT ensemble at T=298.15 K with Berendsen temperature coupling and P=1 atm with isotropic molecule-based scaling were applied. The SHAKE algorithm was used to fix all covalent bonds containing hydrogen atoms. The non-bonded pair list was updated every 10 steps. The particle mesh Ewald (PME) method in accordance with Essmann, U.; Perera, L.; Berkowitz, M. L.; Darden, T. A.; Lee, H., Pedersen, L. G. *J. Chem. Phys.* 1995, 98, 10089, herein incorporated by reference, was used to treat long-range electrostatic interactions. A residue-based cutoff of 10 Å was utilized to the non-covalent interactions. The coordinates of the simulated systems were collected every 1 ps during the production MD stages.

QM/MM Calculations.

For each TS1 structure examined, after the MD simulation was completed and a stable MD trajectory was obtained, all of the collected snapshots of the simulated structure, excluding those before the trajectory was stabilized, were averaged and further energy-minimized. The energy-minimized average structure (with the transition bonds constrained) was used as an initial geometry to carry out a further geometry optimization by using the ONIOM approach of Dapprich, S.; Komaromi, I.; Byun, K. S.; Morokuma, K.; Frisch, M. J. *J. Mol. Struct.* (*Theochem*) 1999, 461, 1-21, herein incorporated by reference, implemented in the Gaussian03 program of Frisch, M. J. et al *Gaussian* 03, Revision A. 1, Gaussian, Inc., Pittsburgh, Pa., 2003, herein incorporated by reference. Two layers were defined in the present ONIOM calculation: the high layer, as depicted in Scheme 3 above, was calculated quantum mechanically at the ab initio HF/3-21G level, whereas the low layer was calculated molecular mechanically by using the Amber force field as used in our MD simulation and energy minimization with the Amber7 program. The ONIOM calculations at the HF/3-21G:Amber level in this study are a type of QM/MM calculations of Vreven, T.; Morokuma, K. *J. Chem. Phys.* 2000, 113, 2969-2975 and Frisch, M.; Vreven, T.; Schlegel, H. B.; Morokuma, K. *J. Comput. Chem.* 2003, 24, 760-769, herein both incorporated by reference. Previous reaction coordinate calculations with an active site model of wild-type BChE demonstrate that the HF/3-21G level is adequate for the geometry optimization of this enzymatic reaction system shown by Zhan et al, although the final energy calculations for calculating the energy barriers must be carried out at a higher level. As depicted in Scheme 3, for all of these QM/MM calculations, the same part of the enzyme was included in the QM-treated high layer. So, the QM-treated high layer included (−)-cocaine, key functional groups from the catalytic triad (S198, H438, and E325), and the three residues, i.e., G116, G117, and A199 (or S199 for a particular mutant, see Scheme 4), of the possible oxyanion hole, whereas the entire enzyme structure of BChE was included in the MM-treated low layer. A language computer program was developed to automatically generate the input files for the ONIOM calculations following the MD simulations and subsequent energy minimizations in order to make sure that the atom types used for all low-layer atoms are the same as what were used in the Amber7. During the TS1 geometry optimization using the two-layer ONIOM, the length of a key transition C—O bond was fixed which dominates the reaction coordinate; all of the other transition bond lengths were relaxed. The C and O atoms in the key transition C—O bond are the carbonyl carbon of (−)-cocaine benzoyl ester and the $O^{\gamma}$ atom of S198, respectively, according to the previous reaction coordinate calculations with an active site model of wild-type BChE of Zhan et al.

Most of the MD simulations and QM/MM calculations were performed in parallel on an HP supercomputer (Superdome, with 256 shared-memory processors) at the Center for Computational Sciences, University of Kentucky. Some of the computations were carried out on a 34-processors IBM x335 Linux cluster and SGI Fuel workstations.

Scheme 4.
Schematic representation of the first reaction step for (-)-cocaine hydrolysis catalyzed by a BChE mutant with an A199S mutation.
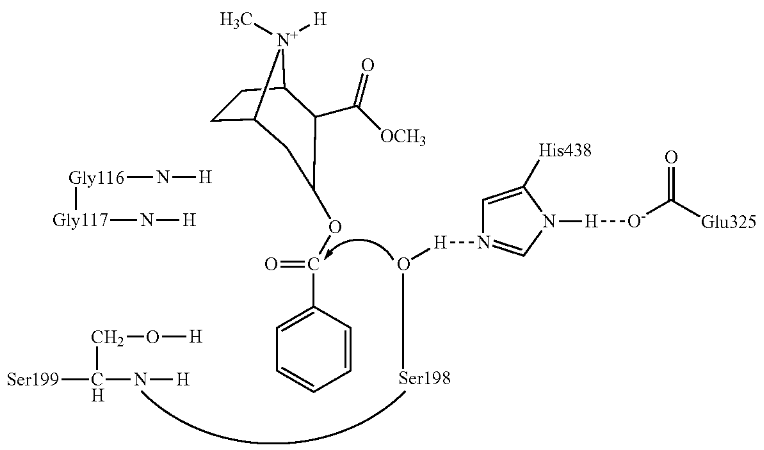
ES
TS1
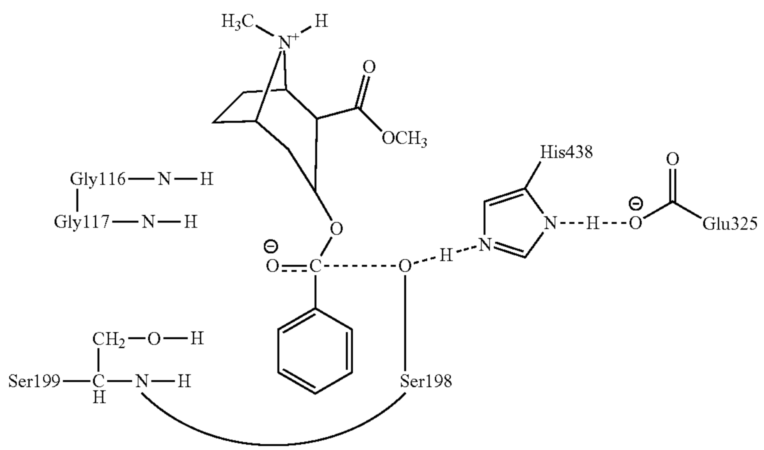

-continued

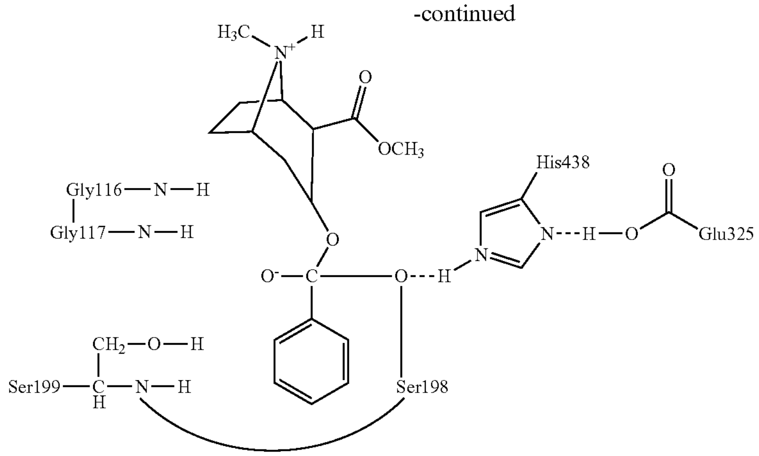

INT1

Scheme 4. Schematic representation of the first reaction step for (−)-cocaine hydrolysis catalyzed by a BChE mutant with an A199S mutation.

Experimental Materials.

Cloned pfu DNA polymerase and Dpn I endonuclease were obtained from Stratagene (La Jolla, Calif.). $^{3}$H-(−)-cocaine (50 Ci/mmol) was purchased from PerkinElmer Life Sciences (Boston, Mass.). The expression plasmid pRc/CMV was a gift from Dr. O. Lockridge, University of Nebraska Medical Center (Omaha, Nebr.). All oligonucleotides were synthesized by the Integrated DNA Technologies, Inc. The QIAprep Spin Plasmid Miniprep Kit and Qiagen plasmid purification kit and QIAquick PCR purification kit were obtained from Qiagen (Santa Clarita, Calif.). Human embryonic kidney 293T/17 cells were from ATCC (Manassas, Va.). Dulbecco's modified Eagle's medium (DMEM) was purchased from Fisher Scientific (Fairlawn, N.J.). Oligonucleotide primers were synthesized by the Integrated DNA Technologies and Analysis Facility of the University of Kentucky. 3,3',5,5'-Tetramethylbenzidine (TMB) was obtained from Sigma (Saint Louis, Mo.). Anti-butyrylcholinesterase (mouse monoclonal antibody, Product #HAH002-01) was purchased from AntibodyShop (Gentofte, Denmark) and Goat anti-mouse IgG HRP conjugate from Zymed (San Francisco, Calif.).

Site-Directed Mutagenesis, Protein Expression, and BChE Activity Assay.

Site-directed mutagenesis of human BChE cDNA was performed by using the QuikChange method of Braman et al. Mutations were generated from wild-type human BChE in a pRc/CMV expression plasmid in accordance with (a) Masson, P.; Legrand, P.; Bartels, C. F.; Froment, M.-T.; Schopfer, L. M.; Lockridge, O. *Biochemistry* 1997, 36, 2266, (b) Masson, P.; Xie, W., Froment, M-T.; Levitsky, V.; Fortier, P.-L.; Albaret, C.; Lockridge, O. *Biochim. Biophys. Acta* 1999, 1433, 281, (c) Xie, W.; Altamirano, C. V.; Bartels, C. F.; Speirs, R. J.; Cashman, J. R.; Lockridge, O. *Mol. Pharmacol.* 1999, 55, 83, (d) Duysen, E. G.; Bartels, C. F.; Lockridge, O. *J. Pharmacol. Exp. Ther.* 2002, 302, 751, (e) Nachon, F.; Nicolet, Y.; Viguie, N.; Masson, P.; Fontecilla-Camps, J. C.; Lockridge, O. *Eur. J. Biochem.* 2002, 269, 630, herein all incorporated by reference. Using plasmid DNA as template and primers with specific base-pair alterations, mutations were made by polymerase chain reaction with Pfu DNA polymerase, for replication fidelity. The PCR product was treated with Dpn I endonuclease to digest the parental DNA template. Modified plasmid DNA was transformed into *Escherichia coli*, amplified, and purified. The DNA sequences of the mutants were confirmed by DNA sequencing. BChE mutants were expressed in human embryonic kidney cell line 293T/17. Cells were grown to 80-90% confluence in 6-well dishes and then transfected by Lipofectamine 2000 complexes of 4 μg plasmid DNA per each well. Cells were incubated at 37° C. in a $CO_2$ incubator for 24 hours and cells were moved to 60-mm culture vessel and cultured for four more days. The culture medium [10% fetal bovine serum in Dulbecco's modified Eagle's medium (DMEM)] was harvested for a BChE activity assay. To measure (−)-cocaine and benzoic acid, the product of (−)-cocaine hydrolysis catalyzed by BChE, sensitive radiometric assays were used based on toluene extraction of [$^{3}$H]-(−)-cocaine labeled on its benzene ring in accordance with Sun et al. In brief, to initiate the enzymatic reaction, 100 nCi of [$^{3}$H]-(−)-cocaine was mixed with 100 μl of culture medium. The enzymatic reactions proceeded at room temperature (25° C.) for varying time. The reactions were stopped by adding 300 μl of 0.02 M HCl, which neutralized the liberated benzoic acid while ensuring a positive charge on the residual (−)-cocaine. [$^{3}$H]benzoic acid was extracted by 1 ml of toluene and measured by scintillation counting. Finally, the measured time-dependent radiometric data were fitted to the kinetic equation so that the catalytic efficiency ($k_{cat}/K_M$) was determined along with the use of an enzyme-linked immunosorbent assay (ELISA) described below.

Enzyme-Linked Immunosorbent Assay (ELISA).

The ELISA buffers used in the present study are the same as those described in the literature such as (a) Brock, A.; Mortensen, V.; Loft, A. G. R.; Nergaard-Pedersen, B. *J. Clin. Chem. Clin. Biochem.* 1990, 28, 221-224, (b) Khattab, A. D.; Walker, C. H.; Johnston, G.; Siddiqui, M. K. Saphier, P. W. *Environmental Toxicology and Chemistry* 1994, 13, 1661-1667, herein both incorporated by reference. The coating buffer was 0.1 M sodium carbonate/bicarbonate buffer, pH 9.5. The diluent buffer (EIA buffer) was potassium phosphate monobasic/potassium phosphate monohydrate buffer, pH 7.5, containing 0.9% sodium chloride and 0.1% bovine serum albumin. The washing buffer (PBS-T) was 0.01 M potassium phosphate monobasic/potassium phosphate monohydrate buffer, pH 7.5, containing 0.05% (v/v) Tween-20. All the assays were performed in triplicate. Each well of an ELISA microtiter plate was filled with 100 μl of the mixture buffer consisting of 20 μl culture medium and 80 μl coating buffer. The plate was covered and incubated overnight at 4° C. to allow the antigen to bind to the plate. The solutions were then removed and the wells were washed four times with PBS-T. The washed wells were filled with 200 μl diluent buffer and kept shaking for 1.5 h at room temperature (25° C.). After washing with PBS-T for four times, the wells were filled with 100 μl antibody (1:8000) and were incubated for 1.5 h, followed by washing for four times. Then, the wells were filled with 100 μl goat anti-mouse IgG HRP conjugate complex diluted to a final 1:3000 dilution, and were incubated at room temperature for 1.5 h, followed by washing for four times. The enzyme reactions were started by addition of 100 μl substrate (TMB) solution. The reactions were stopped after 15 min by the addition of 100 μl of 2 M sulfuric acid, and the absorbance was read at 460 nm using a Bio-Rad ELISA plate reader.

Hydrogen Bonding Revealed by the MD Simulations.

In accordance with one aspect of the present invention, namely the generation of high-activity mutants of BChE against (−)-cocaine, the present invention includes predicting some possible mutations that can lower the energy of the transition state for the first chemical reaction step (TS1) and, therefore, lower the energy barrier for this critical reaction step. Apparently, a mutant associated with the stronger hydrogen bonding between the carbonyl oxygen of (−)-cocaine benzoyl ester and the oxyanion hole of the BChE mutant in the TS1 structure may potentially have a more stable TS1 structure and, therefore, a higher catalytic activity for (−)-cocaine hydrolysis. Hence, the hydrogen bonding with the oxyanion hole in the TS1 structure is a crucial factor affecting the transition state stabilization and the catalytic activity. The possible effects of some mutations on the hydrogen bonding were examined by performing MD simulations and QM/MM calculations on the TS1 structures for (−)-cocaine hydrolysis catalyzed by the wild-type and various mutants BChE's.

The MD simulation in water was performed for 1 ns or longer to make sure a stable MD trajectory was obtained for each simulated TS1 structure with the wild-type or mutant BChE. The MD trajectories actually became stable quickly, so were the H . . . O distances involved in the potential hydrogen bonds between the carbonyl oxygen of (−)-cocaine and the oxyanion hole of BChE.

Figure 5:
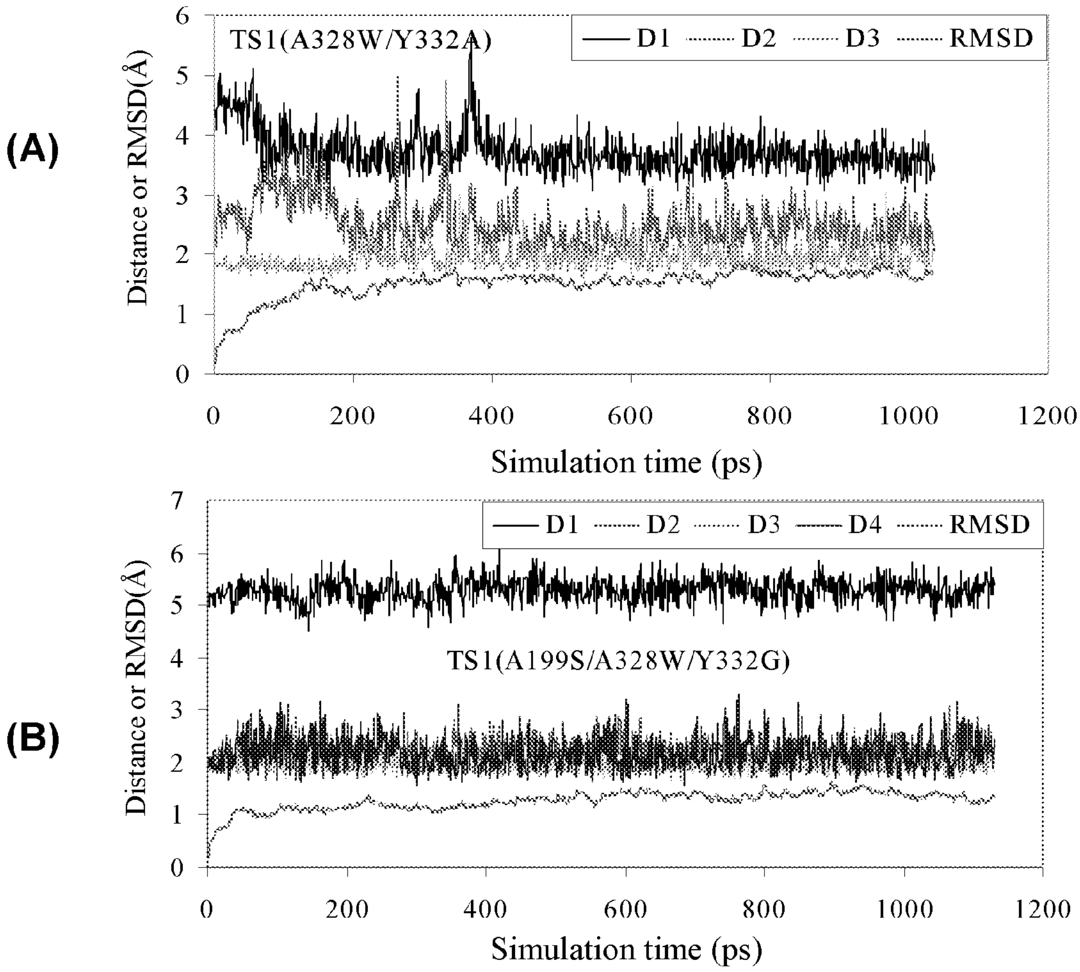
FIG. 5A is a plot of the key internuclear distances (in A) versus the time in the simulated TS1 structure for (−)-cocaine hydrolysis catalyzed by A328W/Y332A.
FIG. 5B for A199S/A328W/Y332G BChE.

Depicted in FIG. 5 are plots of four important H . . . O distances in the MD-simulated TS1 structure versus the simulation time for (−)-cocaine hydrolysis catalyzed by A328W/Y332A or A199S/A328W/Y332G BChE, along with the root-mean-square deviation (RMSD) of the simulated positions of backbone atoms from those in the corresponding initial structure. Traces D1, D2, and D3 refer to the distances between the carbonyl oxygen of (−)-cocaine and the NH hydrogen of G116, G117, and S199, respectively. Trace D4 is the internuclear distance between the carbonyl oxygen of (−)-cocaine and the hydroxyl hydrogen of the S199 side chain which exists only in A199S/A328W/Y332G BChE. RMSD represents the root-mean-square deviation (in A) of the simulated positions of the protein backbone atoms from those in the initial structure. The H . . . O distances in the simulated TS1 structures corresponding to the wild-type BChE and the two mutants are summarized in Table 3. The H . . . O distances between the carbonyl oxygen of (−)-cocaine and the peptidic NH hydrogen atoms of G116, G117, and A199 (or S199) of BChE are denoted by D1, D2, and D3, respectively, in Table 2 and FIG. 1. D4 in Table 3 and FIG. 5 refers to the H . . . O distance between the carbonyl oxygen of (−)-cocaine and the hydroxyl hydrogen of S199 side chain in the simulated TS1 structure corresponding to the A199S/A328W/Y332G mutant, mutant (1) (SEQ ID NO: 2).

Table 3. Summary of the MD-simulated and QM/MM-optimized key distances (in A) and the calculated total hydrogen-bonding energies (HBE, in kcal/mol) between the oxyanion hole and the carbonyl oxygen of (−)-cocaine benzoyl ester in the first transition state (TS1).

| Transition | | | Distance[a] | | | | Total |
|---|---|---|---|---|---|---|---|
| State | | Method | D1 | D2 | D3 | D4 | HBE[b] |
| TS1 for | MD | Average | 4.59 | 2.91 | 1.92 | | −5.5 (−4.6) |
| (−)-cocaine | | Maximum | 5.73 | 4.14 | 2.35 | | |
| hydrolysis | | Minimum | 3.35 | 1.97 | 1.61 | | |
| catalyzed | | Fluctuation | 0.35 | 0.35 | 0.12 | | |
| by wild-type BChE | | QM/MM | 4.10 | 2.21 | 2.05 | | −4.2 |
| TS1 for | MD | Average | 3.62 | 2.35 | 1.95 | | −6.2 (−4.9) |
| (−)-cocaine | | Maximum | 4.35 | 3.37 | 3.02 | | |
| hydrolysis | | Minimum | 2.92 | 1.78 | 1.61 | | |
| catalyzed | | Fluctuation | 0.23 | 0.27 | 0.17 | | |
| by A328W/Y332A mutant | | QM/MM | 3.39 | 2.05 | 2.47 | −3.3 | |
| TS1 for | MD | Average | 5.30 | 2.21 | 1.94 | 2.15 | −9.7 (−7.4) |
| (−)-cocaine | | Maximum | 6.08 | 3.06 | 2.47 | 3.27 | |
| hydrolysis | | Minimum | 4.57 | 1.71 | 1.66 | 1.56 | |
| catalyzed by | | Fluctuation | 0.22 | 0.20 | 0.13 | 0.29 | |
| A199S/A328W/ | | QM/MM | 4.83 | 2.09 | 1.91 | 2.59 | −7.46 |

[a]D1, D2, and D3 represent the internuclear distances between the carbonyl oxygen of cocaine benzoyl ester and the NH hydrogen of residues #116 (i.e., G116), #117 (i.e., G117), and #119 (i.e., A199 or S199) of BChE, respectively. D4 is the internuclear distance between the carbonyl oxygen of cocaine benzoyl ester and the hydroxyl hydrogen of S199 side chain in the A199S/A328W/Y332G mutant.

[b]The total HBE value under MD is the average of the HBE values calculated by using the instantaneous distances in all of the snapshots. The value in the parenthesis is the total HBE value calculated by using the MD-simulated average distances. The total HBE value under QM/MM was evaluated by using the QM/MM-optimized distances.

As seen in Table 3, the simulated H . . . O distance D1 is always too long for the peptidic NH of G116 to form a N—H . . . O hydrogen bond with the carbonyl oxygen of (−)-cocaine. In the simulated TS1 structure corresponding to wild-type BChE, the carbonyl oxygen of (−)-cocaine formed a firm N—H . . . O hydrogen bond with the peptidic NH hydrogen atom of A199 residue; the simulated H . . . O distance was 1.61 to 2.35 Å, with an average value of 1.92 Å. Meanwhile, the carbonyl oxygen of (−)-cocaine also had a partial N—H . . . O hydrogen bond with the peptidic NH hydrogen atom of G117 residue; the simulated H . . . O distance was 1.97 to 4.14 Å (the average value: 2.91 Å). In the simulated TS1 structure corresponding to the A328W/Y332A mutant, the simulated average H . . . O distances with the peptidic NH hydrogen of G117 and A199 are 2.35 and 1.95 Å, respectively. These distances suggest a slightly weaker N—H . . . O hydrogen bond with A199, but a stronger N—H . . . O hydrogen bond with G117, in the simulated TS1 structure corresponding to the A328W/Y332A mutant. The overall strength of the hydrogen bonding between the carbonyl oxygen of (−)-cocaine and the oxyanion hole of the enzyme is not expected to change considerably when wild-type BChE is replaced by the A328W/Y332A mutant.

However, the story for the simulated TS1 structure associated with the A199S/A328W/Y332G mutant was remarkably different. As one can see from Scheme 4, FIG. 5, and Table 3, when residue #199 becomes a serine (i.e., S199), the hydroxyl group on the side chain of S199 can also hydrogen-bond to the carbonyl oxygen of (−)-cocaine to form an O—H . . . O hydrogen bond, in addition to the two N—H . . . O hydrogen bonds with the peptidic NH of G117 and S199. The simulated average H . . . O distances with the peptidic NH hydrogen of G117, peptidic NH hydrogen of S199, and hydroxyl hydrogen of S199 are 2.21, 1.94, and 2.15 Å, respectively. Due to the additional O—H . . . O hydrogen bond, the overall strength of the hydrogen bonding with the modified oxyanion hole of A199S/A328W/Y332G BChE should be significantly stronger than that of the wild-type and A328W/Y332A BChE's.

To better represent the overall strength of hydrogen bonding between the carbonyl oxygen of (−)-cocaine and the oxyanion hole in a MD-simulated TS1 structure, the hydrogen bonding energy (HBE) associated with each simulated H . . . O distance was estimated by using the empirical HBE equation implemented in AutoDock 3.0 program suite in accordance with (a) Morris, G. M.; Goodsell, D. S.; Halliday, R. S.; Huey, R.; Hart, W. E.; Belew. R. K.; Olson, A. J. *J. Comput. Chem.* 1998, 19, 1639-1662, and based on the general HBE equation, $HBE(r) \approx 5\in r_0^{12}/r^{12} - 6\in r_0^{10}/r^{10}$, in which r is the H . . . O distance in the considered hydrogen bond and $r_0$ is the minimum value of the H . . . O distance for which the HBE equation can be used. For the calculation, $r_0$=1.52 Å, because it is the shortest H . . . O distance found in all of our MD simulations. The ∈ value was determined by using the condition that HBE(r)=−5.0 kcal/mol when r=1.90 Å, herein incorporated by reference. Specifically, for each hydrogen bond with the carbonyl oxygen of (−)-cocaine, a HBE value can be evaluated with each snapshot of the MD-simulated structure. The final HBE of the MD-simulated hydrogen bond is considered to be the average HBE value of all snapshots taken from the stable MD trajectory. The estimated total HBE value for the hydrogen bonds between the carbonyl oxygen of (−)-cocaine and the oxyanion hole in each simulated TS1 structure is given in Table 3.

The HBE for each hydrogen bond was estimated by using the MD-simulated average H . . . O distance. As seen in Table 3, the total hydrogen-bonding energies (i.e., −4.6, −4.9, and −7.4 kcal/mol for the wild-type, A328W/Y332A, and A199S/A328W/Y332G BChE's, respectively) estimated in this way are systematically higher (i.e., less negative) than the corresponding total hydrogen-bonding energies (i.e., −5.5, −6.2, and −9.7 kcal/mol) estimated in the aforementioned way. However, the two sets of total HBE values are qualitatively consistent in terms of the relative hydrogen-bonding strengths in the three simulated TS1 structures. In particular, the two sets of total HBE values consistently reveal that the overall strength of the hydrogen bonding between the carbonyl oxygen of (−)-cocaine and the oxyanion hole in the simulated TS1 structure for A199S/A328W/Y332G BChE is significantly higher than that for the wild-type and A328W/Y332A BChE's.

Hydrogen Bonding Based on the QM/MM Calculations.

The above conclusion obtained from the MD simulations was further examined by carrying out QM/MM calculations. Although this enzymatic reaction system is too large to calculate the QM/MM force constant matrix required in the automated search for a first-order saddle point corresponding to TS1, a partial geometry optimization was performed by fixing the length of the transition C—O bond between the carbonyl carbon of (−)-cocaine and the $O^\gamma$ atom of S198 in the QM/MM calculation. This transition C—O bond length dominates the reaction coordinate, according to the previous first-principle reaction coordinate calculations, in accordance with Zhan et al, with an active model of wild-type BChE. In the partial geometry optimization, the transition C—O bond length was fixed at that in the TS1 geometry optimized previously by performing the first-principle reaction coordinate calculation with an active site model of wild-type BChE. This partially optimized geometry should be close to the precisely defined TS1 geometry associated with a first-order saddle point on the potential energy surface, particularly for the hydrogen bonding between the carbonyl oxygen of (−)-cocaine and the oxyanion hole of BChE.

The QM/MM results summarized in Table 3 demonstrate two hydrogen bonds in each of the QM/MM-optimized TS1 structures. Specifically, D2=2.21 Å and D3=2.05 Å in the optimized TS1 structure for wild-type BChE; D2=2.05 Å and D3=2.47 Å in the optimized TS1 structure for the A328W/Y332A mutant; D2=2.09 Å, D3=1.91 Å, and D4=2.59 Å in the optimized TS1 structure for the A199S/A328W/Y332G mutant. Although the QM/MM-optimized individual H . . . O distances and the estimated HBE values are different from the corresponding values for individual hydrogen bonds, the relative total HBE values (i.e., −4.2, −3.3, and −7.46 kcal/mol for the wild-type, A328W/Y332A, and A199S/A328W/Y332G BChE's, respectively) estimated from these optimized distances are qualitatively consistent with the corresponding total HBE values (i.e., −4.6, −4.9, and −7.4 kcal/mol) estimated from the MD-simulated average H . . . O distances.

It should be pointed out that the absolute HBE values estimated in this study are not expected to be accurate, as different computational approaches led different HBE values. Nevertheless, for the purpose of our computational design of a high-activity mutant of BChE, one only needs to know the relative strength of the hydrogen bonding based on the estimated relative total HBE values of different mutants. The three sets of total HBE values (Table 3) estimated from the MD-simulated and QM/MM-optimized H . . . O distances all consistently demonstrate: (1) the overall strength of hydrogen bonding between the carbonyl oxygen of (−)-cocaine and the oxyanion hole in the TS1 structure for (−)-cocaine hydrolysis catalyzed by A328W/Y332A BChE should be close to that in the TS1 structure for (−)-cocaine hydrolysis catalyzed by wild-type BChE; (2) the overall hydrogen bonding between the carbonyl oxygen of (−)-cocaine and the oxyanion hole in the TS1 structure for (−)-cocaine hydrolysis catalyzed by A199S/A328W/Y332G BChE should be significantly stronger than that in the TS1 structure for (−)-cocaine hydrolysis catalyzed by A328W/Y332A BChE.

Catalytic Activity.

The computational results discussed above suggest that the transition state for the first chemical reaction step (TS1) of (−)-cocaine hydrolysis catalyzed by the A199S/A328W/Y332G mutant should be significantly more stable than that by the A328W/Y332A mutant, due to the significant increase of the overall hydrogen bonding between the carbonyl oxygen of (−)-cocaine and the oxyanion hole of the enzyme in the TS1 structure. The aforementioned analysis of the literature, namely Sun et al and Hamza et al, also indicate that the first chemical reaction step associated with TS1 should be the rate-determining step of (−)-cocaine hydrolysis catalyzed by a BChE mutant including Y332A or Y332G mutation, although the formation of the prereactive enzyme-substrate complex (ES) is the rate-determining step for (−)-cocaine hydrolysis catalyzed by wild-type BChE. This provides evidence of a clear correlation between the TS1 stabilization and the catalytic activity of A328W/Y332A and A199S/A328W/Y332G BChE's for (−)-cocaine hydrolysis: the more stable the TS1 structure, the lower the energy barrier, and the higher the catalytic activity. Thus, both the MD simulations and QM/MM calculations predict that A199S/A328W/Y332G BChE should have a higher catalytic activity than A328W/Y332A BChE for (−)-cocaine hydrolysis.

The catalytic efficiency ($k_{cat}/K_M$) of A328W/Y332A BChE for (−)-cocaine hydrolysis was reported by Sun et al to be ~$8.6\times10^6$ M $min^{-1}$, which is ~9.4 times of the $k_{cat}/K_M$ value (~$9.1\times10^5$ M $min^{-1}$) of wild-type BChE. To examine the theoretical prediction of the higher catalytic activity for A199S/A328W/Y332G BChE, A328W/Y332A and A199S/A328W/Y332G mutants of BChE were produced through site-directed mutagenesis. To minimize the possible systematic experimental errors of the kinetic data, kinetic studies were performed with the two mutants and wild-type BChE under the same condition and compared the catalytic efficiency of A328W/Y332A and A199S/A328W/Y332G BChE's to that of the wild-type for (−)-cocaine hydrolysis at benzoyl ester group. Based on the kinetic analysis of the measured time-dependent radiometric data and the ELISA data, the ratio of the $k_{cat}/K_M$ value of A328W/Y332A BChE to the $k_{cat}/K_M$ value of wild-type BChE for (−)-cocaine hydrolysis was determined to be ~8.6. The determined catalytic efficiency ratio of ~8.6 is in good agreement with the ratio of ~9.4 determined by Sun et al. Further, by using the same experimental protocol, the ratio of the $k_{cat}/K_M$ value of A199S/A328W/Y332G BChE to the $k_{cat}/K_M$ value of A328W/Y332A BChE for (−)-cocaine hydrolysis was determined to be ~7.2. These data indicate that the ratio of the $k_{cat}/K_M$ value of A199S/A328W/Y332G BChE to the $k_{cat}/K_M$ value of wild-type BChE for (−)-cocaine hydrolysis should be ~7.2×8.6=~62 or ~7.2×9.4=~68. Thus, A199S/A328W/Y332G BChE has a ~(65±6)-fold improved catalytic efficiency against (−)-cocaine compared to the wild-type, or A199S/A328W/Y332G BChE has a $k_{cat}/K_M$ value of ~$(5.9\pm0.5)\times10^7$ M $min^{-1}$ for (−)-cocaine hydrolysis.

Very recently reported F227A/S287G/A328W/Y332M BChE (i.e., AME-359, $k_{cat}/K_M$=$3.1\times10^7$ M $min^{-1}$) has a ~34-fold improved catalytic efficiency for (−)-cocaine hydrolysis. AME-359 has the highest catalytic efficiency against (−)-cocaine within all of the BChE mutants reported in literature prior to the present study. The catalytic efficiency for our A199S/A328W/Y332G BChE is about two times of that for AME-359 against (−)-cocaine.

Conclusion.

Molecular dynamics (MD) simulations and hybrid quantum mechanical/molecular mechanical (QM/MM) calculations on the transition state for the first chemical reaction step (TS1) of (−)-cocaine hydrolysis catalyzed by butyrylcholinesterase (BChE) mutants lead to a better understanding of the effects of protein environment on the transition state stabilization. All of the computational results consistently demonstrate that the overall hydrogen bonding between the carbonyl oxygen of (−)-cocaine benzoyl ester and the oxyanion hole of BChE in the TS1 structure for (−)-cocaine hydrolysis catalyzed by A199S/A328W/Y332G BChE should be significantly stronger than that in the TS1 structure for (−)-cocaine hydrolysis catalyzed by the wild-type and A328W/Y332A BChE's. Thus, both the MD simulations and QM/MM calculations predict that A199S/A328W/Y332G BChE should have a lower energy barrier for the chemical reaction process and, therefore, a higher catalytic efficiency ($k_{cat}/K_M$) for (−)-cocaine hydrolysis; A328W/Y332A BChE has been known to have a ~9-fold improved catalytic efficiency for (−)-cocaine hydrolysis. The theoretical prediction has been confirmed by wet experimental tests showing a ~(65±6)-fold improved catalytic efficiency for A199S/A328W/Y332G BChE against (−)-cocaine compared to the wild-type BChE. The $k_{cat}/K_M$ value determined for A199S/A328W/Y332G BChE is about two times of the $k_{cat}/K_M$ value for F227A/S287G/A328W/Y332M BChE (i.e., AME-359, which has the highest catalytic efficiency within all BChE mutants reported prior to the present study) against (−)-cocaine. The encouraging outcome of this study suggests that the transition-state modeling is a promising approach for rational design of high-activity mutants of BChE as a therapeutic treatment of cocaine abuse.

Experiment 3

MD Simulation and Generation of Mutant A199S/S287G/A328W/Y332G BChE (Mutant 3) (SEQ ID NO: 14)

The following simulation and mutant generation relate to A199S/S287G/A328W/Y332G (mutant 3) as a rational design of a high-activity mutant of BChE against (−)-cocaine based on detailed computational modeling of the transition state for the rate-determining step (i.e., the first step of the chemical reaction process). Molecular dynamics (MD) simulations were performed to model the protein environmental effects on the stabilization of the transition-state structure for BChE-catalyzed hydrolysis of (−)-cocaine as described above for mutant A199S/A328W/Y332G (mutant 1). The simulated results indicate that the transition-state structure can be stabilized much better by the protein environment in A199S/S287G/A328W/Y332G BChE than that in wild-type BChE and in other BChE mutants examined. The computational modeling led to a prediction of the higher catalytic efficiency for the A199S/S287G/A328W/Y332G mutant against (−)-cocaine. The prediction has been confirmed by wet experimental tests showing that the A199S/S287G/A328W/Y332G mutant has a remarkably improved catalytic efficiency against (−)-cocaine. All of the obtained results clearly demonstrate that directly modeling the transition-state structure provides a reliable computational approach to the rational design of a high-activity mutant of BChE against (−)-cocaine.

MD Simulations.

As with the A199S/A328W/Y332G mutant, when performing any MD simulation on a transition state, in principle, MD simulation using a classical force field (molecular mechanics) can only simulate a stable structure corresponding to a local minimum on the potential energy surface, whereas a transition state during a reaction process is always associated with a first-order saddle point on the potential energy surface.

The initial BChE structures used in the MD simulations were prepared based on our previous MD simulation as above with the prior mutant and the prereactive BChE-(−)-cocaine complex (ES) started from the X-ray crystal structure deposited in the Protein Data Bank (pdb code: 1P0P).

The general procedure for carrying out the MD simulations in water is essentially the same as that used in the computational studies for mutant A199S/A328W/Y332G (mutant 1). Site-directed mutagenesis of human BChE cDNA was performed as described before.

Figure 6:
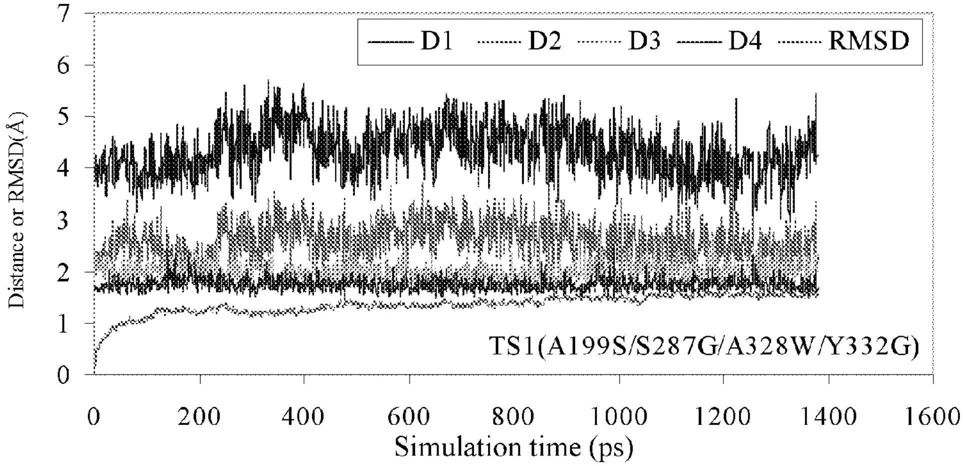
FIG. 6 is a plot of key internuclear distances (in A) versus the time in the simulated TS1 structure for (−)-cocaine hydrolysis catalyzed by A199S/S287G/A328W/Y332G BChE.

The MD simulation in water was performed as described above, on this mutant. Depicted in FIG. 6 are plots of four important H . . . O distances in the MD-simulated TS1 structure versus the simulation time for (−)-cocaine hydrolysis catalyzed by A199S/S287G/A328W/Y332G BChE, along with the root-mean-square deviation (RMSD) of the simulated positions of backbone atoms from those in the corresponding initial structure. Traces D1, D2, and D3 refer to the distances between the carbonyl oxygen of (−)-cocaine and the NH hydrogen of G116, G117, and S199, respectively. Trace D4 is the internuclear distance between the carbonyl oxygen of (−)-cocaine and the hydroxyl hydrogen of the S199 side chain in A199S/S287G/A328W/Y332G BChE (mutant 3). RMSD represents the root-mean-square deviation (in A) of the simulated positions of the protein backbone atoms from those in the initial structure.

The H . . . O distances in the simulated TS1 structures for wild-type BChE and its three mutants are summarized in Table 4. The H . . . O distances between the carbonyl oxygen of (−)-cocaine and the peptidic NH hydrogen atoms of G116, G117, and A199 (or S199) of BChE are denoted by D1, D2, and D3, respectively, in Table 4 and FIG. 6. D4 in Table 4 and FIG. 6 refers to the H . . . O distance between the carbonyl oxygen of (−)-cocaine and the hydroxyl hydrogen of S199 side chain in the simulated TS1 structure corresponding to the A199S/S287G/A328W/Y332G mutant.

Table 4. Summary of the MD-simulated key distances (in A) and the calculated total hydrogen-bonding energies (HBE, in kcal/mol) between the oxyanion hole and the carbonyl oxygen of (−)-cocaine benzoyl ester in the first transition state (TS1).

| Transition State | | Distance[a] D1 | D2 | D3 | D4 | Total HBE[b] |
|---|---|---|---|---|---|---|
| TS1 structure for (−)-cocaine | Average | 4.59 | 2.91 | 1.92 | | −5.5 (−4.6) |
| hydrolysis catalyzed | Maximum | 5.73 | 4.14 | 2.35 | | |
| by wild-type | Minimum | 3.35 | 1.97 | 1.61 | | |
| | Fluctuation | 0.35 | 0.35 | 0.12 | | |
| TS1 structure for (−)-cocaine | Average | 3.62 | 2.35 | 1.95 | | −6.2 (−4.9) |
| hydrolysis catalyzed | Maximum | 4.35 | 3.37 | 3.02 | | |
| by | Minimum | 2.92 | 1.78 | 1.61 | | |
| | Fluctuation | 0.23 | 0.27 | 0.17 | | |
| TS1 structure for (−)-cocaine | Average | 3.60 | 2.25 | 1.97 | | −6.4 (−5.0) |
| hydrolysis catalyzed | Maximum | 4.24 | 3.17 | 2.76 | | |
| by A328W/Y332G | Minimum | 2.89 | 1.77 | 1.62 | | |
| mutant of BChE | Fluctuation | 0.23 | 0.24 | 0.17 | | |
| TS1 structure for (−)-cocaine | Average | 4.39 | 2.60 | 2.01 | 1.76 | −14.0 (−12.0) |
| hydrolysis catalyzed | Maximum | 5.72 | 4.42 | 2.68 | 2.50 | |
| by A199S/S287G/ | Minimum | 2.87 | 1.76 | 1.62 | 1.48 | |
| A328W/Y332G | Fluctuation | 0.48 | 0.36 | 0.17 | 0.12 | |

[a]D1, D2, and D3 represent the internuclear distances between the carbonyl oxygen of cocaine benzoyl ester and the NH hydrogen of residues #116 (i.e., G116), #117 (i.e., G117), and #119 (i.e., A199 or S199) of BChE, respectively. D4 is the internuclear distance between the carbonyl oxygen of cocaine benzoyl ester and the hydroxyl hydrogen of S199 side chain in the A199S/A328W/Y332G mutant.

[b]The total HBE value under MD is the average of the HBE values calculated by using the instantaneous distances in all of the snapshots. The value in the parenthesis is the total HBE value calculated by using the MD-simulated average distances. The total HBE value under QM/MM was evaluated by using the QM/MM-optimized distances.

As seen in Table 4, the simulated H . . . O distance D1 is always too long for the peptidic NH of G116 to form a N—H . . . O hydrogen bond with the carbonyl oxygen of (−)-cocaine in all of the simulated TS1 structures. In the simulated TS1 structure for wild-type BChE, the carbonyl oxygen of (−)-cocaine formed a firm N—H . . . O hydrogen bond with the peptidic NH hydrogen atom of A199 residue; the simulated H . . . O distance (D2) was 1.61 to 2.35 Å, with an average D2 value of 1.92 Å. Meanwhile, the carbonyl oxygen of (−)-cocaine also had a partial N—H . . . O hydrogen bond with the peptidic NH hydrogen atom of G117 residue; the simulated H . . . O distance (D3) was 1.97 to 4.14 Å (the average D3 value: 2.91 Å). The average D2 and D3 values became 2.35 and 1.95 Å, respectively, in the simulated TS1 structure for the A328W/Y332A mutant. These distances suggest a slightly weaker N—H . . . O hydrogen bond with A199, but a stronger N—H . . . O hydrogen bond with G117, in the simulated TS1 structure for the A328W/Y332A mutant that the corresponding N—H . . . O hydrogen bonds for the wild-type. The average D2 and D3 values (2.25 and 1.97 Å, respectively) in the simulated TS1 structure for the A328W/Y332G mutant are close to the corresponding distances for the A328W/Y332A mutant. The overall strength of the hydrogen bonding between the carbonyl oxygen of (−)-cocaine and the oxyanion hole of the enzyme is not expected to change considerably when wild-type BChE is replaced by the A328W/Y332A or A328W/Y332G mutant.

However, the story for the simulated TS1 structure for the A199S/S287G/A328W/Y332G mutant was remarkably different. As one can see from Scheme 5, FIG. 6, and Table 4, when residue #199 becomes a serine (i.e., S199), the hydroxyl group on the side chain of S199 can also hydrogen-bond to the carbonyl oxygen of (−)-cocaine to form an O—H . . . O hydrogen bond, in addition to the two N—H . . . O hydrogen bonds with the peptidic NH of G117 and S199. The simulated average H . . . O distances with the peptidic NH hydrogen of G117, peptidic NH hydrogen of S199, and hydroxyl hydrogen of S199 are 2.60, 2.01, and 1.76 Å, respectively. Due to the additional O—H . . . O hydrogen bond, the overall strength of the hydrogen bonding with the modified oxyanion hole of A199S/S287G/A328W/Y332G BChE should be significantly stronger than that of wild-type, A328W/Y332A, and A328W/Y332G BChE's.

Scheme 5. Schematic representation of the transition-state structure for first reaction step for (-)-cocaine hydrolysis catalyzed by a BChE mutant with an A199S mutation.

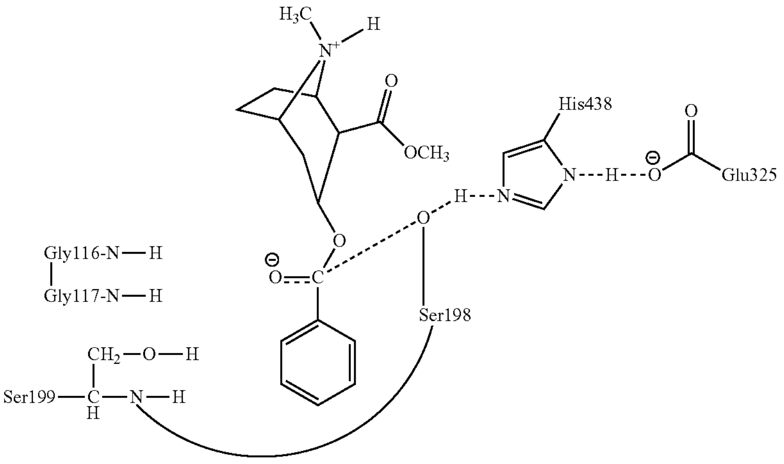

To better represent the overall strength of hydrogen bonding between the carbonyl oxygen of (−)-cocaine and the oxyanion hole in a MD-simulated TS1 structure, the hydrogen bonding energy (HBE) associated with each simulated H . . . O distance was estimated by using the empirical HBE equation implemented in AutoDock 3.0 program suite of (a) Masson, P.; Legrand, P.; Bartels, C. F.; Froment, M.-T.; Schopfer, L. M.; Lockridge, O. *Biochemistry* 1997, 36, 2266, (b) Masson, P.; Xie, W., Froment, M-T.; Levitsky, V.; Fortier, P.-L.; Albaret, C.; Lockridge, O. *Biochim. Biophys. Acta* 1999, 1433, 281, (c) Xie, W.; Altamirano, C. V.; Bartels, C. F.; Speirs, R. J.; Cashman, J. R.; Lockridge, O. *Mol. Pharmacol.* 1999, 55, 83, (d) Duysen, E. G.; Bartels, C. F.; Lockridge, O. *J. Pharmacol. Exp. Ther.* 2002, 302, 751, (e) Nachon, F.; Nicolet, Y.; Viguie, N.; Masson, P.; Fontecilla-Camps, J. C.; Lockridge, O. *Eur. J. Biochem.* 2002, 269, 630, herein all incorporated by reference. Specifically, for each hydrogen bond with the carbonyl oxygen of (−)-cocaine, a HBE value can be evaluated with each snapshot of the MD-simulated structure. The final HBE of the MD-simulated hydrogen bond is considered to be the average HBE value of all snapshots taken from the stable MD trajectory. The estimated total HBE value for the hydrogen bonds between the carbonyl oxygen of (−)-cocaine and the oxyanion hole in each simulated TS1 structure is also listed in Table 4.

The HBE for each hydrogen bond was estimated by using the MD-simulated average H . . . O distance. As seen in Table 4, the total hydrogen-bonding energies (i.e., −4.6, −4.9, −5.0, and −12.0 kcal/mol for the wild-type, A328W/Y332A, A328W/Y332G, and A199S/S287G/A328W/Y332G BChE's, respectively) estimated in this way are systematically higher (i.e., less negative) than the corresponding total hydrogen-bonding energies (i.e., −5.5, −6.2, −6.4, and −14.0 kcal/mol) estimated in the aforementioned way. However, the two sets of total HBE values are qualitatively consistent with each other in terms of the relative hydrogen-bonding strengths in the three simulated TS1 structures. In particular, the two sets of total HBE values consistently reveal that the overall strength of the hydrogen bonding between the carbonyl oxygen of (−)-cocaine and the oxyanion hole in the simulated TS1 structure for A199S/S287G/A328W/Y332G BChE is significantly higher than that for wild-type, A328W/Y332A, and A328W/Y332G BChE's.

Catalytic Activity.

The computational results discussed above provides evidence that the transition state for the first chemical reaction step (TS1) of (−)-cocaine hydrolysis catalyzed by the A199S/S287G/A328W/Y332G mutant should be significantly more stable than that by the A328W/Y332A or A328W/Y332G mutant, due to the significant increase of the overall hydrogen bonding between the carbonyl oxygen of (−)-cocaine and the oxyanion hole of the enzyme in the TS1 structure. The aforementioned analysis of the literature of Sun et al and Hamza et al also indicates that the first chemical reaction step associated with TS1 should be the rate-determining step of (−)-cocaine hydrolysis catalyzed by a BChE mutant including Y332A or Y332G mutation, although the formation of the prereactive enzyme-substrate complex (ES) is the rate-determining step for (−)-cocaine hydrolysis catalyzed by wild-type BChE. This suggests a clear correlation between the TS1 stabilization and the catalytic activity of A328W/Y332A, A328W/Y332G, and A199S/S287G/A328W/Y332G BChE's for (−)-cocaine hydrolysis: the more stable the TS1 structure, the lower the energy barrier, and the higher the catalytic activity. Thus, the MD simulations predict that A199S/S287G/A328W/Y332G BChE should have a higher catalytic activity than A328W/Y332A or A328W/Y332G BChE for (−)-cocaine hydrolysis.

The catalytic efficiency ($k_{cat}/K_M$) of A328W/Y332A BChE for (−)-cocaine hydrolysis was reported to be ~$8.6\times10^6$ M $min^{-1}$, which is ~9.4 times of the $k_{cat}/K_M$ value (~$9.1\times10^5$ M $min^{-1}$) of wild-type BChE for (−)-cocaine hydrolysis. The catalytic efficiency of A328W/Y332G BChE was found to be slightly higher than that of A328W/Y332A BChE for (−)-cocaine hydrolysis. To examine the theoretical prediction of the higher catalytic activity for A199S/S287G/A328W/Y332G BChE, the A328W/Y332A and A199S/S287G/A328W/Y332G mutants of BChE were produced as previously discussed through site-directed mutagenesis. To minimize the possible systematic experimental errors of the kinetic data, kinetic studies were performed with the two mutants and wild-type BChE under the same condition and compared the catalytic efficiency of A328W/Y332A and A199S/S287G/A328W/Y332G BChE's to that of the wild-type for (−)-cocaine hydrolysis at benzoyl ester group. Based on the kinetic analysis of the measured time-dependent radiometric data and the ELISA data, the ratio of the $k_{cat}/K_M$ value of A328W/Y332A BChE to the $k_{cat}/K_M$ value of wild-type BChE for (−)-cocaine hydrolysis was determined to be ~8.6. The determined catalytic efficiency ratio of ~8.6 is in good agreement with the ratio of ~9.4 determined by Sun et al. Further, by using the same experimental protocol, the ratio of the $k_{cat}/K_M$ value of A199S/S287G/A328W/Y332G BChE to the $k_{cat}/K_M$ value of A328W/Y332A BChE for (−)-cocaine hydrolysis was determined to be ~50.6. These data indicate that the ratio of the $k_{cat}/K_M$ value of A199S/S287G/A328W/Y332G BChE to the $k_{cat}/K_M$ value of wild-type BChE for (−)-cocaine hydrolysis should be ~50.6×8.6=~435 or ~50.6×9.4=~476. Thus, A199S/S287G/A328W/Y332G BChE has a ~(456±41)-fold improved catalytic efficiency against (−)-cocaine compared to the wild-type, or A199S/S287G/A328W/Y332G BChE has a $k_{cat}/K_M$ value of ~$(4.15\pm0.37)\times10^8$ M $min^{-1}$ for (−)-cocaine hydrolysis. The catalytic efficiency of A199S/S287G/A328W/Y332G BChE against (−)-cocaine is much higher than that of AME-359 (i.e., F227A/S287G/A328W/Y332M BChE, $k_{cat}/K_M=3.1\times10^7$ M min, whose catalytic efficiency against (−)-cocaine is the highest within all of the previously reported BChE mutants) which has a ~34-fold improved catalytic efficiency against (−)-cocaine compared to wild-type BChE.

By using the designed A199S/S287G/A328W/Y332G BChE as an exogenous enzyme in human, when the concentration of this mutant is kept the same as that of the wild-type BChE in plasma, the half-life time of (−)-cocaine in plasma should be reduced from the ~45-90 min to only ~6-12 seconds, considerably shorter than the time required for cocaine crossing the blood-brain barrier to reach CNS. Hence, the outcome of this study could eventually result in a valuable, efficient anti-cocaine medication.

Conclusion.

The transition-state simulations demonstrate that the overall hydrogen bonding between the carbonyl oxygen of (−)-cocaine benzoyl ester and the oxyanion hole of BChE in the TS1 structure for (−)-cocaine hydrolysis catalyzed by A199S/S287G/A328W/Y332G BChE should be significantly stronger than that in the TS1 structure for (−)-cocaine hydrolysis catalyzed by the wild-type BChE and other BChE mutants simulated. Thus, the MD simulations predict that A199S/S287G/A328W/Y332G BChE should have a significantly lower energy barrier for the chemical reaction process and, therefore, a significantly higher catalytic efficiency ($k_{cat}/K_M$) for (−)-cocaine hydrolysis. The theoretical prediction has been confirmed by wet experimental tests showing a ~(456±41)-fold improved catalytic efficiency for A199S/S287G/A328W/Y332G BChE against (−)-cocaine compared to the wild-type BChE. The $k_{cat}/K_M$ value determined for A199S/S287G/A328W/Y332G BChE is much higher than the $k_{cat}/K_M$ value for AME-359 (i.e., F227A/S287G/A328W/Y332M BChE, whose catalytic efficiency against (−)-cocaine is the highest within all of the BChE mutants reported previously in literature) which has a ~34-fold improved catalytic efficiency against (−)-cocaine compared to the wild-type BChE. The outcome of this study provides evidence that the transition-state simulation is a novel and unique approach for rational enzyme redesign and drug discovery.

Although the invention has been described in detail with respect to preferred embodiments thereof, it will be apparent that the invention is capable of numerous modifications and variations, apparent to those skilled in the art, without departing from the spirit and scope of the invention.

What is claimed is:

1. A method for generating butyrylcholinesterase mutants, said method comprising:

generating an initial structure of the transition state structure for the rate determining step of the cocaine hydrolysis catalyzed by a possible butyrylcholinesterase mutant;

performing a sufficiently long time molecular dynamics simulation on the transition state structure in water to have a stable molecular dynamic trajectory;

analyzing the molecular dynamic trajectory and estimating the hydrogen binding energies between the carbonyl oxygen of the (−)-cocaine benzoyl ester and the oxyanion hole of the possible butyrylcholinesterase mutant;

if the hydrogen binding energies between the carbonyl oxygen of the (−)-cocaine benzoyl ester and the possible butyrylcholinesterase mutant, in the transition state, are stronger than the hydrogen binding energies between the carbonyl oxygen of the (−)-cocaine benzoyl ester and wild type butyrylcholinesterase:

calculating the hydrogen binding energies, evaluating the energy barrier, and generating butyrylcholinesterase mutant.

2. The method of claim 1, wherein said generating an initial structure of the transition state structure is based on reaction coordinate calculations for the wild type butyrylcholinesterase.

3. The method of claim 1, wherein said generating butyrylcholinesterase mutant comprising:

performing site directed mutagenesis on a nucleic acid sequence encoding wild type butyrylcholinesterase, to generate the mutant butyrylcholinesterase nucleic acid sequence;

expressing a protein encoded by mutant nucleic acid sequence to produce mutant butyrylcholinesterase, and performing a catalytic activity assay on the mutant butyrylcholinesterase.

4. The method of claim 1, wherein said hybrid quantum mechanical/molecular mechanical geometry optimization, calculating the hydrogen binding energies, and evaluating the energy barrier are conducted only if the hydrogen binding energies between the carbonyl oxygen of the (−)-cocaine benzoyl ester and the possible butyrylcholinesterase mutant, in the transition state, are stronger than known butyrylcholinesterase mutants against (−)-cocaine.

5. The method of claim 1, further comprising determining the rate limiting step in the hydrolysis of (−)-cocaine by the possible butyrylcholinesterase mutant by conducting the molecular dynamic simulations and quantum mechanical/molecular mechanical calculations relating to the transition states for other reaction steps between (−)-cocaine by the possible butyrylcholinesterase mutant, and calculating respective energy barriers, thereby establishing which of the reaction steps is rate determining one.

6. The method of claim 1, wherein if the hydrogen binding energies between the carbonyl oxygen of the (−)-cocaine benzoyl ester and the possible butyrylcholinesterase mutant, in the transition state, are stronger than the hydrogen binding energies between the carbonyl oxygen of the (−)-cocaine benzoyl ester and wild type butyrylcholinesterase further performing hybrid quantum mechanical/molecular mechanical geometry optimization to refine the molecular dynamics-simulated structure prior to calculating the hydrogen binding energies.

* * * * *